US008613938B2

(12) United States Patent
Akella et al.

(10) Patent No.: US 8,613,938 B2
(45) Date of Patent: *Dec. 24, 2013

(54) BONE VOID FILLERS

(75) Inventors: Rama Akella, Austin, TX (US); Ian Ross Garrett, Austin, TX (US); Hai Bo Wen, Carlsbad, CA (US); Shuliang Li, Austin, TX (US); Dean M. Acker, Warsaw, IN (US); Nichole Wilhelm, Warsaw, IN (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/297,005

(22) Filed: Nov. 15, 2011

(65) Prior Publication Data

US 2012/0121660 A1    May 17, 2012

Related U.S. Application Data

(60) Provisional application No. 61/413,502, filed on Nov. 15, 2010, provisional application No. 61/541,690, filed on Sep. 30, 2011.

(51) Int. Cl.
*A61K 9/00* (2006.01)
*A61K 35/32* (2006.01)

(52) U.S. Cl.
USPC .......................................... 424/400; 424/549

(58) Field of Classification Search
USPC ................................................ 424/400, 549
See application file for complete search history.

(56) References Cited

U.S. PATENT DOCUMENTS

| 2,471,598 | A | 5/1949 | Wilt et al. |
| 3,368,911 | A | 2/1968 | Kuntz et al. |
| 3,393,080 | A | 7/1968 | Erdi et al. |
| 3,443,261 | A | 5/1969 | Battista et al. |

(Continued)

FOREIGN PATENT DOCUMENTS

| AU | 2007334213 | | 8/2012 |
| AU | 2007334213 | B2 | 8/2012 |

(Continued)

OTHER PUBLICATIONS

"U.S. Appl. No. 12/180,035, Second Preliminary Amendment filed Nov. 24, 2008", 3 pgs.

(Continued)

*Primary Examiner* — Aradhana Sasan
(74) *Attorney, Agent, or Firm* — Schwegman, Lundberg & Woessner P.A.

(57) ABSTRACT

A bone void filler composition is described containing an acidic mineral component that contains a calcium source and a phosphate source or a lower alkyl carboxylate source; an osteoinductive component that contains demineralized bone; and a three-dimensional, osteoconductive biologically acceptable carrier component that contains a collagenous material. The bone void filler composition may be in the form of a sponge or in the form of a paste or putty used to form a sponge or is obtained from particulated sponge, or that forms after a sponge is rehydrated. A pre-mixed bone void filler composition is described containing the acidic mineral component or the lower alkyl carboxylate source; the osteoinductive component; and a biologically acceptable carrier component that contains a liquid carrier. Methods of making and using the compositions are also described. The ratio of demineralized bone component to acidic mineral component may range from about 0.5:1 to about 80:1.

18 Claims, 24 Drawing Sheets

(56) References Cited

U.S. PATENT DOCUMENTS

| | | |
|---|---|---|
| 3,471,598 A | 10/1969 | Battista |
| 3,767,437 A | 10/1973 | Cruz, Jr. et al. |
| 3,919,723 A | 11/1975 | Heimke et al. |
| 3,949,073 A | 4/1976 | Daniels et al. |
| 3,968,567 A | 7/1976 | Nevins |
| 4,066,083 A | 1/1978 | Ries |
| 4,131,597 A | 12/1978 | Bluethgen et al. |
| 4,146,936 A | 4/1979 | Aoyagi et al. |
| 4,191,747 A | 3/1980 | Scheicher |
| 4,192,021 A | 3/1980 | Deibig et al. |
| 4,202,055 A | 5/1980 | Reiner et al. |
| 4,233,360 A | 11/1980 | Luck et al. |
| 4,237,559 A | 12/1980 | Borom |
| 4,273,705 A | 6/1981 | Kato |
| 4,294,753 A | 10/1981 | Urist |
| 4,356,572 A | 11/1982 | Guillemin et al. |
| 4,389,487 A | 6/1983 | Ries |
| 4,394,370 A | 7/1983 | Jefferies |
| 4,412,947 A | 11/1983 | Cioca |
| 4,429,691 A | 2/1984 | Niwa et al. |
| 4,430,760 A | 2/1984 | Smestad |
| 4,440,680 A | 4/1984 | Cioca |
| 4,440,750 A | 4/1984 | Glowacki et al. |
| 4,451,397 A | 5/1984 | Huc et al. |
| 4,455,256 A | 6/1984 | Urist |
| 4,472,840 A | 9/1984 | Jefferies |
| 4,485,097 A | 11/1984 | Bell |
| 4,497,075 A | 2/1985 | Niwa et al. |
| 4,516,276 A | 5/1985 | Mittelmeier |
| 4,557,764 A | 12/1985 | Chu |
| 4,563,350 A | 1/1986 | Nathan et al. |
| 4,563,489 A | 1/1986 | Urist |
| 4,596,574 A | 6/1986 | Urist |
| 4,600,533 A | 7/1986 | Chu |
| 4,606,910 A | 8/1986 | Sawyer |
| 4,609,551 A | 9/1986 | Caplan et al. |
| 4,619,655 A | 10/1986 | Hanker et al. |
| 4,619,989 A | 10/1986 | Urist |
| 4,620,327 A | 11/1986 | Caplan et al. |
| 4,623,553 A | 11/1986 | Ries et al. |
| 4,629,464 A | 12/1986 | Takata et al. |
| 4,637,931 A | 1/1987 | Schmitz |
| 4,642,120 A | 2/1987 | Nevo et al. |
| 4,656,130 A | 4/1987 | Shoshan |
| 4,668,295 A | 5/1987 | Bajpai |
| 4,689,399 A | 8/1987 | Chu |
| 4,693,986 A | 9/1987 | Vit et al. |
| 4,698,326 A | 10/1987 | Sauk et al. |
| 4,703,108 A | 10/1987 | Silver et al. |
| 4,725,671 A | 2/1988 | Chu et al. |
| 4,743,229 A | 5/1988 | Chu |
| 4,761,471 A | 8/1988 | Urist |
| 4,774,227 A | 9/1988 | Piez et al. |
| 4,774,228 A | 9/1988 | Seyedin et al. |
| 4,774,322 A | 9/1988 | Seyedin et al. |
| 4,776,890 A | 10/1988 | Chu |
| 4,780,450 A | 10/1988 | Sauk et al. |
| 4,789,663 A | 12/1988 | Wallace et al. |
| 4,789,732 A | 12/1988 | Urist |
| 4,795,467 A | 1/1989 | Piez et al. |
| 4,795,804 A | 1/1989 | Urist |
| 4,804,744 A | 2/1989 | Sen |
| 4,810,691 A | 3/1989 | Seyedin et al. |
| 4,839,215 A | 6/1989 | Starling et al. |
| 4,843,063 A | 6/1989 | Seyedin et al. |
| 4,843,112 A | 6/1989 | Gerhart et al. |
| 4,846,838 A | 7/1989 | Takai et al. |
| 4,863,732 A | 9/1989 | Nathan et al. |
| 4,863,856 A | 9/1989 | Dean, Jr. et al. |
| 4,865,602 A | 9/1989 | Smestad et al. |
| 4,888,366 A | 12/1989 | Chu et al. |
| 4,891,359 A | 1/1990 | Saferstein et al. |
| 4,919,670 A | 4/1990 | Dale et al. |
| 4,948,540 A | 8/1990 | Nigam |
| 4,950,483 A | 8/1990 | Ksander et al. |
| 4,970,298 A | 11/1990 | Silver et al. |
| 4,975,526 A | 12/1990 | Kuberasampath et al. |
| 4,975,527 A | 12/1990 | Koezuka et al. |
| 4,992,226 A | 2/1991 | Piez et al. |
| 4,997,446 A | 3/1991 | Thoma |
| 5,001,169 A | 3/1991 | Nathan et al. |
| 5,011,691 A | 4/1991 | Oppermann et al. |
| 5,024,841 A | 6/1991 | Chu et al. |
| 5,028,695 A | 7/1991 | Eckmayer et al. |
| 5,034,059 A | 7/1991 | Constantz |
| 5,035,715 A | 7/1991 | Smestad et al. |
| 5,047,031 A | 9/1991 | Constantz |
| 5,053,212 A | 10/1991 | Constantz et al. |
| 5,061,286 A | 10/1991 | Lyle |
| 5,069,905 A | 12/1991 | Lidor et al. |
| 5,071,434 A | 12/1991 | Tsuzuki et al. |
| 5,071,436 A | 12/1991 | Huc et al. |
| 5,073,373 A | 12/1991 | O'Leary et al. |
| 5,084,051 A | 1/1992 | Tormala et al. |
| 5,085,861 A | 2/1992 | Gerhart et al. |
| 5,090,815 A | 2/1992 | Bohle |
| 5,106,748 A | 4/1992 | Wozney et al. |
| 5,108,436 A | 4/1992 | Chu et al. |
| 5,108,753 A | 4/1992 | Kuberasampath et al. |
| 5,110,604 A | 5/1992 | Chu et al. |
| 5,118,667 A | 6/1992 | Adams et al. |
| 5,123,923 A | 6/1992 | Pommier et al. |
| 5,123,925 A | 6/1992 | Smestad et al. |
| 5,133,755 A | 7/1992 | Brekke et al. |
| 5,137,534 A | 8/1992 | Sumita |
| 5,152,836 A | 10/1992 | Hirano et al. |
| 5,154,931 A | 10/1992 | Kruger et al. |
| 5,158,934 A | 10/1992 | Ammann et al. |
| 5,162,114 A | 11/1992 | Kuberasampath et al. |
| 5,169,837 A | 12/1992 | Lagarde et al. |
| 5,171,574 A | 12/1992 | Kuberasampath et al. |
| 5,171,579 A | 12/1992 | Ron et al. |
| 5,204,382 A | 4/1993 | Wallace et al. |
| 5,206,023 A | 4/1993 | Hunziker |
| 5,207,710 A | 5/1993 | Chu et al. |
| 5,208,219 A | 5/1993 | Ogawa et al. |
| 5,231,169 A | 7/1993 | Constantz et al. |
| 5,236,456 A | 8/1993 | O'Leary et al. |
| 5,236,704 A | 8/1993 | Fujioka et al. |
| 5,246,457 A | 9/1993 | Piez et al. |
| 5,258,029 A | 11/1993 | Chu et al. |
| 5,262,166 A | 11/1993 | Liu et al. |
| 5,263,985 A | 11/1993 | Bao et al. |
| 5,270,300 A | 12/1993 | Hunziker |
| 5,273,964 A | 12/1993 | Lemons |
| 5,274,078 A | 12/1993 | Wada et al. |
| 5,279,831 A | 1/1994 | Constantz et al. |
| 5,290,494 A | 3/1994 | Coombes et al. |
| 5,290,558 A | 3/1994 | O'Leary et al. |
| 5,290,763 A | 3/1994 | Poser et al. |
| 5,304,577 A | 4/1994 | Nagata et al. |
| 5,306,303 A | 4/1994 | Lynch |
| 5,314,476 A | 5/1994 | Prewett et al. |
| 5,320,844 A | 6/1994 | Liu |
| 5,332,802 A | 7/1994 | Kelman et al. |
| 5,336,264 A | 8/1994 | Constanz et al. |
| 5,338,772 A | 8/1994 | Bauer et al. |
| 5,344,654 A | 9/1994 | Rueger et al. |
| 5,352,715 A | 10/1994 | Wallace et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,498 A | 11/1994 | Brannan et al. |
| 5,366,508 A | 11/1994 | Brekke et al. |
| 5,366,756 A | 11/1994 | Chesterfield et al. |
| 5,368,858 A | 11/1994 | Hunziker |
| 5,371,191 A | 12/1994 | Poser et al. |
| 5,376,375 A | 12/1994 | Rhee et al. |
| 5,393,739 A | 2/1995 | Bentz et al. |
| 5,397,572 A | 3/1995 | Coombes et al. |
| 5,399,361 A | 3/1995 | Song et al. |
| 5,405,390 A | 4/1995 | O'Leary et al. |
| 5,413,989 A | 5/1995 | Ogawa et al. |
| 5,417,975 A | 5/1995 | Lussi et al. |

(56) References Cited

U.S. PATENT DOCUMENTS

| | | |
|---|---|---|
| 5,422,340 A | 6/1995 | Ammann et al. |
| 5,425,770 A | 6/1995 | Piez et al. |
| 5,426,769 A | 6/1995 | Pawloski |
| 5,428,022 A | 6/1995 | Palefsky et al. |
| 5,433,751 A | 7/1995 | Christel et al. |
| 5,443,531 A | 8/1995 | Ripamonti |
| 5,455,231 A | 10/1995 | Constantz et al. |
| 5,466,462 A | 11/1995 | Rosenthal et al. |
| 5,475,052 A | 12/1995 | Rhee et al. |
| 5,484,601 A | 1/1996 | O'Leary et al. |
| 5,492,697 A | 2/1996 | Boyan et al. |
| 5,496,552 A | 3/1996 | Kuberasampath et al. |
| 5,507,813 A | 4/1996 | Dowd et al. |
| 5,508,267 A | 4/1996 | Czernuszka et al. |
| 5,510,396 A | 4/1996 | Prewett et al. |
| 5,522,893 A | 6/1996 | Chow et al. |
| 5,522,894 A | 6/1996 | Draenert et al. |
| 5,531,791 A | 7/1996 | Wolfinbarger, Jr. |
| 5,532,217 A | 7/1996 | Silver et al. |
| 5,543,394 A | 8/1996 | Wozney et al. |
| 5,547,378 A | 8/1996 | Linkow |
| 5,549,671 A | 8/1996 | Waybright et al. |
| 5,552,454 A | 9/1996 | Kretschmann et al. |
| 5,563,124 A | 10/1996 | Damien et al. |
| 5,565,502 A | 10/1996 | Glimcher et al. |
| 5,573,771 A | 11/1996 | Geistlich et al. |
| 5,599,552 A | 2/1997 | Dunn et al. |
| 5,604,204 A | 2/1997 | Ammann et al. |
| 5,618,339 A | 4/1997 | Ito |
| 5,618,549 A | 4/1997 | Patat et al. |
| 5,639,402 A | 6/1997 | Barlow et al. |
| 5,645,591 A | 7/1997 | Kuberasampath et al. |
| 5,650,176 A | 7/1997 | Lee et al. |
| 5,661,007 A | 8/1997 | Wozney et al. |
| 5,670,483 A | 9/1997 | Zhang et al. |
| 5,674,290 A | 10/1997 | Li et al. |
| 5,674,292 A | 10/1997 | Tucker et al. |
| 5,674,521 A | 10/1997 | Gehrke et al. |
| 5,676,146 A | 10/1997 | Scarborough |
| 5,676,699 A | 10/1997 | Gogolewski |
| 5,677,284 A | 10/1997 | Li |
| 5,679,723 A | 10/1997 | Cooper |
| 5,681,873 A | 10/1997 | Norton et al. |
| 5,683,459 A | 11/1997 | Brekke |
| 5,683,461 A | 11/1997 | Lee et al. |
| 5,686,425 A | 11/1997 | Lee |
| 5,691,397 A | 11/1997 | Glimcher et al. |
| RE35,694 E | 12/1997 | Seyedin et al. |
| 5,703,043 A | 12/1997 | Celeste et al. |
| 5,707,442 A | 1/1998 | Fogel et al. |
| 5,707,962 A | 1/1998 | Chen et al. |
| 5,709,934 A | 1/1998 | Bell et al. |
| 5,711,957 A | 1/1998 | Patat et al. |
| 5,728,679 A | 3/1998 | Celeste et al. |
| 5,733,337 A | 3/1998 | Carr, Jr. et al. |
| 5,739,286 A | 4/1998 | Silver et al. |
| 5,741,329 A | 4/1998 | Agrawal et al. |
| 5,750,146 A | 5/1998 | Jones et al. |
| 5,755,792 A | 5/1998 | Brekke |
| 5,756,457 A | 5/1998 | Wang et al. |
| 5,769,895 A | 6/1998 | Ripamonti |
| 5,769,897 A | 6/1998 | Harle |
| 5,776,193 A | 7/1998 | Kwan et al. |
| 5,811,094 A | 9/1998 | Caplan et al. |
| 5,814,604 A | 9/1998 | Oppermann et al. |
| 5,824,084 A | 10/1998 | Muschler |
| 5,824,087 A | 10/1998 | Aspden et al. |
| 5,830,340 A | 11/1998 | Iljitch et al. |
| 5,830,493 A | 11/1998 | Yokota et al. |
| 5,837,752 A | 11/1998 | Shastri et al. |
| 5,840,325 A | 11/1998 | Kuberasampath et al. |
| 5,846,312 A | 12/1998 | Ison et al. |
| 5,854,207 A | 12/1998 | Lee et al. |
| 5,899,939 A | 5/1999 | Boyce et al. |
| 5,904,717 A | 5/1999 | Brekke et al. |
| 5,904,718 A | 5/1999 | Jefferies |
| 5,906,827 A | 5/1999 | Khouri et al. |
| 5,910,315 A | 6/1999 | Stevenson et al. |
| 5,910,492 A | 6/1999 | Hoshino et al. |
| 5,916,553 A | 6/1999 | Schmidt |
| 5,916,870 A | 6/1999 | Lee et al. |
| 5,919,408 A | 7/1999 | Muller et al. |
| 5,922,025 A | 7/1999 | Hubbard |
| 5,928,635 A | 7/1999 | Schmidt |
| 5,932,207 A | 8/1999 | Schmidt |
| 5,935,594 A | 8/1999 | Ringeisen et al. |
| 5,948,426 A | 9/1999 | Jefferies |
| 5,948,428 A | 9/1999 | Lee et al. |
| 5,948,429 A | 9/1999 | Bell et al. |
| 5,952,010 A | 9/1999 | Constantz |
| 5,955,438 A | 9/1999 | Pitaru et al. |
| 5,955,529 A | 9/1999 | Imani et al. |
| 5,958,430 A | 9/1999 | Campbell et al. |
| 5,958,441 A | 9/1999 | Oppermann et al. |
| 5,964,805 A | 10/1999 | Stone |
| 5,972,368 A | 10/1999 | McKay |
| 5,990,381 A | 11/1999 | Nishihara |
| 5,997,895 A | 12/1999 | Narotam et al. |
| 6,005,161 A | 12/1999 | Brekke et al. |
| 6,013,853 A | 1/2000 | Athanasiou et al. |
| 6,013,856 A | 1/2000 | Tucker et al. |
| 6,018,095 A | 1/2000 | Lerch et al. |
| 6,027,742 A | 2/2000 | Lee et al. |
| 6,027,743 A | 2/2000 | Khouri et al. |
| 6,028,242 A | 2/2000 | Tucker et al. |
| 6,033,438 A | 3/2000 | Bianchi et al. |
| 6,037,519 A | 3/2000 | McKay |
| 6,039,762 A | 3/2000 | McKay |
| 6,048,964 A | 4/2000 | Lee et al. |
| 6,071,982 A | 6/2000 | Wise et al. |
| 6,077,988 A | 6/2000 | Kuberasampath et al. |
| 6,090,996 A | 7/2000 | Li |
| 6,110,482 A | 8/2000 | Khouri et al. |
| 6,118,043 A | 9/2000 | Nies et al. |
| 6,123,731 A | 9/2000 | Boyce et al. |
| 6,123,957 A | 9/2000 | Jernberg |
| 6,132,463 A | 10/2000 | Lee et al. |
| 6,132,468 A | 10/2000 | Mansmann |
| 6,136,029 A | 10/2000 | Johnson et al. |
| 6,136,030 A | 10/2000 | Lin et al. |
| 6,139,578 A | 10/2000 | Lee et al. |
| 6,165,487 A | 12/2000 | Ashkar et al. |
| 6,168,801 B1 | 1/2001 | Heil, Jr. et al. |
| 6,177,406 B1 | 1/2001 | Wang et al. |
| 6,180,605 B1 | 1/2001 | Chen et al. |
| 6,180,606 B1 | 1/2001 | Chen et al. |
| 6,183,515 B1 | 2/2001 | Barlow et al. |
| 6,183,737 B1 | 2/2001 | Zaleske et al. |
| 6,187,046 B1 | 2/2001 | Yamamoto et al. |
| 6,187,047 B1 | 2/2001 | Kwan et al. |
| 6,187,329 B1 | 2/2001 | Agrawal et al. |
| 6,187,742 B1 | 2/2001 | Wozney et al. |
| 6,189,537 B1 | 2/2001 | Wolfinbarger, Jr. |
| 6,201,039 B1 | 3/2001 | Brown et al. |
| 6,203,573 B1 | 3/2001 | Walter et al. |
| 6,203,574 B1 | 3/2001 | Kawamura |
| 6,206,924 B1 | 3/2001 | Timm |
| 6,206,931 B1 | 3/2001 | Cook et al. |
| 6,214,049 B1 | 4/2001 | Gayer et al. |
| 6,214,368 B1 | 4/2001 | Lee et al. |
| 6,221,109 B1 | 4/2001 | Geistlich et al. |
| 6,241,771 B1 | 6/2001 | Gresser et al. |
| 6,261,565 B1 | 7/2001 | Empie et al. |
| 6,261,586 B1 | 7/2001 | McKay |
| 6,264,701 B1 | 7/2001 | Brekke |
| 6,277,151 B1 | 8/2001 | Lee et al. |
| 6,280,191 B1 | 8/2001 | Gordon |
| 6,280,474 B1 | 8/2001 | Cassidy et al. |
| 6,281,195 B1 | 8/2001 | Rueger et al. |
| 6,287,341 B1 | 9/2001 | Lee et al. |
| 6,287,816 B1 | 9/2001 | Rosen et al. |
| 6,294,041 B1 | 9/2001 | Boyce et al. |
| 6,294,187 B1 | 9/2001 | Boyce et al. |
| 6,296,667 B1 | 10/2001 | Johnson et al. |

(56) References Cited

U.S. PATENT DOCUMENTS

| | | |
|---|---|---|
| 6,297,213 B1 | 10/2001 | Oppermann et al. |
| 6,299,650 B1 | 10/2001 | Van Blitterswijk et al. |
| 6,300,315 B1 | 10/2001 | Liu |
| 6,302,913 B1 | 10/2001 | Ripamonti et al. |
| 6,306,169 B1 | 10/2001 | Lee et al. |
| 6,309,422 B1 | 10/2001 | Farrington et al. |
| 6,309,909 B1 | 10/2001 | Ohgiyama |
| 6,311,690 B1 | 11/2001 | Jefferies |
| 6,326,018 B1 | 12/2001 | Gertzman et al. |
| 6,331,312 B1 | 12/2001 | Lee et al. |
| 6,335,007 B1 | 1/2002 | Shimizu et al. |
| 6,340,648 B1 | 1/2002 | Imura et al. |
| 6,346,123 B1 | 2/2002 | McKay |
| 6,352,972 B1 | 3/2002 | Nimni et al. |
| 6,371,985 B1 | 4/2002 | Goldberg |
| 6,372,257 B1 | 4/2002 | Marchosky |
| 6,376,211 B1 | 4/2002 | Little, II et al. |
| 6,379,385 B1 | 4/2002 | Kalas et al. |
| 6,383,519 B1 | 5/2002 | Sapieszko et al. |
| 6,384,196 B1 | 5/2002 | Weis et al. |
| 6,384,197 B1 | 5/2002 | Weis et al. |
| 6,395,036 B1 | 5/2002 | Czernuszka et al. |
| 6,406,498 B1 | 6/2002 | Tormala et al. |
| 6,417,166 B2 | 7/2002 | Liu |
| 6,419,708 B1 | 7/2002 | Hall et al. |
| 6,423,095 B1 | 7/2002 | Van Hoeck et al. |
| 6,425,949 B1 | 7/2002 | Lemaitre et al. |
| 6,426,332 B1 | 7/2002 | Rueger et al. |
| 6,432,919 B1 | 8/2002 | Wang et al. |
| 6,440,444 B2 | 8/2002 | Boyce et al. |
| 6,444,222 B1 | 9/2002 | Asculai et al. |
| 6,454,787 B1 | 9/2002 | Maddalo et al. |
| 6,461,630 B1 | 10/2002 | Tucker et al. |
| 6,468,308 B1 | 10/2002 | Kuberasampath et al. |
| 6,471,993 B1 | 10/2002 | Shastri et al. |
| 6,478,825 B1 | 11/2002 | Winterbottom et al. |
| 6,479,065 B2 | 11/2002 | Jaworowicz et al. |
| 6,479,565 B1 | 11/2002 | Stanley |
| 6,504,079 B2 | 1/2003 | Tucker et al. |
| 6,506,217 B1 | 1/2003 | Arnett |
| 6,511,510 B1 | 1/2003 | de Bruijn et al. |
| 6,511,958 B1 | 1/2003 | Atkinson et al. |
| 6,514,514 B1 | 2/2003 | Atkinson et al. |
| 6,521,246 B2 | 2/2003 | Sapieszko et al. |
| 6,524,345 B1 | 2/2003 | Valimaa et al. |
| 6,540,784 B2 | 4/2003 | Barlow et al. |
| 6,541,023 B1 | 4/2003 | Andre et al. |
| 6,544,290 B1 | 4/2003 | Lee et al. |
| 6,547,866 B1 | 4/2003 | Edwards et al. |
| 6,548,002 B2 | 4/2003 | Gresser et al. |
| 6,551,355 B1 | 4/2003 | Lewandrowski et al. |
| 6,551,995 B1 | 4/2003 | Oppermann et al. |
| 6,576,015 B2 | 6/2003 | Geistlich et al. |
| 6,576,249 B1 | 6/2003 | Gendler et al. |
| 6,582,471 B1 | 6/2003 | Bittmann et al. |
| 6,589,590 B2 | 7/2003 | Czernuszka et al. |
| 6,602,294 B1 | 8/2003 | Sittinger et al. |
| 6,645,250 B2 | 11/2003 | Schulter |
| 6,679,918 B1 | 1/2004 | Benedict et al. |
| 6,696,073 B2 | 2/2004 | Boyce et al. |
| 6,712,822 B2 | 3/2004 | Re et al. |
| 6,736,799 B1 | 5/2004 | Erbe et al. |
| 6,764,517 B2 | 7/2004 | Yamamoto et al. |
| 6,840,961 B2 | 1/2005 | Tofighi et al. |
| 6,846,327 B2 | 1/2005 | Khandkar et al. |
| 6,884,621 B2 | 4/2005 | Liao et al. |
| 6,899,107 B2 | 5/2005 | Lewandrowski et al. |
| 6,902,584 B2 | 6/2005 | Kwan et al. |
| 6,903,146 B2 | 6/2005 | Matsushima et al. |
| 6,911,046 B2 | 6/2005 | Schulter |
| 6,911,212 B2 | 6/2005 | Gertzman et al. |
| 6,921,412 B1 | 7/2005 | Black et al. |
| 6,933,326 B1 | 8/2005 | Griffey et al. |
| 6,953,594 B2 | 10/2005 | Lee et al. |
| 6,974,862 B2 | 12/2005 | Ringeisen et al. |
| 6,991,803 B2 | 1/2006 | Sapieszko et al. |
| 7,026,292 B1 | 4/2006 | Lee et al. |
| 7,045,141 B2 | 5/2006 | Merboth et al. |
| 7,052,517 B2 | 5/2006 | Murphy et al. |
| 7,077,866 B2 | 7/2006 | Gresser et al. |
| 7,105,182 B2 | 9/2006 | Szymaitis |
| 7,122,057 B2 | 10/2006 | Beam et al. |
| 7,132,110 B2 | 11/2006 | Kay et al. |
| 7,153,938 B2 | 12/2006 | Kikuchi et al. |
| 7,156,880 B2 | 1/2007 | Evans et al. |
| 7,163,691 B2 | 1/2007 | Knaack et al. |
| 7,163,965 B2 | 1/2007 | Sotome et al. |
| 7,166,133 B2 | 1/2007 | Evans et al. |
| 7,172,629 B2 | 2/2007 | McKay |
| 7,175,858 B2 | 2/2007 | Constantz et al. |
| 7,189,263 B2 | 3/2007 | Erbe et al. |
| 7,189,392 B1 | 3/2007 | Kim et al. |
| 7,229,545 B2 | 6/2007 | Sewing et al. |
| 7,235,107 B2 | 6/2007 | Evans et al. |
| 7,241,316 B2 | 7/2007 | Evans et al. |
| 7,250,550 B2 | 7/2007 | Overby et al. |
| 7,252,685 B2 | 8/2007 | Bindseil et al. |
| 7,252,841 B2 | 8/2007 | Constantz |
| 7,303,814 B2 | 12/2007 | Lamberti et al. |
| 7,318,840 B2 | 1/2008 | McKay |
| 7,318,841 B2 | 1/2008 | Tofighi et al. |
| 7,358,284 B2 | 4/2008 | Griffey et al. |
| 7,473,678 B2 | 1/2009 | Lynch |
| 7,485,617 B1 | 2/2009 | Pohl et al. |
| 7,494,950 B2 | 2/2009 | Armitage et al. |
| 7,498,040 B2 | 3/2009 | Masinaei et al. |
| 7,498,041 B2 | 3/2009 | Masinaei et al. |
| 7,517,539 B1 | 4/2009 | Lee et al. |
| 7,531,004 B2 | 5/2009 | Bagga et al. |
| 7,534,264 B2 | 5/2009 | Fischer |
| 7,534,451 B2 | 5/2009 | Erbe et al. |
| 7,621,963 B2 | 11/2009 | Simon et al. |
| 7,628,851 B2 | 12/2009 | Armitage et al. |
| 7,670,378 B2 | 3/2010 | Bloemer et al. |
| 7,670,384 B2 | 3/2010 | Kimar et al. |
| 7,686,239 B2 | 3/2010 | Tofighi et al. |
| 7,718,616 B2 | 5/2010 | Thorne |
| 7,722,895 B1 | 5/2010 | McKay et al. |
| 7,771,741 B2 | 8/2010 | Drapeau et al. |
| 7,776,100 B2 | 8/2010 | Brekke et al. |
| 7,780,994 B2 | 8/2010 | Lynn et al. |
| 7,785,617 B2 | 8/2010 | Shakesheff et al. |
| 7,799,767 B2 | 9/2010 | Lamberti et al. |
| 7,811,608 B2 | 10/2010 | Kay et al. |
| 7,824,702 B2 | 11/2010 | Wironen et al. |
| 7,833,278 B2 | 11/2010 | Evans et al. |
| 7,857,860 B2 | 12/2010 | Saini et al. |
| 7,887,598 B2 | 2/2011 | Evans et al. |
| 7,887,831 B2 | 2/2011 | Yayon |
| 7,892,291 B2 | 2/2011 | Evans et al. |
| 7,897,722 B2 | 3/2011 | Chung et al. |
| 7,910,690 B2 | 3/2011 | Ringeisen et al. |
| 7,951,200 B2 | 5/2011 | Heinz |
| 7,959,941 B2 | 6/2011 | Knaack et al. |
| 7,963,997 B2 | 6/2011 | Brekke et al. |
| 8,029,575 B2 | 10/2011 | Borden |
| 2001/0004225 A1 | 6/2001 | Nicholls et al. |
| 2001/0005797 A1 | 6/2001 | Barlow et al. |
| 2001/0008980 A1 | 7/2001 | Gresser et al. |
| 2001/0010023 A1 | 7/2001 | Schwartz et al. |
| 2001/0012968 A1 | 8/2001 | Preissman |
| 2001/0014662 A1 | 8/2001 | Rueger et al. |
| 2001/0014667 A1 | 8/2001 | Chen et al. |
| 2001/0014830 A1 | 8/2001 | Kwan et al. |
| 2001/0014831 A1 | 8/2001 | Scarborough |
| 2001/0016646 A1 | 8/2001 | Rueger et al. |
| 2001/0016772 A1 | 8/2001 | Lee et al. |
| 2001/0018614 A1 | 8/2001 | Bianchi |
| 2001/0018797 A1 | 9/2001 | Shepherd |
| 2001/0020476 A1 | 9/2001 | Gan et al. |
| 2001/0031799 A1 | 10/2001 | Shimp |
| 2001/0037014 A1 | 11/2001 | Liu |
| 2001/0039453 A1 | 11/2001 | Gresser et al. |
| 2001/0041792 A1 | 11/2001 | Donda et al. |

(56) References Cited

U.S. PATENT DOCUMENTS

| | | |
|---|---|---|
| 2001/0041942 A1 | 11/2001 | Ylanen et al. |
| 2001/0043940 A1 | 11/2001 | Boyce et al. |
| 2001/0044413 A1 | 11/2001 | Pierce et al. |
| 2001/0049141 A1 | 12/2001 | Fike et al. |
| 2001/0051834 A1 | 12/2001 | Frondoza et al. |
| 2001/0053937 A1 | 12/2001 | Johnson et al. |
| 2001/0055622 A1 | 12/2001 | Burrell et al. |
| 2002/0013626 A1 | 1/2002 | Geistlich et al. |
| 2002/0013627 A1 | 1/2002 | Geistlich et al. |
| 2002/0018796 A1 | 2/2002 | Wironen |
| 2002/0018797 A1 | 2/2002 | Cui et al. |
| 2002/0018798 A1 | 2/2002 | Sewing et al. |
| 2002/0022883 A1 | 2/2002 | Burg |
| 2002/0022885 A1 | 2/2002 | Ochi |
| 2002/0034532 A1 | 3/2002 | Brodbeck et al. |
| 2002/0034533 A1 | 3/2002 | Peterson et al. |
| 2002/0037309 A1 | 3/2002 | Jaworowicz et al. |
| 2002/0042657 A1 | 4/2002 | Pugh et al. |
| 2002/0045582 A1 | 4/2002 | Margolin et al. |
| 2002/0053937 A1 | 5/2002 | Lloyd |
| 2002/0054901 A1 | 5/2002 | Gainey et al. |
| 2002/0055143 A1 | 5/2002 | Bell et al. |
| 2002/0058622 A1 | 5/2002 | Igari et al. |
| 2002/0061328 A1 | 5/2002 | Gertzman et al. |
| 2002/0072804 A1 | 6/2002 | Donda |
| 2002/0076429 A1 | 6/2002 | Wironen et al. |
| 2002/0082220 A1 | 6/2002 | Hoemann et al. |
| 2002/0082594 A1 | 6/2002 | Hata et al. |
| 2002/0082694 A1 | 6/2002 | McKay |
| 2002/0082697 A1 | 6/2002 | Damien |
| 2002/0082700 A1 | 6/2002 | Bianchi et al. |
| 2002/0090725 A1 | 7/2002 | Simpson et al. |
| 2002/0098222 A1 | 7/2002 | Wironen et al. |
| 2002/0106393 A1 | 8/2002 | Bianchi et al. |
| 2002/0106394 A1 | 8/2002 | Tucker et al. |
| 2002/0114795 A1 | 8/2002 | Thorne et al. |
| 2002/0128722 A1 | 9/2002 | Jefferies |
| 2002/0192263 A1 | 12/2002 | Merboth et al. |
| 2003/0009235 A1 | 1/2003 | Manrique et al. |
| 2003/0036797 A1 | 2/2003 | Malaviya et al. |
| 2003/0143207 A1 | 7/2003 | Livesey et al. |
| 2003/0152606 A1 | 8/2003 | Gerber |
| 2003/0232071 A1 | 12/2003 | Gower et al. |
| 2003/0236573 A1 | 12/2003 | Evans et al. |
| 2004/0002558 A1 | 1/2004 | McKay |
| 2004/0062816 A1 | 4/2004 | Atkinson et al. |
| 2004/0081704 A1 | 4/2004 | Benedict et al. |
| 2004/0131562 A1 | 7/2004 | Gower et al. |
| 2004/0181232 A1 | 9/2004 | Re et al. |
| 2004/0197311 A1 | 10/2004 | Brekke et al. |
| 2004/0220680 A1 | 11/2004 | Yamamoto et al. |
| 2005/0053638 A1 | 3/2005 | Tanaka et al. |
| 2005/0079201 A1 | 4/2005 | Rathenow et al. |
| 2005/0089579 A1 | 4/2005 | Li et al. |
| 2005/0199156 A1 | 9/2005 | Khairoun et al. |
| 2005/0217538 A1 | 10/2005 | Reinstorf et al. |
| 2005/0249773 A1 | 11/2005 | Maspero et al. |
| 2005/0251266 A1 | 11/2005 | Maspero et al. |
| 2005/0261767 A1 | 11/2005 | Anderson et al. |
| 2005/0283255 A1 | 12/2005 | Geremakis et al. |
| 2005/0288795 A1 | 12/2005 | Bagga et al. |
| 2006/0030627 A1 | 2/2006 | Yamamoto et al. |
| 2006/0030948 A1 | 2/2006 | Manrique et al. |
| 2006/0039951 A1 | 2/2006 | Sapieszko et al. |
| 2006/0093670 A1 | 5/2006 | Mizushima et al. |
| 2006/0147547 A1 | 7/2006 | Yayon |
| 2006/0184131 A1 | 8/2006 | Murphy et al. |
| 2006/0204544 A1 | 9/2006 | Sunwoo et al. |
| 2006/0204580 A1 | 9/2006 | Gower et al. |
| 2006/0204581 A1 | 9/2006 | Gower et al. |
| 2006/0216321 A1 | 9/2006 | Lyu et al. |
| 2006/0233851 A1 | 10/2006 | Simon et al. |
| 2006/0246150 A1 | 11/2006 | Thorne |
| 2006/0251729 A1 | 11/2006 | Kay et al. |
| 2006/0270037 A1 | 11/2006 | Kato et al. |
| 2006/0292350 A1 | 12/2006 | Kawamura et al. |
| 2007/0003593 A1 | 1/2007 | Wironen et al. |
| 2007/0071791 A1 | 3/2007 | Fischer |
| 2007/0088437 A1 | 4/2007 | Betz et al. |
| 2007/0093912 A1 | 4/2007 | Borden |
| 2007/0128249 A1 | 6/2007 | McKay |
| 2007/0129807 A1 | 6/2007 | Lynch et al. |
| 2007/0134285 A1 | 6/2007 | Lynn et al. |
| 2007/0154563 A1 | 7/2007 | Behnam et al. |
| 2007/0178158 A1 | 8/2007 | Knaack et al. |
| 2007/0191963 A1 | 8/2007 | Winterbottom et al. |
| 2007/0202148 A1 | 8/2007 | Ringeisen et al. |
| 2007/0231788 A1 | 10/2007 | Behnam et al. |
| 2007/0233272 A1 | 10/2007 | Boyce et al. |
| 2007/0248575 A1 | 10/2007 | Connor et al. |
| 2007/0276489 A1 | 11/2007 | Bindseil et al. |
| 2008/0015692 A1 | 1/2008 | Heinz |
| 2008/0015709 A1 | 1/2008 | Evans et al. |
| 2008/0033548 A1 | 2/2008 | Xuenong et al. |
| 2008/0033572 A1* | 2/2008 | D'Antonio et al. ........ 623/23.51 |
| 2008/0063671 A1 | 3/2008 | Morris et al. |
| 2008/0065210 A1 | 3/2008 | McKay |
| 2008/0069852 A1 | 3/2008 | Shimp et al. |
| 2008/0095815 A1 | 4/2008 | Mao |
| 2008/0114458 A1 | 5/2008 | McKay |
| 2008/0124397 A1 | 5/2008 | Wironen et al. |
| 2008/0145392 A1 | 6/2008 | Knaack et al. |
| 2008/0145404 A1 | 6/2008 | Hill et al. |
| 2008/0147065 A1 | 6/2008 | McKay et al. |
| 2008/0147197 A1 | 6/2008 | McKay |
| 2008/0152687 A1 | 6/2008 | Thorne |
| 2008/0188945 A1 | 8/2008 | Boyce et al. |
| 2008/0188946 A1* | 8/2008 | Rosenberg et al. ........ 623/23.63 |
| 2008/0199508 A1 | 8/2008 | Lamberti et al. |
| 2008/0233203 A1 | 9/2008 | Woodell-May et al. |
| 2008/0241211 A1 | 10/2008 | Han |
| 2008/0249637 A1 | 10/2008 | Asgari et al. |
| 2008/0262613 A1 | 10/2008 | Gogolewski |
| 2008/0293617 A1 | 11/2008 | Benedict et al. |
| 2008/0317817 A1 | 12/2008 | Fischer |
| 2009/0012625 A1 | 1/2009 | Ying et al. |
| 2009/0017093 A1 | 1/2009 | Springer et al. |
| 2009/0123547 A1 | 5/2009 | Hill et al. |
| 2009/0124552 A1 | 5/2009 | Hill et al. |
| 2009/0142385 A1 | 6/2009 | Gross et al. |
| 2009/0148495 A1 | 6/2009 | Hammer et al. |
| 2009/0155366 A1 | 6/2009 | Pohl et al. |
| 2009/0157182 A1 | 6/2009 | Koblish et al. |
| 2009/0246244 A1 | 10/2009 | McKay et al. |
| 2009/0254104 A1 | 10/2009 | Murray |
| 2009/0269388 A1 | 10/2009 | Sunwoo et al. |
| 2009/0292359 A1 | 11/2009 | Borden |
| 2009/0292360 A1 | 11/2009 | Borden |
| 2009/0292367 A1 | 11/2009 | Borden |
| 2009/0324675 A1 | 12/2009 | Gunatillake et al. |
| 2010/0004733 A1 | 1/2010 | Atanasoska et al. |
| 2010/0015230 A1 | 1/2010 | Ron |
| 2010/0021520 A1 | 1/2010 | Baskin et al. |
| 2010/0036503 A1 | 2/2010 | Chen et al. |
| 2010/0048763 A1 | 2/2010 | Armitage et al. |
| 2010/0049322 A1 | 2/2010 | McKay |
| 2010/0049330 A1 | 2/2010 | Horvath |
| 2010/0082072 A1 | 4/2010 | Sybert et al. |
| 2010/0098673 A1 | 4/2010 | D'Antonio et al. |
| 2010/0131074 A1 | 5/2010 | Shikinami |
| 2010/0168869 A1 | 7/2010 | Long et al. |
| 2010/0196489 A1 | 8/2010 | Thorne |
| 2010/0209408 A1 | 8/2010 | Livesey |
| 2010/0209470 A1 | 8/2010 | Mohan et al. |
| 2010/0226961 A1 | 9/2010 | Lamberti et al. |
| 2010/0255115 A1 | 10/2010 | Mohan et al. |
| 2010/0266658 A1 | 10/2010 | McKay et al. |
| 2010/0266660 A1 | 10/2010 | McKay et al. |
| 2010/0268227 A1 | 10/2010 | Tong et al. |
| 2011/0045044 A1 | 2/2011 | Masinaei et al. |
| 2011/0133368 A1 | 6/2011 | Ringeisen et al. |
| 2011/0140137 A1 | 6/2011 | Lai |

(56) References Cited

U.S. PATENT DOCUMENTS

| | | | |
|---|---|---|---|
| 2011/0144767 A1 | 6/2011 | Evans et al. | |
| 2011/0165199 A1 | 7/2011 | Thorne et al. | |
| 2011/0183936 A1 | 7/2011 | Bailleul | |

FOREIGN PATENT DOCUMENTS

| | | | |
|---|---|---|---|
| CA | 2133253 A1 | 3/1996 | |
| CA | 2446840 A1 | 4/2002 | |
| CA | 2280966 C | 4/2012 | |
| CA | 2280966 C | 4/2012 | |
| EP | 0164483 A1 | 12/1985 | |
| EP | 0171176 A2 | 2/1986 | |
| EP | 0197693 A2 | 10/1986 | |
| EP | 0233770 A2 | 8/1987 | |
| EP | 0243178 A2 | 10/1987 | |
| EP | 0271668 A1 | 6/1988 | |
| EP | 289562 A1 | 11/1988 | |
| EP | 309241 A2 | 3/1989 | |
| EP | 321277 A2 | 6/1989 | |
| EP | 0349048 A2 | 1/1990 | |
| EP | 0361896 A2 | 4/1990 | |
| EP | 0243178 B1 | 6/1991 | |
| EP | 0197693 B1 | 10/1991 | |
| EP | 271668 B1 | 12/1991 | |
| EP | 321277 B1 | 3/1992 | |
| EP | 0522569 A1 | 1/1993 | |
| EP | 522569 A1 | 1/1993 | |
| EP | 289562 B1 | 2/1993 | |
| EP | 0270254 B1 | 3/1993 | |
| EP | 0558727 A1 | 9/1993 | |
| EP | 0567391 A1 | 10/1993 | |
| EP | 0309241 B1 | 12/1993 | |
| EP | 309241 B1 | 12/1993 | |
| EP | 573491 A1 | 12/1993 | |
| EP | 0446262 B1 | 3/1994 | |
| EP | 0588727 A1 | 3/1994 | |
| EP | 0605799 A1 | 7/1994 | |
| EP | 0605933 B1 | 7/1994 | |
| EP | 608313 A1 | 8/1994 | |
| EP | 0616814 A1 | 9/1994 | |
| EP | 0621044 A2 | 10/1994 | |
| EP | 0668478 B1 | 10/1994 | |
| EP | 0623031 A1 | 11/1994 | |
| EP | 0439689 B1 | 12/1994 | |
| EP | 627899 A1 | 12/1994 | |
| EP | 0674908 A1 | 10/1995 | |
| EP | 0719529 A1 | 7/1996 | |
| EP | 0429438 B1 | 8/1996 | |
| EP | 732947 A1 | 9/1996 | |
| EP | 0747067 A2 | 12/1996 | |
| EP | 0754699 A1 | 1/1997 | |
| EP | 855884 B1 | 4/1997 | |
| EP | 828453 A1 | 3/1998 | |
| EP | 837701 A1 | 4/1998 | |
| EP | 855884 A1 | 8/1998 | |
| EP | 0588727 B1 | 11/1998 | |
| EP | 0901795 A2 | 3/1999 | |
| EP | 0605799 B1 | 4/1999 | |
| EP | 0932373 A1 | 8/1999 | |
| EP | 1795214 A2 | 8/1999 | |
| EP | 608313 B1 | 2/2000 | |
| EP | 0623031 B1 | 2/2000 | |
| EP | 0987031 A1 | 3/2000 | |
| EP | 1019027 A1 | 7/2000 | |
| EP | 1053739 A1 | 11/2000 | |
| EP | 1120439 A1 | 8/2001 | |
| EP | 1127581 A1 | 8/2001 | |
| EP | 627899 B1 | 11/2001 | |
| EP | 1150659 | 11/2001 | |
| EP | 1150725 A1 | 11/2001 | |
| EP | 1150726 A1 | 11/2001 | |
| EP | 1178769 A1 | 2/2002 | |
| EP | 1180986 A2 | 2/2002 | |
| EP | 732947 B1 | 3/2002 | |
| EP | 573491 B1 | 4/2002 | |
| EP | 1224925 A2 | 7/2002 | |
| EP | 1233714 A1 | 8/2002 | |
| EP | 1234587 A1 | 8/2002 | |
| EP | 0719529 B1 | 9/2002 | |
| EP | 837701 B1 | 2/2003 | |
| EP | 0987031 B1 | 4/2003 | |
| EP | 1434608 A2 | 4/2003 | |
| EP | 1150726 B1 | 11/2003 | |
| EP | 1019027 A4 | 5/2004 | |
| EP | 1416977 A2 | 5/2004 | |
| EP | 1419791 A1 | 5/2004 | |
| EP | 0855884 B1 | 6/2004 | |
| EP | 1120439 B1 | 6/2004 | |
| EP | 1425024 A2 | 6/2004 | |
| EP | 1437148 A1 | 7/2004 | |
| EP | 1462126 A1 | 9/2004 | |
| EP | 1476202 A1 | 11/2004 | |
| EP | 1476204 A1 | 11/2004 | |
| EP | 1482872 A1 | 12/2004 | |
| EP | 1500405 A1 | 1/2005 | |
| EP | 1677846 | 5/2005 | |
| EP | 1150725 B1 | 6/2005 | |
| EP | 1545466 A1 | 6/2005 | |
| EP | 1701672 | 7/2005 | |
| EP | 1701729 | 7/2005 | |
| EP | 1561480 A2 | 8/2005 | |
| EP | 1708651 A1 | 8/2005 | |
| EP | 1727489 A2 | 8/2005 | |
| EP | 828453 B1 | 11/2005 | |
| EP | 1234587 B1 | 11/2005 | |
| EP | 1608414 A2 | 12/2005 | |
| EP | 1623681 A1 | 2/2006 | |
| EP | 1638486 A2 | 3/2006 | |
| EP | 1642599 A1 | 4/2006 | |
| EP | 1648347 | 4/2006 | |
| EP | 1178769 B1 | 7/2006 | |
| EP | 1712244 A1 | 10/2006 | |
| EP | 1727489 B1 | 12/2006 | |
| EP | 1753474 A2 | 2/2007 | |
| EP | 1771490 A1 | 4/2007 | |
| EP | 1940313 | 5/2007 | |
| EP | 1976459 | 7/2007 | |
| EP | 1976460 | 7/2007 | |
| EP | 1839622 A2 | 10/2007 | |
| EP | 1844798 A1 | 10/2007 | |
| EP | 2007196 | 11/2007 | |
| EP | 1925325 A1 | 5/2008 | |
| EP | 1608414 B1 | 7/2008 | |
| EP | 2125055 | 9/2008 | |
| EP | 1476204 B1 | 10/2008 | |
| EP | 2139500 | 10/2008 | |
| EP | 1476202 B1 | 1/2009 | |
| EP | 2049591 A1 | 4/2009 | |
| EP | 2070491 A2 | 6/2009 | |
| EP | 2104518 A2 | 9/2009 | |
| EP | 1464345 B1 | 12/2009 | |
| EP | 2129318 A2 | 12/2009 | |
| EP | 1419791 B1 | 2/2010 | |
| EP | 1416977 B1 | 7/2010 | |
| EP | 2260790 A2 | 12/2010 | |
| EP | 1233714 B1 | 2/2012 | |
| GB | 1224925 A | 3/1971 | |
| GB | 2164042 A | 3/1986 | |
| GB | 2377642 A | 1/2003 | |
| JP | 61226055 A | 10/1986 | |
| JP | 61226055 A | 10/1986 | |
| JP | 63066106 A | 3/1988 | |
| JP | 1076861 A | 3/1989 | |
| JP | 64076861 | 3/1989 | |
| JP | 01121059 A | 5/1989 | |
| JP | 1121059 A | 5/1989 | |
| JP | 1250264 A | 10/1989 | |
| JP | 2100410 A | 4/1994 | |
| JP | 06100410 | 4/1994 | |
| JP | 8505548 A | 6/1996 | |
| JP | 9505305 | 5/1997 | |
| JP | 11164880 A | 6/1999 | |
| JP | 11506727 A | 6/1999 | |

(56) References Cited

FOREIGN PATENT DOCUMENTS

| | | |
|---|---|---|
| JP | 11506727 A | 6/1999 |
| JP | 11313882 A | 11/1999 |
| JP | 11313882 A | 11/1999 |
| JP | 11313883 A | 11/1999 |
| JP | 11313883 A | 11/1999 |
| JP | 2000262608 A | 9/2000 |
| JP | 2002501786 A | 1/2002 |
| JP | 2002501786 A | 1/2002 |
| JP | 2004520106 A | 7/2004 |
| JP | 2004520106 A | 7/2004 |
| JP | 5105216 | 10/2012 |
| JP | 5105216 A | 10/2012 |
| WO | WO-8707495 A1 | 12/1987 |
| WO | WO-8904646 A1 | 6/1989 |
| WO | WO-9000862 A1 | 2/1990 |
| WO | WO-9200109 A1 | 1/1992 |
| WO | WO-9209697 A1 | 6/1992 |
| WO | WO-9305823 A1 | 4/1993 |
| WO | WO-9312736 A1 | 7/1993 |
| WO | WO-9313815 A1 | 7/1993 |
| WO | WO-9316739 A1 | 9/1993 |
| WO | WO-9320827 A1 | 10/1993 |
| WO | WO-9402412 A1 | 2/1994 |
| WO | WO-9415653 A1 | 7/1994 |
| WO | WO-9420064 A1 | 9/1994 |
| WO | WO-9525550 A1 | 9/1995 |
| WO | WO-9610374 A1 | 4/1996 |
| WO | WO-9610428 A1 | 4/1996 |
| WO | WO-9639203 A1 | 12/1996 |
| WO | WO-9640297 A1 | 12/1996 |
| WO | WO-9817330 A1 | 4/1998 |
| WO | WO-9830141 A2 | 7/1998 |
| WO | WO-9835653 A1 | 8/1998 |
| WO | WO-9840113 A1 | 9/1998 |
| WO | WO-9851354 A2 | 11/1998 |
| WO | WO-9858602 A1 | 12/1998 |
| WO | WO-9915211 A1 | 4/1999 |
| WO | WO-9919003 A1 | 4/1999 |
| WO | WO-0004940 A1 | 2/2000 |
| WO | WO-0032251 A1 | 6/2000 |
| WO | WO-0045870 A1 | 8/2000 |
| WO | WO-0045871 A1 | 8/2000 |
| WO | WO-0047114 A1 | 8/2000 |
| WO | WO-0071178 A1 | 11/2000 |
| WO | WO-0074690 A1 | 12/2000 |
| WO | WO-0130409 A1 | 5/2001 |
| WO | WO-0132072 A2 | 5/2001 |
| WO | WO-0141821 A1 | 6/2001 |
| WO | WO-0141822 A1 | 6/2001 |
| WO | WO-0166044 A2 | 9/2001 |
| WO | WO-0174410 A1 | 10/2001 |
| WO | WO-0207961 A1 | 1/2002 |
| WO | WO-0211781 A1 | 2/2002 |
| WO | WO-0221222 A1 | 3/2002 |
| WO | WO-0222045 A1 | 3/2002 |
| WO | WO-0224107 A2 | 3/2002 |
| WO | WO-0234113 A2 | 5/2002 |
| WO | WO-0234116 A2 | 5/2002 |
| WO | WO-0240073 A1 | 5/2002 |
| WO | WO-0240963 A2 | 5/2002 |
| WO | WO-02051449 A2 | 7/2002 |
| WO | WO-02051449 A3 | 7/2002 |
| WO | WO-02070029 A2 | 9/2002 |
| WO | WO-03071991 A1 | 9/2003 |
| WO | WO-03092759 A1 | 11/2003 |
| WO | WO-2004078120 A2 | 9/2004 |
| WO | WO-2004091435 A2 | 10/2004 |
| WO | WO-2004103422 A1 | 12/2004 |
| WO | WO-2005004755 A1 | 1/2005 |
| WO | WO-2005051447 A1 | 6/2005 |
| WO | WO-2005074614 A2 | 8/2005 |
| WO | WO-2005081699 A2 | 9/2005 |
| WO | WO-2005099785 A1 | 10/2005 |
| WO | WO-2006031196 A1 | 3/2006 |
| WO | WO-2006092718 A2 | 9/2006 |
| WO | WO-2007053520 A2 | 5/2007 |
| WO | WO-2008019024 A2 | 2/2008 |
| WO | WO-2008076604 A1 | 6/2008 |
| WO | WO-2009052967 A1 | 4/2009 |
| WO | WO-2010117766 A1 | 10/2010 |
| WO | WO-2010119476 A2 | 10/2010 |
| WO | WO-2010134102 A1 | 11/2010 |
| WO | WO-2012068135 A1 | 5/2012 |
| WO | WO-2012068135 A1 | 5/2012 |

OTHER PUBLICATIONS

"U.S. Appl. No. 12/748,999 , Response filed Mar. 1, 2012 to Final Office Action mailed Nov. 1, 2011", 6 pgs.

"U.S. Appl. No. 12/748,999, Final Office Action mailed Nov. 1, 2011", 7 pgs.

"U.S. Appl. No. 12/748,999, Non-Final Office Action mailed Feb. 28, 2011", 9 pgs.

"U.S. Appl. No. 12/748,999, Preliminary Amendment filed Mar. 29, 2010", 3 pgs.

"U.S. Appl. No. 12/748,999, Response filed Feb. 14, 2011 to Restriction Requirement mailed Jan. 14, 2011", 6 pgs.

"U.S. Appl. No. 12/748,999, Response filed Aug. 29, 2011 to Non Final Office Action mailed Feb. 28, 2011", 8 pgs.

"U.S. Appl. No. 12/748,999, Restriction Requirement mailed Jan. 14, 2011", 8 pgs.

"U.S. Appl. No. 12/849,414, Non Final Office Action mailed Sep. 23, 2011", 17 pgs.

"U.S. Appl. No. 12/849,414, Preliminary Amendment filed Aug. 3, 2010", 7 pgs.

"Australian Application Serial No. 2007334213, Office Action mailed Jan. 9, 2012", 2 pgs.

"Canadian Application Serial No. 2,280,966, Office Action Oct. 3, 2007", 2 pgs.

"Canadian Application Serial No. 2,280,966, Office Action mailed Apr. 27, 2011", 2 Pgs.

"Canadian Application Serial No. 2,280,966, Office Action mailed Jul. 30, 2006", 2 pgs.

"Canadian Application Serial No. 2,280,966, Office Action mailed Nov. 9, 2009", 3 pgs.

"Canadian Application Serial No. 2,280,966, Office Action Response filed Nov. 9, 2011", 4 pgs.

"Canadian Application Serial No. 2,280,966, Response filed Jan. 29, 2007 to Office Action mailed Jul. 31, 2006 ", 7 pgs.

"Canadian Application Serial No. 2,280,966, Response filed Mar. 28, 2008 to Office Action mailed Oct. 3, 2007", 12 pgs.

"Canadian Application Seial No. 2,280,966, Response filed May 5, 2010 to Office Action mailed Nov. 9, 2009", 5 pgs.

"Canadian Application Serial No. 2,446,840, Office Action mailed Jul. 27, 2011", 3 pgs.

"Characterization of Osteoinductive Potential", Orthovita Products, http://www.orthovita.com/products/vitoss/osteoinductive.html, (Jan. 2004), 3 pgs.

"Chondrogenesis and Osteogenesis: Growth Factors", Abstract No's. 917-921, 162a.

"Collagraft bone Graft Matrix (Contraindications)", Distributed by Zimmer, Inc., Warsaw, Indiana, (Sep. 1992), 1 pg.

"Collagraft Bone Graft Matrix (Indications)", Distributed by Zimmer, Inc., Warsaw, Indiana, (Sep. 1992), 1 pg.

"Collagraft Bone Graft Matrix (Nonosteoinductive Bone Void Filler)", Distributed by Zimmer, Inc., Warsaw, Indiana, (Sep. 1992), 1 pg.

"Collagraft Bone Graft Matriz Strip", Distributed by Zimmer, Inc., Warsaw, Indiana, (Feb. 1994), 6 pgs.

"U.S. Appl. No. 12/180,035, Examiner Interview Summary mailed Mar. 14, 2012", 3 pgs.

"U.S. Appl. No. 12/180,035, Response filed Mar. 20, 2012 to Final Office Action mailed Sep. 27, 2011", 9 pgs.

"U.S. Appl. No. 12/849,414 , Response filed Mar. 23, 2012 to Non Final Office Action mailed Sep. 23, 2011", 8 pgs.

"Australian Application Serial No. 2007334213, Response filed Apr. 19, 2012 to First Examiners Report mailed Jan. 8, 2012", 9 pgs.

"Japanese Application Serial No. 1998535914, Office Action Mailed Jan. 24, 2012", W/ English Translation, 24 Pgs.

(56) References Cited

OTHER PUBLICATIONS

Cheung, D. T, et al., "The effect of gamma-irradiation on collagen molecules, isolated alpha-chains, and crosslinked native fibers.", J Biomed Mater Res., 24(5), (May 1990), 581-9.

Chu, C. C, et al., "The effect of gamma irradiation on the enzymatic degradation of polyglycolic acid absorbable sutures", J Biomed Mater Res., 17(6), (Nov. 1983), 1029-40.

Hallfeldt, K. K, et al., "Sterilization of partially demineralized bone matrix: the effects of different sterilization techniques on osteogenetic properties", J Surg Res., 59(5), (Nov. 1995), 614-20.

Hamada, K., et al., "Hydrothermal modification of titanium surface in calcium solutions", Biomaterials, 23, (2002), 2265-2272.

Ho, Hsiu-O, et al., "Characterization of collagen isolation and application of collagen gel as a drug carrier", Journal of Controlled Release, 44, (1997), 103-112.

Ijiri, S., et al., "Effect of sterilization on bone morphogenetic protein", J Orthop Res., 12(5), (Sep. 1994), 628-36.

Katz, R. W, et al., "Radiation-sterilized insoluble collagenous bone matrix is a functional carrier of osteogenin for bone induction", Calcif Tissue Int., 47(3), (Sep. 1990), 183-5.

Kim, H. M, et al., "Effect of heat treatment on apatite-forming ability of Ti metal induced by alkali treatment", J Mater Sci Mater Med., 8(6), (Jun. 1997), 341-7.

Lee, K. Y, et al., "Preparation of Caclium Phosphate Paste Composites with Demineralized Bone Matrix", Key Engineering Materials, (vols. 330-332), (2007), 803-806.

Legeros, Racquel Zapanta, "Calcium Phosphate-Based Osteoinductive Materials", Chem. Rev., 108, (2008), 4742-4753.

Liu, B., et al., "The effect of gamma irradiation on injectable human amnion collagen", J Biomed Mater Res., 23(8), (Aug. 1989), 833-44.

Munting, E., et al., "Effect of sterilization on osteoinduction. Comparison of five methods in demineralized rat bone", Acta Orthop Scand., 59(1), (Feb. 1988), 34-8.

Puolakkainen, "The effect of sterilization on transforming growth factor beta isolated from demineralized human bone", Transfusion, 33(8), (Aug. 1993), 679-85.

Raptopoulou-Gigi, M., et al., "Antimicrobial proteins in sterilised human milk", Br Med J., 1(6052), (Jan. 1, 1977), 12-4.

Reid, B. D, et al., "Gamma processing technology: an alternative technology for terminal sterilization of parenterals", PDA J Pharm Sci Technol., 49(2), (Mar.-Apr. 1995), 83-9.

Schwarz, N., et al., "Irradiation-sterilization of rat bone matrix gelatin", Acta Orthop Scand., 59(2), (Apr. 1988), 165-7.

Soboleva, N. N, et al., "Radiation resistivity of frozen insulin solutions and suspensions", Int J Appl Radiat Isot., 32(10), (Oct. 1981), 753-6.

Su, D., et al., "Sterilization of collagen matrix containing protein growth factors using gamma and electron beam irradiation", Pharmaceutical Research, 12(9), Abstract BIOTECH 2035, (1995), S-87.

Tezcaner, A., et al., "Fundamentals of tissue engineering: Tissues and applications", Technology and Health Care, 10, (2002), 203-216.

Tofighi, A., "Calcium Phosphate Cement (CPC): A Critical Development Path", Key Engineering Materials, (vols. 361-363), (2008), 303-306.

Wientroub, S., et al., "Influence of irradiation on the osteoinductive potential of demineralized bone matrix", Calcif. Tissue Int., 42(4), (Apr. 1988), 255-60.

"U.S. Appl. No. 12/180,035, Non Final Office Action mailed Nov. 28, 2012", 9 pgs.

"U.S. Appl. No. 12/849,414 , Response filed Nov. 1, 2012 to Final Office Action mailed Aug. 1, 2012", 8 pgs.

"U.S. Appl. No. 12/849,414, Final Office Action mailed Aug. 1, 2012", 20 pgs.

"Canadian Application Serial No. 2,673,337, Office Action mailed Sep. 9, 2012", 3 pgs.

"Fundamentals of Bone Physiology", Therics, (Jul. 2006), 5 pgs.

"Japanese Application Serial No. 1998535914, Response filed Jul. 24, 2012 to Office Action mailed Jan. 24, 2012", (w/ English Translation of Claims), 16 pgs.

"Japanese Application Serial No. 2009-543018, Office Action mailed Dec. 4, 2012", (w/ English Translation), 5 pgs.

"The Organization of Skeletal Tissues", The Architecture and Cellular Elements of Bone, (Oct. 2000), 4 pgs.

"Tri-Calcium Phosphates as a Biomaterial", [Online]. Retrieved from the Internet: <URL: http://www.scribd.com/doc/56970573/Tri-Calcium-Phosphates-as-a-Biomaterial>, (Upload Date: Jun. 2, 2011), 5 pgs.

Chakkalakal, D A, et al., "Mineralization and pH relationships in healing skeletal defects grafted with demineralized bone matrix", Journal of Biomedical Materials Research vol. 28,, (1994), 1439-1443.

Donlon, William, "Immune Neutrality of Calf Skin Collagen Gel Used to Stimulate Revitalization in Pulpless Open Apex Teeth of Rhesus Monkeys", J Dent Res, (Jun. 1977), 670-673.

Kohles, S S, et al., "A Morphometric Evaluation of Allograft Matrix Combinations in the Treatment of Osseous Defects in a Baboon Model", Calcif. Tissue Int. 67, (2000), 156-162.

Legeros, R Z, et al., "In Vitro Formation of Dicalcium Phosphate Dihydrate, $CaHPO_4.2h_2o$ (DCPD)", Scanning Electron Micropscopy, (1983), 407-418.

Legeros, R Z, et al., "The Nature of the Calcified Material Induced by Collagen-Calcium Phosphate Gel in Tooth", Dental Research vol. 57, Special Issue A, Abstract only. Abstract No. 527, (Jan. 1978), 206.

Legeros, Racquel Z, "Biodegradation and Bioresorption of Calcium Phosphate Ceramics", Clinical Materials 14, (1993), 65-88.

Legeros, Raquel Zapanta, "Apatites in Biological Systems", Prog. Crystal Growth Charact. vol. 4, (1981), 1-45.

Lenart, G, et al., "Some Basic Problems in the Examination of the Calcium Hydrogen Phosphates of Bone", Clinical Orthopaedics and Related Research, (1972), 263-272.

Nancollas, G H, et al., "Seeded Growth of Calcium Phosphates: Effect of Different Calcium Phosphate Seed Material", J. Dent. Res. vol. 55, No. 4, (1976), 617-624.

Nevins, Alan, et al., "Hard Tissue Induction Into Pulpless Open-Apex Teeth Using Collagen-Calcium Phosphate Gel", Journal of Endodontics vol. 3, Iss. 11, (1977), 431-433.

Nevins, Alan, et al., "Revitalization of pulpless open apex teeth in rhesus monkeys, using collagen-calcium phosphate gel", J Endod. 2(6), (1976), 159-65.

Roufosse, A. H, "Indentification of Burshite in Newly Deposited Bone Mineral from Embryonic Chicks", Journal of Ultrastructure Research 68, (1979), 235-255.

Tenhuisen, Kevor S, et al., "Formation and properties of a synthetic bone composite: Hydroxyapatite-collagen", Journal of Biomedical Materials Research vol. 29, (1995), 803-810.

Walsh, W R, et al., "Demineralized bone Matrix as a template for mineral-organic composites", Biomaterials 16, (1995), 1363-1371.

"U.S. Appl. No. 12/180,035, Response filed Feb. 28, 2013 to Non Final Office Action mailed Nov. 28, 2012", 6 pgs.

"Canadian Application Serial No. 2,673,337, Response filed Feb. 7, 2013 to Office Action mailed Aug. 9, 2012", 7 pgs.

Landesman, Richard, et al., "In Vivo Analysis of the Half-Life of the Osteoinductive Potential of Demineralized Bone Matrix Using Diffusion Chambers", Calcif Tissue Int. vol. 45, (1989), 348-353.

Pappalardo, S, et al., "How to biomaterials affect the biological activities and responses of cells? An in-vitro study", Minerva Stomatol vol. 59, (2010), 445-464.

Urist, Marshall R, et al., "Preservation and Biodegration of the Morphogenetic Property of Bone Matrix", J. theor. Biol. vol. 38, (1973), 155-167.

"U.S. Appl. No. 09/023,617, Advisory Action mailed Apr. 23, 2002", 3 pgs.

"U.S. Appl. No. 09/023,617, Final Office Action mailed Nov. 23, 2001", 5 pgs.

"U.S. Appl. No. 09/023,617, Non Final Office Action mailed Apr. 24, 2001", 6 pgs.

"U.S. Appl. No. 09/023,617, Notice of Allowance mailed Sep. 15, 2003", 6 pgs.

"U.S. Appl. No. 09/023,617, Response filed Mar. 20, 2002 to Final Office Action mailed Nov. 23, 2001", 6 pgs.

"U.S. Appl. No. 09/023,617, Response filed Jun. 21, 2000 to Restriction Requirement mailed Jun. 15, 2000", 2 pgs.

(56) References Cited

OTHER PUBLICATIONS

"U.S. Appl. No. 09/023,617, Response filed Jul. 26, 1999 to Restriction Requirement mailed Jun. 24, 1999", 2 pgs.
"U.S. Appl. No. 09/023,617, Response filed Aug. 24, 2001 to Non Final Office Action mailed Apr. 24, 2001", 6 pgs.
"U.S. Appl. No. 09/023,617, Restriction Requirement mailed Jun. 15, 2000", 6 pgs.
"U.S. Appl. No. 09/023,617, Restriction Requirement mailed Jun. 24, 1999", 5 pgs.
"U.S. Appl. No. 09/746,921, Advisory Action mailed Nov. 8, 2005", 3 pgs.
"U.S. Appl. No. 09/746,921, Examiner Interview Summary mailed Apr. 1, 2002", 1 pg.
"U.S. Appl. No. 09/746,921, Final Office Action mailed Feb. 9, 2007", 14 pgs.
"U.S. Appl. No. 09/746,921, Final Office Action mailed Feb. 25, 2003", 14 pgs.
"U.S. Appl. No. 09/746,921, Final Office Action mailed Jul. 27, 2005", 10 pgs.
"U.S. Appl. No. 09/746,921, Final Office Action mailed Dec. 2, 2004", 12 pgs.
"U.S. Appl. No. 09/746,921, Non Final Office Action mailed Feb. 27, 2006", 7 pgs.
"U.S. Appl. No. 09/746,921, Non Final Office Action mailed Jul. 16, 2002", 13 pgs.
"U.S. Appl. No. 09/746,921, Non Final Office Action mailed Jul. 31, 2006", 10 pgs.
"U.S. Appl. No. 09/746,921, Non Final Office Action mailed Nov. 18, 2003", 15 pgs.
"U.S. Appl. No. 09/746,921, Response filed Feb. 1, 2002 to Restriction Requirement mailed Nov. 1, 2001", 2 pgs.
"U.S. Appl. No. 09/746,921, Response filed May 9, 2006 to Non Final Office Action mailed Feb. 27, 2006", 6 pgs.
"U.S. Appl. No. 09/746,921, Response filed May 11, 2005 to Final Office Action mailed Dec. 2, 2004", 12 pgs.
"U.S. Appl. No. 09/746,921, Response filed May 18, 2004 to Non Final Office Action mailed Nov. 18, 2003", 15 pgs.
"U.S. Appl. No. 09/746,921, Response filed Aug. 25, 2003 to Final Office Action mailed Feb. 25, 2003", 11 pgs.
"U.S. Appl. No. 09/746,921, Response filed Sep. 13, 2004 to Restriction Requirement mailed Aug. 13, 2004", 3 pgs.
"U.S. Appl. No. 09/746,921, Response filed Oct. 17, 2005 to Final Office Action mailed Jul. 27, 2005", 9 pgs.
"U.S. Appl. No. 09/746,921, Response filed Nov. 20, 2006 to Non Final Office Action mailed Jul. 31, 2006", 6 pgs.
"U.S. Appl. No. 09/746,921, Response filed Nov. 25, 2011 to Non Final Office Action mailed Jul. 16, 2002", 9 pgs.
"U.S. Appl. No. 09/746,921, Restriction Requirement mailed Aug. 13, 2004", 6 pgs.
"U.S. Appl. No. 09/746,921, Restriction Requirement mailed Nov. 1, 2001", 5 pgs.
"U.S. Appl. No. 10/739,492, Advisory Action mailed Feb. 5, 2008", 3 pgs.
"U.S. Appl. No. 10/739,492, Final Office Action mailed Oct. 5, 2007", 6 pgs.
"U.S. Appl. No. 10/739,492, Non Final Office Action mailed May 28, 2008", 11 pgs.
"U.S. Appl. No. 10/739,492, Non Final Office Action mailed Oct. 12, 2006", 7 pgs.
"U.S. Appl. No. 10/739,492, Response filed Jan. 10, 2007 to Non Final Office Action mailed Oct. 12, 2006", 4 pgs.
"U.S. Appl. No. 10/739,492, Response filed Jul. 11, 2006 to Restriction Requirement mailed Jul. 3, 2006", 2 pgs.
"U.S. Appl. No. 10/739,492, Response filed Dec. 10, 2007 to Final Office Action mailed Oct. 5, 2007", 7 pgs.
"U.S. Appl. No. 10/739,492, Restriction Requirement mailed Jul. 3, 2006", 7 pgs.
"U.S. Appl. No. 11/383,309, Advisory Action mailed Dec. 15, 2008", 3 pgs.
"U.S. Appl. No. 11/383,309, Appeal Brief filed Sep. 11, 2009", 42 pgs.
"U.S. Appl. No. 11/383,309, Appeal Brief filed Nov. 5, 2009", 14 pgs.
"U.S. Appl. No. 11/383,309, Final Office Action mailed Aug. 18, 2008", 10 pgs.
"U.S. Appl. No. 11/383,309, Non Final Office Action mailed Feb. 3, 2010", 21 pgs.
"U.S. Appl. No. 11/383,309, Non Final Office Action mailed Mar. 31, 2008", 11 pgs.
"U.S. Appl. No. 11/383,309, Non Final Office Action mailed Apr. 13, 2009", 16 pgs.
"U.S. Appl. No. 11/383,309, Response filed Jan. 21, 2009 to Advisory Action mailed Dec. 15, 2008", 14 pgs.
"U.S. Appl. No. 11/383,309, Response filed Jan. 22, 2008 to Restriction Requirement mailed Jan. 10, 2008", 3 pgs.
"U.S. Appl. No. 11/383,309, Response filed May 6, 2008 to Non Final Office Action mailed Mar. 31, 2008", 12 pgs.
"U.S. Appl. No. 11/383,309, Response filed Nov. 18, 2008 to Final Office Action mailed Aug. 18, 2008", 13 pgs.
"U.S. Appl. No. 11/383,309, Restriction Requirement mailed Jan. 10, 2008", 13 pgs.
"U.S. Appl. No. 11/614,422, Final Office Action mailed Mar. 24, 2009", 8 pgs.
"U.S. Appl. No. 11/614,422, Non Final Office Action mailed Apr. 16, 2008", 6 pgs.
"U.S. Appl. No. 11/614,422, Non Final Office Action mailed Jun. 29, 2009", 6 pgs.
"U.S. Appl. No. 11/614,422, Non Final Office Action mailed Sep. 11, 2008", 8 pgs.
"U.S. Appl. No. 11/614,422, Notice of Allowance mailed Dec. 30, 2009", 7 pgs.
"U.S. Appl. No. 11/614,422, Response filed Jan. 9, 2009", 9 pgs.
"U.S. Appl. No. 11/614,422, Response filed Feb. 5, 2008 to Restriction Requirement mailed Jan. 23, 2008", 2 pgs.
"U.S. Appl. No. 11/614,422, Response filed May 12, 2008 to Non Final Office Action mailed Apr. 16, 2008", 15 pgs.
"U.S. Appl. No. 11/614,422, Response filed Jun. 18, 2009 to Final Office Action mailed Mar. 24, 2009", 7 pgs.
"U.S. Appl. No. 11/614,422, Response filed Aug. 25, 2009 to Non Final Office Action mailed Jun. 29, 2009", 7 pgs.
"U.S. Appl. No. 11/614,422, Restriction Requirement mailed Jan. 23, 2008", 9 pgs.
"U.S. Appl. No. 12/180,035, Advisory Action mailed Jan. 24, 2012", 4 pgs.
"U.S. Appl. No. 12/180,035, Advisory Action mailed Mar. 12, 2010", 4 pgs.
"U.S. Appl. No. 12/180,035, Examiner Interview Summary mailed Sep. 27, 2011", 2 pgs.
"U.S. Appl. No. 12/180,035, Final Office Action mailed Sep. 27, 2011", 8 pgs.
"U.S. Appl. No. 12/180,035, Final Office Action mailed Nov. 16, 2009", 12 pgs.
"U.S. Appl. No. 12/180,035, Non Final Office Action mailed Dec. 27, 2010", 14 pgs.
"U.S. Appl. No. 12/180,035, Non Final Office Action mailed Apr. 16, 2009", 10 pgs.
"U.S. Appl. No. 12/180,035, Non Final Office Action mailed Jun. 10, 2010", 13 pgs.
"U.S. Appl. No. 12/180,035, Preliminary Amendment mailed Jul. 25, 2008", 5 pgs.
"U.S. Appl. No. 12/180,035, Response filed Jun. 22, 2011 to Non Final Office Action mailed Dec. 27, 2010", 9 pgs.
"U.S. Appl. No. 12/180,035, Response filed Jul. 16, 2009 to Non Final Office Action mailed Apr. 16, 2009", 9 pgs.
"U.S. Appl. No. 12/180,035, Response filed Dec. 22, 2011 to Final Office Action mailed Sep. 27, 2011", 8 pgs.
"U.S. Appl. No. 12/180,035, Response received Feb. 16, 2010 to Final Office Action mailed Nov. 16, 2009", 13 pgs.
"U.S. Appl. No. 12/180,035, Response received Oct. 11, 2010 to Non Final Office Action mailed Jun. 10, 2010", 7 pgs.
"Collagraft Bone Graft Substitute (Physician Package Insert)", Distribute by Zimmer, Inc., Warsaw, Indiana, (Mar. 1989), 1 pg.

(56) References Cited

OTHER PUBLICATIONS

"European Application Serial No. 01991379.7, Office Action mailed Jun. 17, 2005", 5 pgs.
"European Application Serial No. 07013717.9, European Search Report mailed Sep. 4, 2007", 8 pgs.
"European Application Serial No. 07013717.9, European Search Report mailed Sep. 10, 2007", 5 pgs.
"European Application Serial No. 07013717.9, Office Action mailed Apr. 1, 2008", 2 pgs.
"European Application Serial No. 07864863.1, Office Action mailed Feb. 22, 2011", 5 pgs.
"European Application Serial No. 07864863.1, Office Action mailed Nov. 6, 2009", 5 pgs.
"European Application Serial No. 07864863.1, Response filed Mar. 16, 2010 to Office Action mailed Nov. 6, 2009", 10 pgs.
"European Application Serial No. 07864863.1, Response filed Nov. 4, 2011 to Office Action mailed Feb. 22, 2011", 7 pgs.
"European Application Serial No. 98908535.2, Office Action mailed Feb. 1, 2006", 4 pgs.
"European Application Serial No. 98908535.2, Office Action mailed Feb. 2, 2005", 4 pgs.
"European Application Serial No. 98908535.2, Office Action mailed Nov. 6, 2006", 3 pgs.
"European Application Serial No. 98908535.2, Response filed May 29, 2006 to Office Action mailed Feb. 1, 2006", 9 pgs.
"European Application Serial No. 98908535.2, Response filed Aug. 2, 2005 to Office Action mailed Feb. 2, 2005", 8 pgs.
"European Application Serial No. 98908535.2, Search Report mailed Mar. 25, 2004", 3 pgs.
"International Application Serial No. PCT/US01/49314, International Search Report mailed Apr. 7, 2002", 5 pgs.
"International Application Serial No. PCT/US01/49314, International Search Report mailed Apr. 7, 2002", 4 pgs.
"International Application Serial No. PCT/US2001/049314, International Preliminary Examination Report mailed Oct. 24, 2002", 2 pgs.
"International Application Serial No. PCT/US2007/085853, International Preliminary Report on Patentability mailed Jun. 23, 2009", 8 pgs.
"International Application Serial No. PCT/US2007/085853, International Search Report mailed Mar. 7, 2008", 5 pgs.
"International Application Serial No. PCT/US2007/085853, International Search Report mailed Jul. 3, 2008", 4 pgs.
"International Application Serial No. PCT/US2011/060823, International Search Report Jan. 24, 2012", 3 pgs.
"International Application Serial No. PCT/US2011/060823, Written Opinion Jan. 24, 2012", 4 pgs.
"Japanese Application Serial No. 1998535914, Office Action mailed Sep. 30, 2008", 3 pgs.
"Japanese Application Serial No. 1998535914, Response filed Aug. 10, 2009", w/Translation, 40 pgs.
"Japanese Application Serial No. 2002-552590, Office Action mailed Mar. 31, 2009", 4 pgs.
"Japanese Application Serial No. 2002-552590, Office Action mailed Aug. 19, 2008", 6 pgs.
"Japanese Application Serial No. 2002-552590, Office Action mailed Dec. 20, 2011", 2 pgs.
"Japanese Application Serial No. 2002-552590, Office Action Received May 6, 2011", 10 pgs.
"OP-1: The First Name in BMPs", Stryker Biotech, http://www.opl.com/home.cfm?countryID=5, (Jan. 2004), 3 pgs.
"Osteoinductive", Scientific.net, http://www.scientific.net/Osteoinductive.htm, (Jan. 2004), 1 pg.
"Spinal Technologies:INFUSE Bone Graft/LT-CAGE Lumbar Tapered Fusion Device", Medtronic Sofamor Danek, http://www.medtronicsofamordanek.com/patient-spinal-infuse.html, (Jan. 23, 2004), 4 pgs.
Alpaslan, C., et al., "Bone reaction to subperiosteally implanted hydroxyapatite/collagen/glycosaminoglycans and coral in the guinea pig", Oral Surg. Oral Med. Oral Path., vol. 77, No. 4 (1994), 335-340, 5 pgs.
Asahina, I., et al., "Repair of Bone Defect in Primate Mandible using a Bone Morphogenetic Protein (BMP)-Hydroxyapatite-Collagen Composite", J. Med. Dent. Sci., vol. 44, (1997), 63-70.
Bar-Shavit, Z., et al., "Glucocorticoids Modulate Macrophage Surface Oligo saccharides and Their Bone Binding Activity", J. Clin. Invest., vol. 73, (1984), 1277-1283.
Benque, E., et al., "Tomodensitometric and Histologic Evaluation of the Combined Use of a Collagen Membrane and a HydroxyapatiteSpacer for Guided Bone Regeneration: A Clinical Report", Int. J. Oral Maxillofac. Implants, vol. 14, (1999), 258-264.
Bentz, Hanne, et al., "Purification and Characterization of a Unique Osteoinductive Factor from Bovine Bone", The Journal of Biological Chemistry, vol. 264, No. 32, (Dec. 1989), 20805-20810.
Bentz, Hanne, et al., "Transforming Growth Factor-β2 Enhances the Osteo-inductive Activity of a Bovine Bone-Derived Fraction Containing Bone Morphogenetic Protein-2 and 3", Matrix, vol. 11, (1991), 269-279.
Block, et al., "Glycol Methacrylate Embedding Technique Emphasizing Cost Containment, Ultrarapid Processing, and Adaptability to a Variety of Staining Techniques", Laboratory medicine 13(5), (May 1982), 290-298.
Boden, Scott D, et al., "Evaluation of a Bovine-Derived Osteoinductive Bone Protein in a Nonhuman Primate Model of Lumbar Spinal Fusion", American Academy of Orthopaedic Surgeons 1996 Annual Meeting—Scientific Program, http://www.aaos.org/wordhtml/anmeet96/sciprog/073.htm, (Feb. 1996), 2 pgs.
Borsato, K., et al., "Measurement of Partition of Stress Between Mineral and Collagen Phases in Bone Using X-ray Diffraction Techniques", J. Biomechanics, vol. 30, No. 9, (1997), 955-957.
Brown, W. E., et al., "Chemical Properties of Bone Mineral", Ann. Res. Mater. Sci., 6, (1976), 213-236.
Brown, W. E., et al., "Crystal Chemistry of Octacalcium Phosphate", Prog. Crystal Growth Charact., 4, (1981), 59-87.
Burwell, R. G, "The function of bone marrow in the incorporation of a bone graft.", Clin Orthop Relat Res., 200, (Nov. 1985), 125-141.
Cheng, Hongwei, et al., "Osteogenic Activity of the Fourteen Types of Human Bone Morphogenetic Proteins (BMPs)", The Journal of Bone & Joint Surgery 85-A (8), (Aug. 2003), 1544-1552.
Clarke, K. I., et al., "Investigation into the Formation and Mechanical Properties of a Bioactive Material Based on Collagen and Calcium Phosphate", Journal of Materials Science in Medicine, 4, (1993), 107-110.
Cornell, Charles N, "Initial Clinical Experience with Use of Collagraft as a Bone Graft Substitute", Techniques in Orthopaedics, vol. 7, No. 2, (1992), 55-63.
Cornell, Charles N, et al., "Multicenter Trial of Collagraft as Bone Graft Substitute", Journal of Orthopaedic Trauma, vol. 5, No. 1, (1991), 1-8.
Damien, Christopher J, et al., "Bone Graft and Bone Graft Substitutes: A Review of Current Technology and Applications", Journal of Applied Biomaterials, vol. 2, (1991), 187-208.
Delustro, Frank, et al., "Immune Responses to Allogeneic and Xenogeneic Implants of Collagen and Collagen Derivatives", Clinical Orthopaedics and Related Research 260, (Nov. 1990), 263-279.
Derutier, et al., "Biphosphonates: Calcium Antiresorptive Agents", Endocrine Module, Spring, [Online]. Retrieved from the Internet: <URL: http://www.auburn.edu/~deruija/endo_bisphos.pdf>, (2002), 1-7.
Endres, M., et al., "Osteogenic Induction of Human Bone Marrow-Derived Mesenchymal Progenitor Cells in Novel Synthetic Polymer-Hydrogel Matrices", Tissue Engineering, vol. 9, No. 4, (2003), 689-702.
Francis, Marion D., et al., "Hydroxyapatite Formation from a Hydrated Calcium Monohydrogen Phosphate Precursor", Calcif. Tissue Res., 6, (1971), 335-342.
Galbavy, S., et al., "AtelocollagenlHydroxylapatite Composite Material as Bone Defects Fillers in the Experiment on Rats", Bratisl. Med. J., vol. 96, (1995), 368-370.
Grigoryan, A., et al., "Time Course of Bone Defect Healing After Implantation in Them of Collagen-Hydroxyapatite Complexes: Experimental and Morphological Study", Stomatologia, vol. 75, (1996), 13-16.

(56) References Cited

OTHER PUBLICATIONS

Guillemin, et al., "The use of coral as a bone graft substitute", J. Biomed. Mat. Res. 21, (1987), 557-567.

Hamson, K., et al., "Preliminary Experience with a Novel Model Assessing In Vivo Mechanical Strength of Bone Grafts and Substitute Materials", Calcif. Tissue Int., vol. 57, (1995), 64-68.

Ho, Hsiu-O, et al., "Characterization of collage isolation and application of collagen gel as a drug carrier", Journal of controlled release, vol. 44, (1997), 103-111.

Hott, et al., "Ceramics in Substitutive and Reconstructive Surgery", P. Vincenzini, ed.,, (1991), 345-352.

Hsu, F., et al., "Microspheres of hydroxyapatite Ire constituted collagen as supports for osteoblast cell growth", Biornaterials, vol. 20, (1999), 1931-1936.

Ito, M., et al., "In vitro properties of a chitosan-bondedhydroxyapatite bone filling paste", Biomaterials, vol. 12, (41-45), 1991.

Itoh, Takashi, et al., "Structural Analysis of Collagen Fibrils in Rat Skin Based on Small-Angle X-Ray-Diffraction Pattern", Jpn. J. Appl. Phys., Part 1, No. 12A, (1996), 6172-6179.

Johnsson, Mats, et al., "The Role of Brushite and Octacalcium Phosphate in Apatite Formation", Critical Reviews in Oral Biology and Medicine, vol. 3, (1993), 61-82.

Katthagen, B., et al., "Experimental Animal Investigation of Bone Regeneration with Collagen-Apatite", Arch. Orthop. Trauma Surg. vol. 103, (1984), 291-302.

Kocialkowski, et al., "Bone Grafts, Derivatives & Substitutes", Collagraft Combined with Autogeneic Bone Marrow: Experimental and Clinical Results, Chapter 14, (1994), 271-290.

Kocialkowski, A., et al., "Clinical Experience with a New Artificial Bone Graft: Preliminary Results of a Prospective Study", Injury: The British Journal of Accident Surgery, vol. 21, (1990), 142-144.

Kubler, N., et al., "Bone Morphogenetic Protein-Mediated Interaction of Periosteum and Diaphysis", Clincal Orthopedics and Related Research, vol. 258, (1990), 279-294.

Lane, et al., "", J. Orthop. Trauma 2 (1) (abstract), (1988), 57-58.

Linder, L., et al., "Electron Microscopic Analysis of the Bone-Titanium Interface", Acta Orthop. Scand., vol. 54, (1983), 45-52.

Lindholm, T., et al., "The role of autogeneic bone marrow in the repair of a skull trephine defect filled with hydroxyapatite granules in the rabbit", Int. J. Oral Maxillofac. Surg., vol. 23, (2004), 306-311.

Liu, Y. M, et al., "2714 Osteoinductive Implants: The mis-en-scene for drug-bearing biomimetic coatings", Osteoinductive Implants, http://iadr.confex.com/iadr/2004Hawaii/techprogram/abstract_40044.htm, (Jan. 2004), 1 pg.

McIntyre, et al., "Characterization of a Bioceramic Composite for Repair of Large Bone Defects", Ceramic Bulletin 70 (9), (1991), 1499-1503.

Mehlisch, D., et al., "Histologic evaluation of the bonelgraft interface after mandibular augmentation with hydroxylapatitelpurified fibrillar collagen composite implants", Oral Surg. Oral Med. Oral Pathol., vol. 70, (1990), 685-692.

Minabe, M., et al., "Histological Study fo the Hydroxyapatite-Collagen Complex Implants in Periodontal Osseous Defects in Dogs", J.Periodontol.,, (Oct. 1988), 671-678.

Mittelmeier, H., et al., "Clinical Experience in the Implantation of Collagen-Apatite for Local Bone Regeneration", Z. Orthop., vol. 121, (1983), 115-123.

Muschler, George F, et al., "Evaluation of Bone-Grafting Materials in a New Canine Segmental Spinal Fusion Model", Journal of Orthopaedic Research, vol. 11, No. 4, (Jul. 1993), 514-524.

Nathan, et al., "Osteogenesis in Rats With an Inductive Bovine Composite", Journal of Orthopaedic Research 6, (1993), 325-334.

Nathan, Ranga M, et al., "Osteogenesis in Rats with an Inductive Bovine Composite", Journal of Orthopaedic Research, vol. 6, No. 3, (1988), 324-334.

Noah, E. M, et al., "Impact of Sterilization of the Porous Design and Cell Behavior in Collagen Sponges Prepared for Tissue Engineering", Biomaterials, vol. 23, (2002), 2855-2861.

Ohura, Kouichiro, et al., "Healing of Segmental Bone Defects in Rats Induced by a Beta-TCP-MCPM Cement Combined with rhBMP-2", Journal of Biomedical Materials Research 44(2), (1999), 168-175.

Oxlund, H., et al., "The roles of hyaluronic acid, collagen and elastin in the mechanical properties of connective tissues", J Anat., 131(Pt 4), (Dec. 1980), 611-20.

Pasquier, G., et al., "Injectable percutaneous bone biomaterials: an experimental study in a rabbit model", J. Mat. Sci. Mat. Med., vol. 7, No. 11, (1996), 683-690.

Peng, Y, et al., "Transcriptional Characterization of Bone Morphogenetic Proteins (BMPs) Mediated Osteogenic Signaling", J. Cell Biochem. vol. 90, No. 6, http://www.ncbi.nlm.nih.gov/entrez/query.fcgi?cmd=Retrieve&db=PubMed&list_uids=14, (Dec. 2003), 1149-1165.

Pohunkova, H., et al., "Reactivity and the fate of some composite bioimplants based on collagen in connective tissue", Biomaterials, vol. 16, (1995), 67-71.

Ronziere, et al., "Analysis of types I, II, III, IX and XI collagens synthesized by fetal bovine chondrocytes in high-density culture", Osteoarthritis and Cartilage 5, (1997), 205-214.

Rosenblatt, et al., "Injectable Collagen as a pH-sensitive hydrogel", Biomaterials, vol. 15, No. 12, (1994), 985-995.

Rovira, A., et al., "Colonization of a calcium phosphate/elastin-solubilized peptide-collagen composite material by human osteoblasts", Biornaterials, vol. 17, (1996), 1535-1540.

Sampath, et al., "Isolation of Osteogenin, an extracellular matrix-associated, bone-inductive protein, by heparin affinity chromatography", Proc. Natl. Acad. Sci USA 84, (Oct. 1987), 7109-7113.

St. John, K., et al., "Response of Canine Boneto a Synthetic Bone Graft Material", Clin. Mat., vol. 12, (1993), 49-55.

Stone, et al., "Porcine and Bovine Cartilage Transplants in Cynomolgus Monkey", Transplantation, vol. 63, No. 5, Williams & Wilkins, USA, (Mar. 15, 1997), 640-645.

Suganuma, J., et al., "In vivo Evaluation of Collagen-Coated Dacron Fiber in Bone", Clin. Mat., vol. 15, (1994), 43-50.

Takagi, Katsumasa, et al., "The Role of Bone Marrow in Bone Morphogenetic Protein-induced Repair of Femoral Massive Diaphyseal Defects", Clinical Orthopaedics and Related Research, vol. 171, (Dec. 1982), 224-231.

Thorne, et al., "CopiOs Injectible Paste Development Preliminary Disclosure Summary", (2004).

Truumees, et al., "Alternatives to Autologous Bone Harvest in Spine Surgery", The University of Pennsylvania Orthopaedic Journal 12, USA, (1999), 77-88.

Zardiackas, Lyle D, et al., "Torsional Properties of Healed Canine Diaphyseal Defects Grafted with a Fibrillar Collegen and Hydroxyapatite/Tricalcium Phosphate Composite", Journal of Applied Biomaterials 5, (1994), 277-283.

Zerwekh, Joseph E, et al., "Fibrillar Collagen-Biphasic Calcium Phosphate Composite as a Bone Graft Substitute for Spinal Fusion", Journal of Orthopaedic Research, vol. 10, No. 4, (1992), 562-572.

* cited by examiner

Figure 11
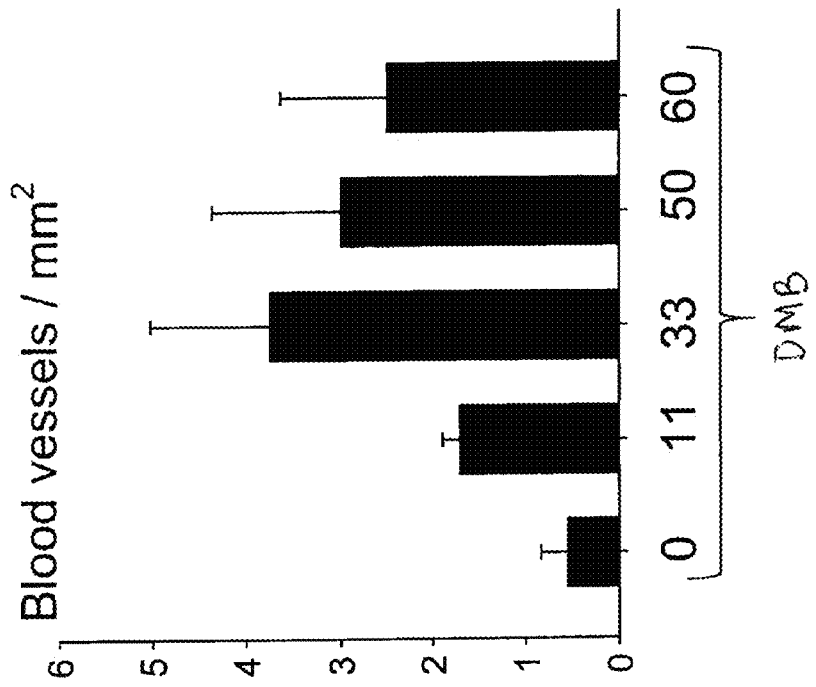

Figure 16
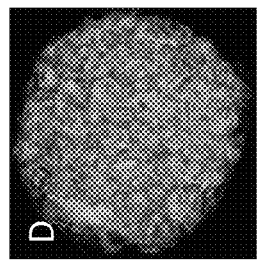
Collagen + DMB + CaAc 19%
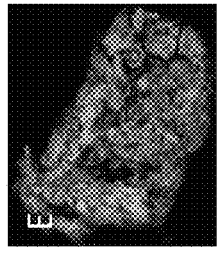
Collagen + DMB + Na₃PO₄ + CaAc 10%
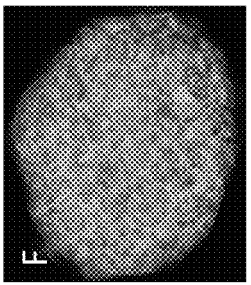
Collagen + DMB + DiCal + CaAc 10%
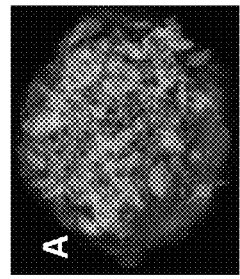
Collagen+DMB
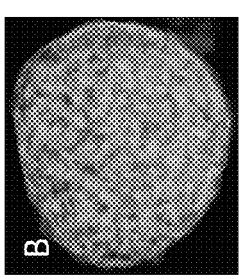
Collagen+DMB+BMP
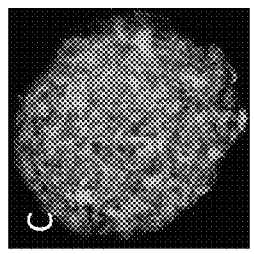
Collagen + DMB + CaAc 10%

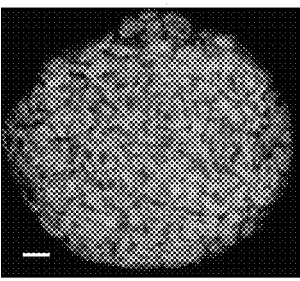
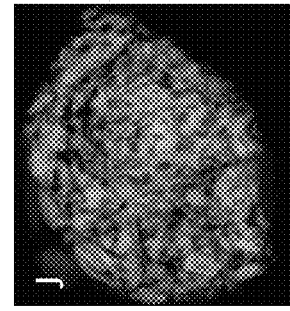
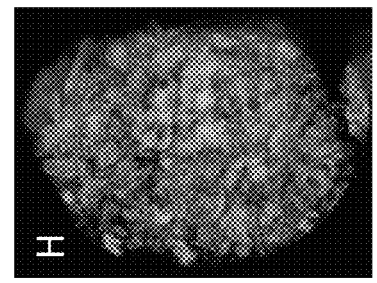
Figure 16

Figure 22
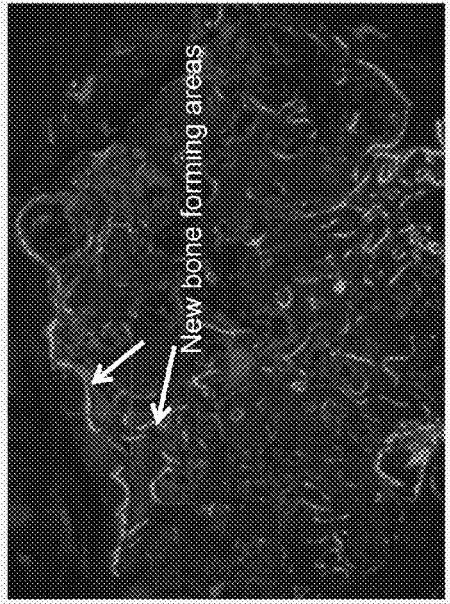
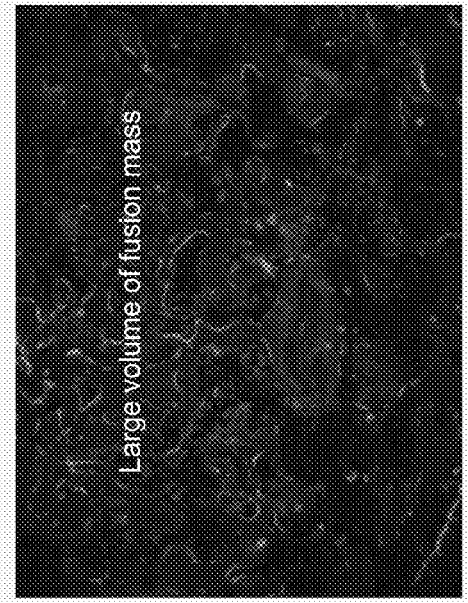
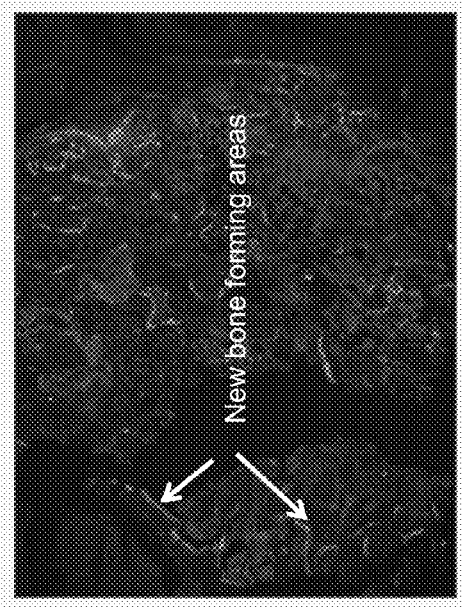
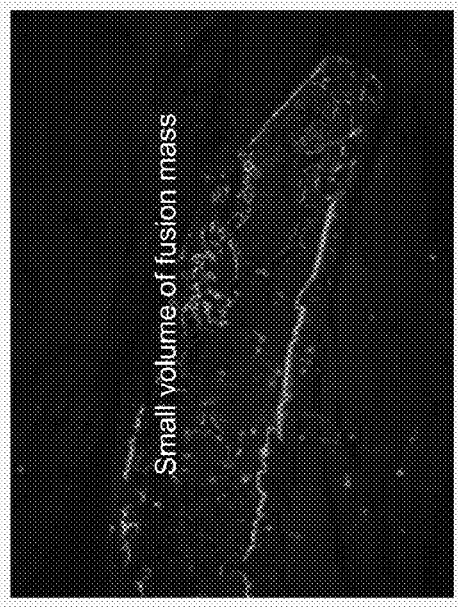

BONE VOID FILLERS

CROSS-REFERENCE TO RELATED APPLICATIONS

This application claims the benefit of U.S. application Ser. No. 61/413,502, filed on Nov. 15, 2010 and U.S. application Ser. No. 61/541,690, filed on Sep. 30, 2011, under 35 U.S.C. §119(e), which are incorporated by reference herein.

FIELD OF THE INVENTION

The field of the invention relates generally to bone void filler compositions, the preparation of the bone void filler compositions, and use of the bone void filler compositions, e.g., in promoting bone growth.

BACKGROUND

In the fields of orthopedics (e.g., reconstructive, trauma, spine, and dentistry), effective repair of bone defects, which may have been caused by disease, injury, wounds, or surgery, has long been a goal. A number of materials and compositions have been considered, evaluated, or used. Beyond their ability to promote bone growth, the biological, physical, and mechanical properties of the materials and compositions are factors, among others, affecting their suitability and performance in various applications.

Bone grafting has been commonly used to augment healing in treating a variety of musculoskeletal disorders. Grafting techniques in this field have been practiced for over 100 years and include procedures employing autograft, allograft and xenograft materials. Autologous cancellous bone is considered the standard against which other treatments are evaluated. Autograft cancellous bone is non-immunogenic and has all the appropriate structural and functional characteristics appropriate for the particular recipient. Autograft cancellous bone provides both a natural tissue scaffold and osteoinductive growth factors and may also contain osteogenic components (e.g., mesenchymal stem cells) if obtained with bone marrow. Autologous cancellous bone, however, is not acceptable or otherwise available for all patients. Autograft sources, as well as allograft sources, are relatively limited and may be expensive or painful to obtain. These and other limitations of autografts and allografts have resulted in alternative compositions being pursued as graft substitutes to fill defects (e.g., voids) in bone. Numerous bone graft substitutes having osteoinductive and/or osteoconductive properties have been explored and include, but are not limited to, products containing hydroxyapatites, tricalcium phosphates, aliphatic polyesters (poly(lactic) acids (PLA), poly(glycolic)acids (PGA), and polycaprolactone (PCL)), polyhydroxybutyrate (PHB), cancellous bone allografts, human fibrin, plaster of Paris, apatite, wollastonite (calcium silicate), bioactive glasses, ceramics, titanium, devitalized bone matrix, non-collagenous proteins, collagen, and autolyzed antigen extracted allogenic bone.

Demineralized bone, in the form of scaffold, granules, particulate, and/or powder, has been used in certain bone graft substitutes due to its osteoinductive properties. Osteoinductive components induce bone formation by stimulating stem cells and osteoprogenitor cells to undergo the osteogenic differentiation pathway. In the 1960's, demineralized bone was observed to induce the formation of new cartilage and bone when implanted in ectopic sites (Urist, 1965, Science 150:893-899). Demineralized bone can be prepared by grinding a bone, demineralizing it with an acid solution, washing with water or a phosphate buffered solution, washing with ethanol and drying it. Demineralized bone may be obtained from a source such as a commercial bone or tissue bank (e.g., AlloSource, Denver Colo.).

SUMMARY

The present invention provides bone void filler compositions, methods to prepare bone void filler compositions, and uses of bone void filler compositions, for example, to promote bone growth. For instance, in one example, the present invention includes bone void filler compositions containing an acidic mineral component, an osteoinductive component that contains demineralized bone (DMB) which comprises collagen, and a biologically acceptable osteoconductive carrier component.

In accordance with one aspect of the invention, there is provided a bone void filler composition containing an acidic mineral component that contains a calcium source and a phosphate source or a lower alkyl carboxylate source, e.g., $R-COO^-$ where R is $(CH_3)(CH_2)_n$ where n is 0, 1, 2, 3 or 4, such as a mineral salt; an osteoinductive component that contains demineralized bone which comprises collagen; and a three-dimensional, osteoconductive biologically acceptable carrier component that contains a collagenous material. In one embodiment, there is provided a bone void filler composition containing an acidic mineral component that contains a calcium source and a phosphate source, an osteoinductive component that contains demineralized bone and a three-dimensional, osteoconductive biologically acceptable carrier component that contains a collagenous material. The acidic mineral component in the composition is present in the range of about 1% to about 60% by weight relative to the combined weight of the acidic mineral component and the total weight of the collagen, accounting for collagen contained in the carrier as well as any collagen found in other components, including the demineralized bone. In one embodiment, the acidic mineral component comprises $CaHPO_4 2H_2O$ or calcium acetate. In one embodiment, the acidic mineral component is a self-setting cement, such as brushite (calcium hydrogen phosphate dihydrate ($CaHPO_4.2H_2O$)) cement, which when included with other components disclosed herein, provides for a self-setting bone void filler composition.

The bone void filler composition may be in the form of a sponge or in the form of a paste or putty, e.g., a paste or putty obtained from particulated sponge or from rehydrated sponge. The sponge, paste or putty may include additional components, e.g., one or more components that improve retention of demineralized bone particles, improve extrudability, e.g., from a syringe or through a cannulated device, improve cohesiveness in water or other physiologically compatible liquid carriers, improve moldability, improve shape retention during irrigation, and/or improve structural integrity, or any combination thereof, relative to a sponge, paste or putty without the additional component(s). A putty or paste of the invention may be injected or introduced to a mold, or manipulated without use of a device. In certain embodiments, a paste or putty may have a more dynamic three-dimensional structure than a sponge. For example, a putty or paste has a three-dimensional shape which can be altered but which has a volume which is substantially the same after being subjected to a force that results in the altered shape. A sponge has a three-dimensional shape and volume which can be altered, e.g., by compression, but is capable of having the same shape and volume after the force that alters the shape and volume is removed.

In one embodiment, the bone void filler composition comprises an acidic calcium phosphate component from about 8 wt % to about 12 wt % of the composition; an osteoinductive demineralized bone component from about 70 wt % to about 80 wt % of the composition; and an osteoconductive collagen carrier component from about 10 wt % to about 16 wt % of the composition; wherein the composition is in the form of a porous three dimensional structure. In one embodiment, the acidic calcium phosphate component in the bone void filler composition comprises monocalcium phosphate monohydrate [$Ca(H_2PO_4)2H_2O$]; calcium hydrogen phosphate dihydrate [$CaHPO_4 2H_2O$], amorphous calcium phosphate [$Ca_3(PO_4)2H_2O$], anhydrous calcium hydrogen phosphate [$CaHPO_4$], partially dehydrated calcium hydrogen phosphate [$CaHPO_4 xH_2O$, where x is between 0 and 2], and/or calcium pyrophosphate ($Ca_2O_7P_2$) [$2CaO_2P_2O_5$]. In one embodiment, the composition has a pH from about 2 to about 7, for example, a pH from about 3 to about 5. In one embodiment, the demineralized bone is in a form selected from a powder, particle, granule, fiber, and combinations thereof. For example, the demineralized bone particle or granule size may be from about 105 μm to about 850 μm. In one embodiment, the demineralized bone component comprises human demineralized bone. In one embodiment, the osteoconductive collagen carrier component comprises non-human mammalian collagen, e.g., bovine collagen. In one embodiment, the osteoconductive collagen carrier component comprises Type I and/or Type III collagen, for instance, more than about 90 wt % Type I and less than about 10 wt % Type III collagen. In one embodiment, the porous three dimensional structure is in the form of a strip, disc, sheet, bullet or cylinder, or is shaped for dental ridge augmentation. In one embodiment, the bone void filler composition further comprises an additive selected from the group consisting of allograft chips, bioceramics, biocomposites, calcium salts other than the acidic calcium phosphate component, phosphate salts other than the acidic calcium phosphate component; and combinations thereof. In one embodiment, the bone void filler composition further comprises an additive selected from the group consisting of bioresorbable fibers, synthetic polymers, and combinations thereof. In one embodiment, the bone void filler composition further comprises a liquid carrier selected from selected from the group consisting of biological fluids selected from the group consisting of bone marrow aspirate, whole blood, serum, and/or plasma; biocompatible liquids selected from the group consisting of water, saline and/or aqueous buffers; and combinations thereof. In one embodiment, the liquid carrier comprises bone marrow aspirate and saline.

In one embodiment, the bone void filler composition further comprises a collageneous biologically acceptable carrier component or a biocompatible, bioresorbable fiber, such as a glass fiber, a synthetic polymer, for instance, a synthetic biodegradable polymer, or other material that enhances load bearing properties, including but not limited to woven, non-woven (e.g., electrospun), mesh or struts. The collagenous biologically acceptable carrier component may differ in source (e.g., human versus bovine collagen, or collagen from bone versus collagen from skin) or type (e.g., fibrillar collagen or denatured collagen) from the collagen or collagenous material in the osteoinductive component or the osteoconductive component. In one embodiment, the collageneous biologically acceptable carrier comprises a gelatin or heat denatured and solubilized collagen. A synthetic biodegradable polymer includes but is not limited to polyvinylpyrrolidone, aliphatic polyesters (poly(lactic) acids (PLA), poly(g-lycolic)acids (PGA), poly(dl-lactide-co-glycolide) (PLGA), polycaprolactone (PCL)), or polyhydroxybutyrate (PHB) in either homopolymer or copolymer form. The bioresorbable fiber may be in the form of a mesh to encapsulate the other components, which mesh improves the structural integrity of the composition. In one embodiment, the inclusion of a biocompatible, bioresorbable fiber in the bone void filler composition may allow for the use of lower amounts of the collagenous biologically acceptable carrier component, e.g., where the fiber also provides a scaffold.

In accordance with one aspect of the invention, there is provided a self-setting bone void filler composition comprising an acidic mineral component that contains a calcium source and a phosphate or sulfate source, an osteoinductive component that contains demineralized bone, a three-dimensional, osteoconductive biologically acceptable carrier component that contains a collagenous material, and a self-setting calcium containing cement. In one embodiment, a self-setting calcium containing cement includes a calcium phosphate cement such as brushite cement, hydroxyapatite cement, or calcium sulfate cement. The self-setting brushite cement can be produced by mixing beta-tricalcium phosphate (beta-TCP) with orthophosphoric acid or by mixing beta-TCP with pyrophosphoric acid or b mixing beta-TCP and monocalcium phosphate (MCP) with water or by mixing beta-TCP and MCP with glycolic acid or with citric acid. Self-setting hydroxyapatite cement can be produced by mixing tetracalcium phosphate (TTCP) and dicalcium phosphate dihydrate (DCPD) with water or sodium hydrogen phosphate ($Na_2HPO_4$) or by mixing alpha-TCP, calcium carbonate and monocalcium phosphate monohydrate (MCPM) with water, or by mixing alpha-TCP and MCMP, or by mixing MCPM with HA or by mixing beta-TCP with MCMP with water. The calcium sulfate cement can be produced by mixing calcium sulfate powder with water. The self-setting calcium containing cement in the composition is present in the range of about 10% to about 60% by weight relative to the combined weight of the acidic mineral component and the total weight of the collagen, accounting for collagen contained in the carrier as well as any collagen found in other components, including the demineralized bone. For example, the self-setting calcium phosphate cement in the composition is present in the range of about 10% to about 60% by weight relative to the combined weight of the acidic mineral component and the total weight of the collagen, accounting for collagen contained in the carrier as well as any collagen found in other components, including the demineralized bone.

In accordance with one aspect of the invention, there is provided a self-setting bone void filler composition comprising an acidic mineral component that contains a calcium source and a phosphate source, an osteoinductive component that contains demineralized bone, a three-dimensional, osteoconductive biologically acceptable carrier component that contains a collagenous material, and a self-setting polymer. In one embodiment, the self-setting polymer is a thermal sensitive biodegradable block copolymer which is dissolved in aqueous solution at or below the room temperature and transits into a gel phase at body temperature as the bone void filler composition is applied to the grafting site. Thermal sensitive biodegradable block copolymers include but are not limited to PEG/PLA and PEG/PLGA diblock and triblock copolymers, PEG/PCL diblock and tribock copolymer, polyethylene glycol grafted chitosan, or poly(dimethyl-β-malic acid-co-β-butyrolactone)/poly(lactic acid). In one embodiment, a self-setting biodegradable polymer system is 4-arm polyethylene glycol succinimidyl glutarate and albumin or 4-arm polyethylene glycol succinimidyl glutarate and 4-arm polyethylene glycol amine. The self-setting biodegradable polymer in the composition is present in the range of about 10% to about 50% by weight relative to the combined weight of the acidic mineral component and the total weight of the collagen, accounting for collagen contained in the carrier as well as any collagen found in other components, including the demineralized bone. In one embodiment, the self-setting polymer is a non-resorbable polymer which includes but is not limited to poly(methyl methacrylate) PMMA cement, poloxamer. In one embodiment, a bone void filler composition having a self-setting component that results in a self-setting formulation is useful in certain clinical situations, e.g. sinus lift, ridge augmentation, tooth extraction socket, etc.

In accordance with another aspect of the invention, there is provided a pre-mixed bone void filler composition containing an acidic mineral component that contains a calcium source and a phosphate source or a lower alkyl carboxylate source; an osteoinductive component that contains demineralized bone; and a biologically acceptable carrier component that includes a liquid carrier. In one embodiment, there is provided a premixed bone void filler composition containing an acidic mineral component that contains a calcium source and a phosphate source, an osteoinductive component that contains demineralized bone, and a biologically acceptable carrier component that includes a liquid carrier. In one embodiment, the acidic mineral component comprises $CaHPO_4$ or its hydrate form (e.g., $CaHPO_4 2H_2O$) or calcium acetate. The ratio of demineralized bone component to acidic mineral component ranges from about 0.5:1 to about 80:1. The premixed bone void filler composition may be in the form of a paste or putty, which is malleable, extrudable, and retains its shape during irrigation or handling in water or other physiologically compatible liquid carriers. The paste or putty may include additional components, e.g., those that improve retention of demineralized bone particles, improve extrudability, e.g., from a syringe, improve cohesiveness in water or other physiological compatible liquid carriers, improve moldability and/or improve shape retention during irrigation, or any combination thereof, relative to a paste or putty without the additional component(s). A paste or putty of the invention may be injected or introduced to a mold, or manipulated without use of a device. In certain embodiments, a paste or putty may have a more dynamic three-dimensional structure than a sponge.

In accordance with another aspect of the invention, there is provided a premixed bone void filler composition containing an acidic mineral component that contains a calcium source and a phosphate source or a lower alkyl carboxylate source; an osteoinductive component that contains demineralized bone; and a biologically acceptable carrier component that includes a liquid carrier. In one embodiment, there is provided a premixed bone void filler composition containing an acidic mineral component that contains a calcium source and a phosphate source an osteoinductive component that contains demineralized bone; and a biologically acceptable carrier component that includes a liquid carrier. In one embodiment, the acidic mineral component comprises $CaHPO_4$ or its hydrate form (e.g., $CaHPO_4 2H_2O$) or calcium acetate. The ratio of demineralized bone component to acidic mineral component ranges from about 0.5:1 to about 80:1. The premixed bone void filler composition may be in the form of a paste or putty, which is malleable, extrudable, and retains its shape during irrigation or handling in water or other physiologically compatible liquid carriers. The paste or putty may include additional components, e.g., those that improve retention of demineralized bone particles, improve extrudability, e.g., from a syringe, improve cohesiveness in water or other physiological compatible liquid carriers, improve moldability and/or improve shape retention during irrigation, or any combination thereof, relative to a paste or putty without the additional component(s). A paste or putty of the invention may be injected or introduced to a mold, or manipulated without use of a device. In certain embodiments, a paste or putty may have a more dynamic three-dimensional structure than a sponge.

In accordance with another aspect of the invention, there is provided a method for encouraging bone growth at a defect site. The method includes applying to the defect site a bone void filler composition in accordance with the various aspects of the invention. In one embodiment, a sponge, paste or putty of the invention may be employed alone or in combination, e.g., a sponge may be employed with a putty, or in conjunction with other implants, for restructuring or augmenting a defect. For example, a bone void filler composition that is applied in the method may be a sponge. In one embodiment, a bone void filler composition that is applied in the method may be a paste or putty formed by combining a particulated sponge with a liquid carrier. In one embodiment, a bone void filler composition that is applied in the method is a paste or putty that is formed by combining a rehydrated sponge of the invention with a liquid carrier and then with a biologically acceptable carrier. A paste or putty may be molded into a desired shape before being applied to a defect site, may be introduced to a cannulated device before being applied, e.g., injected into defect site, or may be manually shaped at the defect site.

Further provided is a bone void filler composition comprising: a three-dimensional composition comprising an acidic mineral component comprising a calcium source and a phosphate source or a lower alkyl carboxylate source, e.g., $R-COO^-$ where R is $(CH_3)(CH_2)_n$ where n is 0, 1, 2, 3 or 4; an osteoinductive component comprising demineralized bone comprising collagen; and an osteoconductive biologically acceptable carrier comprising a collagenous material, which is admixed with a collagenous biologically acceptable carrier to form a putty. In one embodiment, there is provided a kit for a bone void filler composition comprising: an acidic mineral component comprising a calcium source and a phosphate source or a lower alkyl carboxylate source; an osteoinductive component comprising demineralized bone comprising collagen; and a three-dimensional, osteoconductive biologically acceptable carrier component comprising a collagenous material; and instructions for preparing and/or using a sponge, paste or putty. The kit may further include a biologically acceptable carrier component comprising a liquid carrier.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 11 depicts vascularization results obtained in studies evaluating bone growth from subcutaneous implants in athymic rats.

FIG. 16 depicts representative radiographs of implants of DBM combined with various salts obtained at 4 weeks post subcutaneous implantation in athymic rats.

FIG. 22 illustrates fluorochrome stained sections from rats 8 weeks after posterior-lateral spine fusions that employed a bone void filler composition of the invention or a composition having collagen and BMP-2.

DESCRIPTION OF EMBODIMENTS

Figure 1:
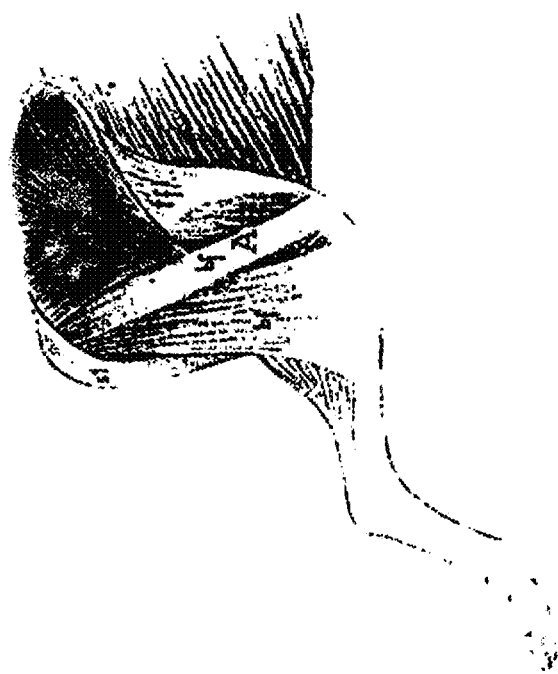
FIG. 1 is a representation of a rat showing positions of the intramuscular implants.

The present invention relates generally to bone void filler compositions, the preparation of the bone void filler compositions, and the use of the bone void filler compositions in preventing or inhibiting bone loss and/or promoting bone growth. For instance, the present invention relates to bone void filler compositions containing an acidic mineral component, an osteoinductive component that contains demineralized bone, and a biologically acceptable carrier component.

As described herein, the bone void filler compositions of the present invention have, as one (e.g., a "first") component, an osteoinductive component containing demineralized bone. As used in accordance with various embodiments of the present invention, "demineralized bone," or DMB, refers to bone that has been treated to remove an amount of the calcium phosphate mineral components sufficient to liberate (make more accessible) the endogenous bone growth factors. The level of demineralization of bone tissue is generally judged by the amount (wt &) of residual calcium found in the DMB. In general, "demineralized bone" refers to bone having less than about 8 wt % residual total calcium. The DMB useful in the compositions of the invention may be demineralized to have less than about 8 wt % residual calcium, less than about 4 wt % residual calcium, or between about 0.5 wt % to about 4 wt % residual calcium, or between about 0.5 wt % to about 2 wt % residual calcium.

Any demineralization processes known in the art, may be used to prepare DMB for use in the present invention. Demineralization is generally performed by exposing bone, from a mammalian, e.g., a human, source, to acidic solutions (e.g., HCl, acetic acid, or ethylene diamine tetracetic acid) with a pH less than about 4. The surface of the bone tissue is treated to remove a surface layer of its inorganic mineral, hydroxyapatite, leaving the structural properties of the organic phase of the bone constructs substantially unchanged. In some embodiments, the DMB may contain physiologically active levels of osteoinductive factors (e.g., bone morphogenetic proteins (BMPs)).

Demineralized bone may be provided as a powder, particulate, fiber or other form or may be provided in a matrix composition, "demineralized bone matrix (DBM)," where the powder, particles, and/or fibers may be combined with a liquid carrier to impart flowable or moldable properties to the composition. In particulate form, typical demineralized bone sources may have an average particle diameter of between about 105 microns and about 4 mm; between about 710 microns and about 2 mm; between about 200 microns and about 1 mm, between about 105 microns and about 500 microns; between about 105 microns and about 850 microns; or between about 250 microns and about 710 microns. In fiber form, typical demineralized bone sources may have an average thickness of between about 0.5 mm and about 15 mm and an average width of between about 2 mm and about 35 mm. The length of the fibers may vary from about 2 mm to about 300 mm.

Liquid carriers that can be used to prepare DBM include blood, blood components (e.g., plasma, serum or platelet rich plasma), bone marrow aspirate, normal or buffered saline, water, biocompatible liquids containing glycerol, lecithin, gelatin, hyaluronic acid, starch, or alginate, and/or other biocompatible liquids. The concentration of demineralized bone in DBM can be from about 10% to about 90% by weight (total weight including carrier).

The osteoinductive component of DMB is essentially the growth factors present in the DMB. Most of the osteoinductive factors are soluble at acidic pH. Hence, it is desirable that the growth factors are not extracted from the DMB during the acid demineralization process. DMB from cortical bone generally will have more osteoinductive factors than DMB from cancellous bone from the same source. Further, bone is known to contain inhibitors of bone formation (e.g., sclerostin).

The bone void filler compositions of the present invention may contain other components that have osteoinductive activity. Blood, blood components or bone marrow aspirate, when used in a composition, can contribute osteoinductive factors and/or osteogenic cells. Additionally osteoinductive factors such as recombinant or isolated bone morphogenetic proteins (e.g., BMP-2, BMP-7, GDF-5) may be added to the bone void filler compositions of the present invention.

Certain embodiments of the present invention may include freeze-dried demineralized bone. In some embodiments, the DMB may be freeze-dried to a point such that the freeze-dried bone has an average residual moisture of less than about 10 wt %, or less than about 5 wt %. In some embodiments, freeze-dried DMB may be rehydrated before use in preparing the bone void filler compositions of the present invention. Rehydrated freeze-dried DMB may have a residual moisture content of less than about 80 wt %, less than about 50 wt %, less than about 25 wt %, or between about 25 wt % and about 10 wt %, in certain embodiments.

The DMB may include more than one type of bone tissue (e.g., cancellous, cortical, or corticocancellous). The demineralized bone may include bone from a single donor source or from multiple donor sources. The demineralized bone may include materials from autogenic, allogenic or xenogenic sources (i.e., as compared to the DMB recipient).

As described herein, the bone void filler compositions of the present invention have, as another (e.g., a "second") component, an acidic mineral component. As used in accordance with various embodiments of the present invention, "acidic mineral component" refers to one or more components of the composition that provide an additional source of acidic mineral above and beyond any residual acidic mineral that might be present in the demineralized bone. The acidic mineral component provides local pH control and enhances the in vitro and/or in vivo efficacy of osteoinductive proteins. When combined with DMB or other sources of collagen, the acidic mineral component supplements local availability of essential bone components such as collagen, calcium, and phosphate. Moderately acidic microenvironments likely improve protein stimulated osteoinduction by enhancing the rates of protein solubilization and protein release from collagen. Supplementing the local concentration of soluble acidic mineral sources, such as $Ca^{2+}$ and $PO_4^{3-}$ ions, enhances the quantity and quality of bone produced, and increases rate of bone formation by reducing dependence on essential ion diffusion from serum and other body fluids.

The acidic mineral component of the present invention may contain a calcium containing source, a phosphate containing source or a lower alkyl carboxylate source, ceramic preforms, and/or other acidic minerals. "Contains," "comprise," "has," "having," or other similar language in the context of the "acidic mineral component" refers to the form in which the "acidic mineral component" is initially provided to the composition.

In one embodiment, the acidic mineral component has a calcium containing source and a phosphate source or a lower alkyl carboxylate containing source. The calcium source and the phosphate or lower alkyl carboxylate source may be present (e.g., provided) as a single compound or may be present as two or more compounds. For example, a single calcium phosphate present in the constituents used to make the bone void filler composition may be both the calcium source and the phosphate source. Alternatively, two or more compounds may be present in the constituents, where the compounds may include calcium, phosphate, or calcium and phosphate. Calcium and phosphate sources that may desirably be used in the mineral component of the present invention include monocalcium phosphate monohydrate [$Ca(H_2PO_4)_2H_2O$]; calcium hydrogen phosphate dihydrate [$CaHPO_42H_2O$], amorphous calcium phosphate [$Ca_3(PO_4)_2H_2O$], anhydrous calcium hydrogen phosphate [$CaHPO_4$], partially dehydrated calcium hydrogen phosphate [$CaHPO_4xH_2O$, where x is between 0 and 2], tricalcium phosphate, including both α- and β-[$Ca_3(PO_4)_2$], tetracalcium phosphate [$Ca_4(PO_4)_2O$], octacalcium phosphate [$Ca_8H_2(PO_4)_65H_2O$], and/or calcium pyrophosphate ($Ca_2O_7P_2$) [$2CaO_2P_2O_5$]. In one embodiment, anhydrous calcium hydrogen phosphate [$CaHPO_4$], partially dehydrated calcium hydrogen phosphate [$CaHPO_4xH_2O$, where x is between 0 and 2], and/or calcium hydrogen phosphate dihydrate [$CaHPO_42H_2O$], which are collectively referred to herein as "DiCal", are employed in the compositions of the invention. In certain embodiments, where a calcium phosphate compound is employed, the ratio of calcium to phosphate (i.e., ratio of calcium cations to phosphate groups) of the compound ranges from about 0.5 to about 1. In certain embodiments, where a calcium phosphate compound is employed, the ratio of calcium to phosphate (i.e., ratio of calcium cations to phosphate groups) of the compound ranges from about 0.5 to about 2. In one embodiment, a calcium lower alkyl carboxylate such as calcium acetate may also be used as a soluble mineral component of the present invention. For instance, calcium acetate may be used alone or in combination with other phosphate sources, which include but are not limited to calcium hydrogen phosphate [$CaHPO_4$], monocalcium phosphate monohydrate [$Ca(H_2PO_4)_2H_2O$]; calcium hydrogen phosphate dihydrate [$CaHPO_42H_2O$], amorphous calcium phosphate [$Ca_3(PO_4)_2H_2O$], anhydrous calcium hydrogen phosphate [$CaHPO_4$], partially dehydrated calcium hydrogen phosphate [$CaHPO_4xH_2O$, where x is between 0 and 2], tricalcium phosphate, including both α- and β-[$Ca_3(PO_4)_2$], tetracalcium phosphate [$Ca_4(PO_4)_2O$], octacalcium phosphate [$Ca_8H_2(PO_4)_65H_2O$], and/or calcium pyrophosphate ($Ca_2O_7P_2$) [$2CaO_2P_2O_5$]; sodium dihydrogen phosphate ($NaH_2PO_4$), disodium hydrogen phosphate ($Na_2HPO_4$), trisodium phosphate ($Na_3PO_4$). In one embodiment, calcium acetate is employed in a composition of the invention. In one embodiment, a calcium lower alkyl carboxylate such as calcium acetate combined with anhydrous calcium phosphate [$CaHPO_4$], partially dehydrated calcium hydrogen phosphate [$CaHPO_4xH_2O$, where x is between 0 and 2], and/or calcium hydrogen phosphate dihydrate [$CaHPO_42H_2O$], which are collectively referred to herein as "DiCal", are employed in a composition of the invention. In one embodiment, a calcium lower alkyl carboxylate such as calcium acetate combined with trisodium phosphate is employed in a composition of the invention. Calcium sources that may be used include, but are not limited to, calcium chloride [$CaCl_2$], calcium carbonate [$CaCO_3$], calcium oxide [$CaO$], calcium hydroxide [$Ca(OH)_2$], and the like. Phosphate sources that may be used include, but are not limited to, phosphoric acid [$H_3PO_4$], all soluble phosphates, and the like. The acidic mineral component may also contain sources of other minerals, including strontium, such as $SrHPO_4$, zinc, silicon, and/or magnesium. In one embodiment, the acidic mineral component may have a mineral other than (instead of) calcium, e.g., Sr, zinc, silicon or magnesium.

The form (e.g., crystals, particles, flakes, etc.) and size of the acidic mineral component may vary.

Compositions in accordance with the various embodiments of the present invention may contain additional agents to promote mineralization, including autograft, allograft or xenograft bone (e.g., cortical, cancellous or corticocancellous chips), bioceramics, biocomposites, proteins, lipids, and peptides.

Certain embodiment of the bone void filler compositions of the present invention also contain a biologically acceptable carrier component. The choice of biologically acceptable carrier component will depend on the form desired for the bone void filler compositions. In one embodiment, the biologically acceptable carrier component provides for a three-dimensional structure including the first and second components. In one embodiment, the biologically acceptable carrier component provides a three-dimensional, osteoconductive scaffold. In one embodiment, the three-dimensional, osteoconductive scaffold contains collagenous material, e.g., a scaffold formed of bovine collagen may contain other collagenous material, e.g., DMB particles may be a source of the other collagenous material. In one embodiment, the three-dimensional scaffold contains a polymer scaffold such as one prepared by weaving or electrospinning polycaprolactone (PCL), poly(D-, L-lactide) (PLA), polyhydroxybutyrate (PHB), chitosan, or a biocompatible, bioresorbable fiber as disclosed herein, e.g., instead of or in addition to a collagenous material.

In one embodiment, a bone void filler composition of the invention includes two different biologically acceptable carrier components, at least one of which provides for a three-dimensional structure. In one embodiment, a first biologically acceptable carrier component and a second biologically acceptable carrier component are mixed with an acidic mineral component, to form a slurry, and then DMB particles are added to the slurry, after which the resulting composition is added to a mold and subjected to freezing and lyophilization to form a dehydrated sponge. The dehydrated sponge may be rehydrated to form a putty.

In accordance with one group of embodiments of the present invention, which is subsequently described in greater detail, the compositions can be used in a rehydratable freeze-dried form, e.g., sponge, membrane, sheet, fleece, plug, rod, strip, etc. Such sponge may be mixed with additional components to form a putty or may, upon rehydration, form a putty. Sponges and putties are two embodiments and are used herein throughout as representative of other forms, e.g., pastes. Sponges may be stored in lyophilized form, frozen form or at temperatures from 15° C. to about 30° C. Putties or pastes may be stored at temperatures from about 15° C. to about 25° C.

In accordance with one group of embodiments of the present invention, which is subsequently described in greater detail, the compositions can be used as putties or pastes, e.g., in a malleable, moldable form (a dynamic three-dimensional structure). In one embodiment, a putty of the invention is prepared from a sponge by adding one or more biologically acceptable carrier components. In another embodiment, a putty of the invention is prepared by hydrating a lyophilized sponge that is formed by combining the first, second and third components discussed above with a collagenous biologically acceptable carrier component. In one embodiment, a pre-hydrated sponge, e.g., pre-hydrated with water, is prepared, provided or employed. In one embodiment, a bone void filler composition of the invention has putty like consistency and cohesiveness, has a fibrillar texture that may improve containment of DMB particles, has improved handling in water (e.g., decreased tendency to disintegrate) and/or provides for a three-dimensional structure that promotes better bone healing, e.g., as a result of the presence of the collagenous biologically acceptable carrier component. In one embodiment, a combination of biologically acceptable carrier components is present in the bone void filler composition of the invention, e.g., heat denatured collagen or heat denatured demineralized bone matrix and/or fibrillar collagen, and in one embodiment, the sources of collagen are the same.

In certain embodiments, "sponge" and "putty" compositions are adapted for use in making on-site preparations, e.g., preparations made at the time of an implantation procedure. For example, at the time of an implantation procedure, the sponge may be rehydrated with a suitable liquid carrier and then folded, molded or otherwise manipulated into a desired shape for use at a repair site. Alternatively, the sponge may be rehydrated with a suitable liquid carrier, excess moisture removed, and a collagenous biologically acceptable carrier component added and blended with the sponge to form a putty that is cohesive and malleable, which putty may be introduced to a repair site by a cannulated device (e.g., a syringe, needle, and/or cannula, and/or the like) or manually. In another embodiment, a lyophilized sponge may be rehydrated with a suitable liquid carrier which, after soaking, becomes a putty. Alternatively, the sponge may be particulated, either at the time of or prior to the implantation procedure. The particulated materials may then be combined with a suitable liquid carrier to form either a paste or putty. The liquid carriers that can be used to rehydrate the sponge or that can be combined with the particulate material to form a paste or putty, may be biological fluids, such as bone marrow aspirate, whole blood, blood components (e.g., serum, plasma, platelet rich plasma), etc., or other liquid carriers that include buffers, which may be desirable to buffer the composition to the physiological pH values of human serum (pH 7.1 to pH 7.4). Examples of buffers are known to those skilled in the art and include Tris and phosphate-buffered saline. More than one liquid carrier, for example, bone marrow aspirate and a buffering solution, may be used. The liquid carrier may include water, saline, glycerin, glycerol, lecithin, gelatin, hyaluronic acid, alginate, surfactants, carboxylic acids, dimethylsulfoxide, or tetrahydrofuran, or any combination thereof. Additionally, polymers such as aliphatic polyesters, polyethylene glycols, polyanhydrides, carboxylmethyl cellulose, hydroxymethyl cellulose, polysaccharides, dextran polymers, polymeric orthophosphates, or any combination thereof, may be used as the liquid carrier or be included in the composition.

As used in accordance with various embodiments of the present invention, "putty" refers to a dough-like/clay-like composition. "Paste," as used in accordance with various embodiments of the present invention, refers to a soft, moist, substance having a consistency between a liquid and a solid. A paste of the present invention is less solid than a putty and in some embodiments more solid that a gel, and in other embodiments may be injectable. As used in accordance with various embodiments of the present invention, "injectable" refers to the ability of certain bone void filler compositions of the present invention to be introduced at a repair site under pressure (as by introduction using a syringe or other cannulated device). An injectable composition of the present invention may, for example, be introduced between elements or into a confined space in vivo (e.g., between pieces of bone or into the interface between a prosthetic device and bone, into a tooth extraction socket, into alveolar ridge/sinus cavity, into a confined void with any geometry due to trauma created either natural or surgical procedure, into vertebral interbody spaces, spinal fusions, joint and trauma defects, bone fractures. An injectable composition may also be used to fill bone cysts, tumors and other well-delineated voids. A shaped composition may be used in spinal fusion, sinus lift, alveolar ridge augmentation, or a bone cavity (e.g., created by surgical procedure with regular geometry like a cylinder). Shaped compositions may also be designed as a circular sheet graft to be used in the acetabulum or a tubular graft to be used in the intramedullary space in primary and revision hip surgery or as a sheet that contours to the graft site to be used in fracture repair, bridge bone gaps or fragments, etc.

During application, the "putty" substance may be beaten or kneaded to the consistency of dough, and manipulated into a shape closely approximating that of the repair site. Pastes and putties provide ease of use and economy of product manufacture. Pastes and putties are desirable for surgical bone repair as they can be easily delivered to difficult surgical sites and molded in situ into desired shapes. These products are desirable for the reconstruction of skeletal defects, e.g., in spine, dental, and/or other orthopedic surgeries.

In one embodiment, the invention provides a malleable putty and the use of such a putty in bone grafting (e.g., joint revision) and surgical treatment of bony defects. In one embodiment, the putty comprises DMB particles, fibrillar collagen, an acidic mineral component (e.g., calcium phosphate dibasic (Dical)), and heat denatured collagen or gelatin as a collagenous carrier. The putty may be prepared by mixing fibrillar collagen, an acidic mineral component (e.g., calcium phosphate dibasic (Dical)), and an acidic solution (e.g., a hydrochloric acid containing solution) with DMB particles to form a mixture which is then lyophilized to form a sponge. The lyophilized mixture is then soaked in an aqueous liquid such as water, then gelatin or a heat denatured collagen or heat treated DMB particle containing solution is added to the rehydrated sponge (e.g., by injecting, spreading or soaking and gently blending with a spatula or by hand), so as to form a putty like material. For instance, a heat denatured collagen solution may be prepared by heating about 5% to about 30% (w/v), e.g., about 5% to about 15% or about 12% to about 30% (w/v), collagen in water or a saline (e.g., a 0.9% saline) solution at about 121° C. for about 1 hour to about 3 hours in an autoclave to partially or mostly dissolve the collagen. The resulting viscous collagen solution is cooled to about 37° C. to about 50° C. and then may be used to make the putty. Gelatin, e.g., about 5% to about 30% (w/v), such as about 5% to about 15% (w/v), may be dissolved by heating. The dissolved gelatin may be maintained at about 37° C. to about 50° C. and then may be used to make the putty. Similarly, DMB particles may be heated in a saline solution to about 121° C. for about 1 hour to about 3 hours in an autoclave to partially dissolve the DMB particles. The resulting DMB particle solution is cooled to about 37° C. to about 50° C. and then may be employed to prepare a putty. In one embodiment, the formulation includes a combination of fibrillar collagen and heat denatured collagen or gelatin or heat denatured DMB particles as a carrier to give putty-like flow and cohesiveness as well as a fibrillar three-dimensional structure which allows for molding into different shapes. The gelatin or heat denatured collagen may be from the same source as the fibrillar collagen or the gelatin may be produced by controlled acid hydrolysis (dilute HCl) of the fibrillar collagen followed by lyophilization to remove the acid.

In accordance with another embodiment of the present invention, which is subsequently described in greater detail, the bone void filler compositions can be used in a pre-mixed format, such as in the form of a paste or putty. Such pre-mixed, or ready-to-use, formulations have an advantage of requiring minimal preparation by the individual clinician or surgeon. The desired components of the paste or putty are dispersed in a liquid carrier to obtain a pre-mixed composition of a desired consistency. The liquid carriers that can be used to form the pastes or putties of this group of embodiments, may be selected from those liquid carriers described above for use in preparing the bone void filler compositions. In some embodiments, the liquid carriers contain biological fluids, such as bone marrow aspirate, whole blood, blood components (e.g., serum, plasma, platelet rich plasma), etc.

In accordance with the various embodiments of the present invention, the bone void filler composition may further contain a source of growth factor(s), e.g., bone morphogenetic proteins (BMPs). This source of growth factor(s) is in addition to any residual growth factor(s) that might be contained in the demineralized bone of the osteoinductive component. These additional growth factor(s) may come from blood, blood components or bone marrow aspirate used as a carrier.

BMPs are entrapped at high concentration within bone and are secreted by many bone-forming cell types. The primary function of BMPs is cellular signaling. Intracellular signaling occurs through the binding of a soluble growth factor to a specific cell receptor site. This signal pathway stimulates several different and important bone healing events, including the proliferation, migration, and differentiation of bone forming cells. The cells are, in turn, responsible for the synthesis of other proteins and growth factors that are important for regulating and controlling bone tissue formation. Although there is a vast array of BMPs described and known to one skilled in the art, BMP-2, -4, -6 and -7 are generally considered to be the most osteoinductive. Other growth factors, like TGF-beta1, TGF-beta 3, and PDGF may also be used to stimulate bone formation.

In certain embodiments, there is provided a bone void filler composition having: an osteoinductive component containing DMB; an acidic mineral component; and a biologically acceptable carrier component having a three-dimensional, porous, osteoconductive scaffold. The porous scaffold may be open, interconnected, etc. In general, the relative amounts of each component may vary, e.g., according to differences in patient age, gender, health, systemic conditions, habits, anatomical location, etc. However, as will be explained in greater detail herein, particularly useful bone void filler compositions may be obtained with the use of specified ranges of the components.

In one embodiment, the use of a three-dimensional, osteoconductive scaffold allows the bone void filler composition to be produced in the form of a sponge. It is believed that a biologically acceptable, porous, three-dimensional scaffold restores function and/or regenerates bone by providing a temporary matrix for cell proliferation and extracellular matrix deposition with consequent bone in-growth until new bony tissue is restored and/or regenerated. The matrix may also provide a template for vascularization of this tissue. The scaffold may actively participate in the regenerative process through the release of growth factors, minerals and/or other substances beneficial to the bone formation process if such are present in the scaffold.

The macro and micro-structural properties of the scaffold influence the survival, signaling, growth, propagation, and reorganization of cells. They may also influence cellular gene expression and phenotype preservation. The following scaffold characteristics contribute to bone formation: cell biocompatibility; surface chemistry; biodegradability, porosity; and/or pore size.

In certain embodiments, the composition contains a collagenous material as the three-dimensional, porous, osteoconductive scaffold. Collagen is the main protein of connective tissue in animals and the most abundant protein in mammals. Bone is composed of strong, fibrillar bundles of collagen encased within a hard matrix including calcium phosphate predominately in the form of hydroxyapatite. Collagen is also a constituent in cartilage, tendon, ligament, and other connective tissues.

The collagen protein possesses a distinctive triple-helix tertiary structure of three polypeptide chains supercoiled about a common axis and linked by hydrogen bonds. At least nineteen distinct molecules have been classified as collagens, and specific types are associated with particular tissues. The solubility of collagen is affected by its conformation and extent of associations, whereby newly synthesized collagen chains are generally soluble but after formation of fibrils, they become essentially insoluble.

Collagen fibrils, referred to as fibrillar collagen, result from covalent cross-linking between the supercoiled chains by an enzymatic mechanism that strengthens and stabilizes the chains. Fibrillar collagen may be obtained from native sources such as human or animal dermis, tendon, cartilage or bone. It is generally recovered by proteolytically degrading natural collagen crosslinks to produce tropocollagen. Tropocollagen is soluble in acidic solutions (in one embodiment, between pH 3 to pH 4). These solutions can be cleaned and purified prior to collagen fiber reassembly by pH neutralization. Fibrillar collagen is generally less dense, less soluble, and swells more in solution than non-fibrillar collagen. Fibrillar collagen may be prepared by any method, including those disclosed in Rubin et al., *Biochemistry*, 4:181 (1965); Helseth et al., *Biol. Chem.*, 256:7118 (1981); Capaldi et al., *Biopolymers*, 21:2291 (1982) and Gelman et al., *J. Biol. Chem.*, 254:11741 (1979), which are incorporated by reference herein. For example, a tissue source having collagen may be repetitively treated by mechanically removing contaminants, such as fat, and washing the mechanically treated materials in an alkaline solution, e.g., such as one that yields chlorine, which optionally also contains an anti-microbial agent. The washed material may be frozen and freeze dried prior to milling. In one embodiment, fibrillar collagen useful in the bone void filler compositions of the invention, has cross-links found in native tissue, which provides for a native three-dimensional structure. In one embodiment, fibrillar collagen useful in the bone void filler compositions of the invention is greater than about 90 wt % Type I collagen, e.g., about 95 wt % Type I collagen, which fibrillar collagen preparation may contain less than about 10 wt % Type III collagen, e.g., less than about 5 wt % Type III collagen.

Due to its high degree of biocompatibility with the human body, collagen has been successfully used in a variety of medical and dental applications for many years with minimal adverse responses. During its manufacture, potentially antigenic portions of the collagen molecule may be removed, resulting in a product that is highly biocompatible and well-tolerated by the tissue (e.g., atellopeptide collagen). Collagen is also chemotactic for fibroblasts and other cells involved in bone tissue repair. Collagen biocompatibility ensures that the products are well integrated in the host tissue without eliciting an immune response.

Collagenous materials used in the bone void filler compositions of the present invention may be from any source as long as they are capable of being used to form the implantable material. These include natural collagen sources such as mammalian, e.g., human, tissues, and synthetic collagen sources manufactured using recombinant technologies. The collagenous material may also contain gelatin. The collagen may be of any type (e.g., collagen Types I, II, III, or X and/or gelatin). In various embodiments, the collagen may be derived from bovine, porcine, equine, or ovine dermis or connective tissue. Bovine dermal collagen from Devro Medical and bovine tendon collagen from Collagen Matrix are acceptable collagens in certain embodiments. Type I collagen derived from tendon, fascia or bone may also be used. These tissues can be allogeneic or xenogeneic, such as from bovine, porcine, equine, or ovine sources. Soluble collagen, insoluble collagen, or combinations of soluble and insoluble collagen may be used as long as a sponge can still be obtained. Acids used to render collagens soluble, if not removed from the final bone void filler compositions of the present invention, may affect the stability of the compositions over time if the compositions are moist or wet. However, lyophilization results in the complete or partial removal of the acids used to solubilize collagen, greatly reducing any possible instability in certain embodiments. Nonetheless, in other embodiments, soluble collagen, if used as part of the carrier, may be subjected to steps to remove any residual acid followed by reconstitution.

The surface chemistry of the scaffold can control and affect cellular adhesion. It can also influence the solubility and availability of proteins essential for intracellular signaling. Intracellular signaling maximizes osteoinductivity through controlled cellular differentiation, proliferation, and stimulation.

Collagen also provides a favorable extracellular matrix for bone forming cells, e.g., osteoblasts, osteoclasts, osteocytes, etc. The natural affinity of bone forming cells for the collagen matrix has been demonstrated to favorably influence the function and signaling required for normal cellular activity.

The degradation rate of the scaffold desirably approximates the bone-forming rate. Slower degradation rates can hinder the rate of remodeled, load-bearing bone formation. Faster degradation can result in unhealed defects. The solubility and resorption of collagen is affected by its conformation and the degree of collagen cross-linking. The in vivo solubility and resorption of collagen is also influenced by the local concentration of proteolytic agents and vascularity at the site.

In order to form a more stable sponge structure, collagen from some sources may benefit from crosslinking before use. In one embodiment, collagens that do not require crosslinking following combination with the osteoinductive component are used. In embodiments where a crosslinked collagen is employed, the collagen may be crosslinked to control the solubility and the extent and rate of collagen resorption and improve the mechanical properties, e.g., tensile strength and elasticity. Collagen crosslinking may occur by various methods, such as dehydrothermal (DHT), UV light exposure, and chemical crosslinking with aldehydes (e.g., glyceraldehyde, formaldehyde, and glutaraldehyde), carbodiimides and various amino acids. The crosslinking conditions may typically preserve the in vivo lifetime of the bone void filler composition for up to about twelve weeks, allowing the collagen to function as a scaffold for bone healing, in contrast to non-crosslinked collagen containing compositions which may have an in vivo lifetime from 1 to 3 weeks. Collagen is eventually degraded by host enzymes in the surrounding tissue.

Scaffolds with high porosity and interconnectivity are generally desired. Scaffolds desirably possess an open pore, fully interconnected architecture to allow homogeneous and rapid cell in-growth, and facilitate vascularization of the construct from the surrounding tissue. To this end, the total pore volume porosity of the scaffold desirably simulates that of cancellous bone. Cancellous bone is a highly porous structure (about 50 vol. % to about 90 vol. %) arranged in a sponge-like form, with a honeycomb of branching bars, plates, and rods of various sizes called trabeculae. In one embodiment of the present invention, the scaffold desirably ensures pore interconnectivity to allow for the diffusion of nutrients and gases and for the removal of metabolic waste resulting from the activity of the cells within the scaffold. Smaller pores may occlude and restrict cellular penetration, matrix production, and tissue vascularization. Larger pores may detrimentally influence the mechanical properties of the structural scaffold. In one embodiment, pore size may ranges from about 1 µm to about 5 mm. In one embodiment, pore size may range from about 10 µm to about 5 mm. In one embodiment, pore size may range from about 10 µm to about 1 mm. In one embodiment, porosity ranges are from about 30 vol. % to about 90 vol. %

In some embodiments, the DMB source may also be the source of the collagenous material. Such collagenous materials that may also be a source of demineralized bone include commonly available DMBs, e.g., from Allosource Inc., RTI Biologics, Osteotech Inc., e.g., DMB without a carrier. In such embodiments, to obtain a composition of a desired consistency it may be necessary to add a liquid carrier.

Other acceptable three-dimensional, osteoconductive scaffolds that can be used in accordance with embodiments of the present invention may be prepared from materials including: (i) biologically derived (e.g., silk, cellulose, starch) and synthetic biodegradable polymers/copolymers scaffolds (e.g., PLA/PGA, PCL, and/or PHB, for instance, formed as a bead or a woven scaffold); (ii) biocompatible, bioresorbable fibers, such as glass fibers; and (iii) other biodegradable matrices, such as biodegradable metals (Mg based preforms).

In addition to the biologically acceptable carrier component having a three-dimensional, open-porosity, osteoconductive scaffold, the bone void filler compositions in accordance with embodiments of the present invention also contain an osteoinductive component containing DMB and an acidic mineral component, which have been previously described herein. In accordance with this embodiment, exemplary acidic mineral components contain DiCal.

In accordance with certain of embodiments of the present invention, the relative concentrations of osteoinductive component containing DMB, acidic mineral component, and three-dimensional, porous, osteoconductive scaffold component may be optimized for a particular clinical application. Notwithstanding the foregoing, particularly useful bone void filler compositions in accordance with certain embodiments are obtained by using specified ranges of the components. Specifically, the inventors have found that certain ratios of acidic mineral component relative to the amount of collagen, as biologically acceptable carrier, provide unexpected increases in bone growth potential. In certain embodiments, an acidic mineral component (e.g., DiCal), is used in the range of about 1% to about 60% by weight relative to the combined weight of acidic mineral component and the total weight of collagen, accounting for collagen contained in the carrier as well as any collagen found in other components, including the DMB, which was assumed for purposes of experimentation to be 90% by weight collagen. In some embodiments, the acidic mineral component is used in the range of about 1% to about 50%, from about 1% to about 30%, from about 1% to about 20%, and from about 1% to about 10%. In certain embodiments, calcium acetate as a mineral component alone or calcium acetate combined with a phosphate salt (e.g., calcium hydrogen phosphate and trisodium phosphate) is used in the range of about 1% to about 60% by weight relative to the combined weight of mineral salt and the total weight of collagen, accounting for collagen contained in the carrier as well as any collagen found in other components, including the DMB, which was assumed for purposes of experimentation to be 90% by weight collagen. In some embodiments, the mineral component is used in the range of about 1% to about 50%, from about 1% to about 30%, from about 1% to about 20%, and from about 1% to about 10%.

Effective mass ratios of a DMB component to acidic mineral component, as determined in rat ectopic assays, range from about 0.5:1 to about 80:1. In some embodiments, effective mass ratios of DMB component to acidic mineral component range from about 1:1 to about 40:1, from about 1:1 to about 16:1, from about 1:1 to about 8:1, from about 5:1 to about 9:1, and from about 1:1 to about 4:1. In some embodiments, the dry weight percentages of the acidic mineral component (e.g., DiCal) range from about 0.5% to about 60%, the osteoinductive component (e.g., DMB) range from about 35% to about 90%, and the carrier component (e.g., collagen) range from about 3.5% to about 30%. In some embodiments, the dry weight percentages of the acidic mineral component (e.g., DiCal) range from about 9% to about 40%, the osteoinductive component (e.g., DMB) range from about 55% to about 90%, and the carrier component (e.g., collagen) range from about 5% to about 30%. In some embodiments, the dry weight percentages of the acidic mineral component (e.g., DiCal) range from about 9% to about 25%, the osteoinductive component (e.g., DMB) range from about 70% to about 90%, and the carrier component (e.g., fibrillar collagen) range from about 5% to about 20%. In one embodiment, the DMB to DiCal ratio is about 7 to about 8. In one embodiment, the volume (mL) of acid solution, e.g., 30 mM HCl, per mass (g) of collagen is about 33 to about 35.

Processes for producing bone void filler compositions in accordance with one embodiment of the invention in the form of sponges, and subsequently producing pastes or putties, e.g., from particulated sponge, are not generally limited and include those methods known in the art. In one method, an acid solution, e.g., a hydrochloric acid containing solution, is added to collagen to wet the collagen. Acidic mineral, e.g., DiCal, is added and the combination is mixed thoroughly with a spatula. The combination is then whipped with a lab scale mixer to obtain a composition with a gel-like consistency. As used in the present invention, the term "gel" generally refers to a jelly-like, thick, soft, partly liquid substance. In general, a gel may be extruded without substantial mechanical deterioration through at least a 13 gauge syringe needle. DMB powder is then added to the collagen-acidic mineral gel and mixed with a spatula to form a collagen-acidic mineral-DMB dispersion. In one embodiment, DMB particles are added simultaneously with collagen, mineral and acid solution. The sponge is obtained from a process in which the collagen-acidic mineral-DMB dispersion is placed in a mold of a desired shape and thereafter frozen and lyophilized. The sponge may be cast in any desired shape, including strips, discs, sheets, bullets, cylinders, wedge, trough, anatomic shapes such as an alveolar ridge, etc. The types of collagen that may be used are described above and include bovine dermal fibrillar collagen.

In one method, collagen (e.g., fibrillar), acidic mineral (e.g., DiCal) and DMB (e.g., particles) are simultaneously added to an acidic solution (e.g., a hydrochloric acid solution) and whipped with a lab scale mixer to obtain a composition.

The collagen-acidic mineral-DMB composition is placed in a mold of a desired shape and thereafter frozen and lyophilized to form a sponge. The sponge may be cast in any desired shape, including strips, discs, sheets, bullets, cylinders, etc. The types of collagen that may be used are described above and include bovine dermal fibrillar collagen.

In one method, hydrochloric acid is added to collagen and gelatin. An acidic mineral, e.g., DiCal, is added to that mixture and the combination is mixed thoroughly with a spatula. The combination is then whipped with a lab scale mixer to obtain a composition. DMB powder is then added to the collagen-gelatin-acidic mineral composition and mixed with a spatula. The collagen-gelatin-acidic mineral-DMB composition is placed in a mold of a desired shape and thereafter frozen and lyophilized to form a sponge. The sponge may be cast in any desired shape, including strips, discs, sheets, bullets, cylinders, etc. The types of collagen that may be used are described above and include bovine dermal fibrillar collagen.

As indicated, preparation of the bone void filler compositions in accordance with some embodiments may involve freezing and lyophilization. In certain such embodiments, the composition may be frozen at −20 to −80° C. for about two hours. Freezing may be conducted in a single or multiple steps. In certain such embodiments, the composition may be lyophilized for at least about sixteen hours. In other embodiments, the composition may be lyophilized for at least about 48 hours.

After lyophilization, the bone void filler composition, now in the form of a rectangular sponge or other desired shape, may be subjected to crosslinking. Crosslinking may be accomplished by a variety of methods known to one skilled in the art, including but not limited to dehydrothermal (DHT) crosslinking, UV light exposure, and chemical crosslinking with aldehydes (e.g., glyceraldehyde, formaldehyde, and glutaraldehyde), carbodiimides and various amino acids. In DHT crosslinking, the composition is placed in a vacuum oven chamber, the chamber is evacuated to create a vacuum, and the composition is heated for a period of time. In one embodiment, the composition is heated to about 110° C. In one embodiment, the composition is heated in a vacuum oven for about 48 hours.

Following freezing, lyophilization, and any optional crosslinking, the solid composition can be, as has been previously described, in the form of a sponge. The sponge may be combined with a liquid carrier, as previously described, and then manipulated, e.g., molded, into a desired shape and applied to a defect site. In one embodiment, the sponge may be rehydrated and an additional collageneous biologically acceptable carrier added thereto to obtain a paste or putty of a desired consistency. In one embodiment, the carrier comprises gelatin, denatured DMB and/or collagen, which carrier may bind to a fibrillar collagen structure (e.g., one found in a rehydrated sponge). A collagenous carrier may be prepared by heating collagen, e.g., from about 5% to about 15% (w/v) or about 10 to 30% (w/v) collagen, in an aqueous solution, e.g., saline (e.g., 0.9% w/v) to over 100° C. (e.g., about 121° C.) for about an hour. A gelatin containing carrier solution may be prepared by dissolving gelatin powder in an aqueous solution (e.g., water) to about 5 to about 15% (w/v) gelatin. Dissolved or partially solubilized carriers may be maintained at about 37° C. to about 50° C. prior to putty or paste formation. For example, a sponge is rehydrated with a liquid carrier and excess moisture is removed, then a carrier is added and blended to form a putty that may be packed into a container or introduced to a delivery device (e.g., syringe) or dehydrated. In one embodiment, the carrier that is added to the rehydrated sponge is from the same source as the collagen in the sponge but is heat denatured. In one embodiment, the source of carrier in the sponge and the subsequently added carrier are different. In one embodiment, a putty of the invention includes two or more types of carrier, e.g., a combination of fibrillar collagen and gelatin.

Alternatively, the sponge may be particulated, shredded or otherwise disaggregated as previously described and then combined with a liquid carrier, as previously described, to obtain a paste or putty of a desired consistency. Methods of forming particles are known to one skilled in the art and include, but are not limited to, grinding, milling, chopping, and/or molding. In certain embodiments, particles are formed by milling the solid composition. Milling may occur using a Wiley mill (Thomas Scientific, Swedesboro N.J.). The mesh size on the mill directs the size of the resultant particles. In one embodiment, a −20/+140 meshes are used that creates particles in the range of about 100 μm to about 840 μm. The particles may be sized, for example, by sieving. At any point in the process, additional components may be added to the composition, as described above, including bulking agents (e.g., bone chips).

The bone void filler compositions of the invention may be prepared under sterile conditions and/or using sterile components, and/or sterilized once a sponge, paste or putty is obtained, e.g., to reduce or eliminate the introduction of microbes including viruses upon implantation. In one embodiment, a sponge, paste or putty of the invention or individual components thereof is subjected to irradiation, e.g., gamma irradiation, for instance 30 kGy, at low temperatures, and/or in an inert environment, or low dose electron beam (E beam), or chemical sterilization, e.g., using ethylene oxide or gas plasma.

The on-site preparations that are obtained in accordance with the one embodiment of the present invention have the advantage of allowing the clinician to vary the concentrations and quantities of bone void filler composition (sponge or particulates) and liquid carrier to obtain desired handling characteristics. On-site preparation also permits the addition of optional components at the discretion of the clinician.

The bone void filler compositions in accordance with certain embodiments desirably have a pH as delivered to the defect site of from about 2 to about 7, e.g., from about 3 to about 5 or from about 5 to about 7. It has been found that when the pH is within the limitations identified above, the materials have excellent physical properties, such as a putty consistency which is elastic and dough-like (see e.g., US20080293617, US20060246150 and US20080152687 incorporated by reference herein). At higher pH, the materials may become crumbly with the consistency of wet sand. A putty consistency is desired because it provides many benefits such as enhanced cohesiveness, ease of handling and moldability. Because materials of the present invention are cohesive, they are also believed to provide the benefit of maintaining an active compound at the site of implantation longer than comparative materials with less cohesiveness.

The bone void filler composition may be provided as a kit. Acceptable kits may include one, two, three or four receptacle-containers, one of which may be suitable for combination and/or "hydration" of the components. In one such embodiment, the kit includes the particulated bone void filler composition described above. The kit may further have a mixing implement such as a spatula, stir rod, etc., a disposable syringe barrel with or without a cannulated extension (e.g., a needle) in which to place and deliver the mixed paste, one or more instruments for implanting the composition, instructions for formulating and/or using the composition, etc.

As previously taught herein, in accordance with one embodiment, a bone void filler composition is provided in the form of a pre-mixed paste or putty. The bone void filler compositions of this group of embodiments thus contain an osteoinductive component containing DMB; an acidic mineral component; and a liquid carrier as a biologically acceptable carrier component. The relative amounts of each component may be optimized for a particular clinical application, which may vary according to differences in patient age, gender, health, systemic conditions, habits, anatomical location, etc. However, as will be explained in greater detail herein, the present inventors have found that particularly useful bone void filler compositions are obtained with the use of specified ranges of the components.

The bone void filler compositions of one of the embodiments of the invention are prepared using a liquid carrier. The liquid carriers that can be used to form the pastes or putties of this embodiment of the present invention may be selected from those liquid carriers previously described for use in preparing the bone void filler compositions. As previously described, these liquid carriers are desirably biological fluids, such as bone marrow aspirate, whole blood, blood components (e.g., serum, plasma, platelet rich plasma), etc. Other liquid carriers may include buffers, which may be desirable to buffer the composition to the physiological pH values of human serum (pH 7.1 to pH 7.4), e.g., before combining with an acidic mineral component. Examples of buffers are known to those skilled in the art and include Tris and phosphate-buffered saline. More than one liquid carrier, for example, bone marrow aspirate and a buffering solution, may be used. The liquid carrier may include water or saline, and components such as solubilized collagen, glycerin, glycerol, lecithin, surfactants, carboxylic acids, dimethylsulfoxide, and/or tetrahydrofuran. Collagen is commonly solubilized using an acid treatment. When solubilized collagen is employed as a liquid carrier, it may be desirable to remove any residual acid present in the collagen. Additionally, natural and synthetic polymers such aliphatic polyesters, polyethylene glycols, polyanhydrides, dextran polymers, and/or polymeric orthophosphates may be included in the composition. The carrier may also be prepared using other materials including biologically derived (e.g., silk, cellulose, starch) and synthetic biodegradable polymers/copolymers (e.g., PLA/PGA, PCL, PHB). In one embodiment, the liquid carrier may promote cellular infiltration and retain the composition at the defect site, without being cytotoxic. The liquid carrier may promote such cellular infiltration by providing a molecular matrix for cell migration.

In accordance with this embodiment, exemplary acidic mineral components contain DiCal. Particularly useful pre-mixed bone void filler compositions are obtained with the use of specified ranges of the components. Specifically, effective mass ratios of demineralized bone component to acidic mineral component range from about 0.5:1 to about 80:1. In some embodiments, effective mass ratios of demineralized bone component to acidic mineral component range from about 1:1 to about 40:1, from about 1:1 to about 16:1, from about 1:1 to about 8:1, from about 5:1 to about 9:1, and from about 1:1 to about 4:1. In some embodiments, ratios of acidic mineral component relative to the amount of demineralized bone matrix collagen range from about 2.5:1 to about 7.5:1 provide unexpected increases in bone growth potential.

Processes for producing bone void filler compositions in accordance with this embodiment of the invention in the form of pastes or putties are not generally limited and include those methods known in the art. In one embodiment, a number of components including DMB and acidic mineral components are combined with a sufficient quantity of liquid carrier to achieve a bone void filler composition of a desired consistency, e.g., a paste or putty. Alternatively, a sponge is combined with a collagenous carrier which is suspended or dissolved in a liquid, to achieve a bone void filler composition of a desired consistency, e.g., a paste or putty. As a putty or paste, the composition desirably has suitable rheological properties (e.g., viscosity) so as to be injectable through applicators including large gauge applicators, such as catheters, or syringes, while largely remaining at the implant site.

The bone void filler compositions in accordance with this embodiment desirably have a pH as delivered to the defect site of from about 2 to about 7, e.g., from about 3 to about 5 or from about 5 to about 7. It has been found that when the pH is within the limitations identified above, the materials have excellent physical properties, such as a putty consistency which is elastic and dough-like. At higher pH, the materials may become crumbly with the consistency of wet sand. A putty consistency provides many benefits such as enhanced cohesiveness, ease of handling and moldability. Because materials of the present invention are cohesive, they are also believed to provide the benefit of maintaining an active compound at the site of implantation longer than comparative materials with less cohesiveness.

In accordance with bone void filler compositions of the present invention, there is also provided methods for using the bone void filler compositions to promote bone growth. In accordance with such embodiments, the bone void filler composition, in the desired form, is applied to a desired anatomical site of the patient, e.g., the bone defect site. Bone void filler compositions in accordance with the present invention in the form of a sponge are combined with a liquid carrier, pre-molded or molded or otherwise formed into a desired shape generally conforming to the shape and size of the defect site, and then positioned adjacent or pressed, either manually and/or using instrumentation, into the defect site. Bone void filler compositions in accordance with the present invention in the form of a putty, either resulting from the combination of particulated sponge and a liquid carrier or a ready-to-use putty, are molded or otherwise formed into a desired shape generally conforming to the shape and size of the defect site, and then positioned adjacent to or pressed, either manually and/or using instrumentation, into the defect site. Bone void filler compositions in accordance with the present invention in the form of a paste, either resulting from the combination of particulated sponge that has been combined with a liquid carrier or a ready-to-use paste, are applied to the defect site. If the paste is injectable, the paste may be loaded into the barrel of a disposable syringe, with or without a cannula (e.g., needle) attached, and is extruded through the barrel aperture to the desired anatomical site.

In accordance with the methods of the invention, a defect site is desirably prepared to expose healthy bleeding bone, facilitating subsequent bone growth. The methods may be performed using minimally invasive procedures known to one skilled in the art. The methods may be used in at least partially filling bone voids and/or gaps of the skeletal system. Such applications include induction of bone formation for hip replacement operations, knee replacement operations, spinal fusion procedures, repair of periodontal defects, treatment of osteoporosis, repair of bone tumor defects, dental procedures, repair of cranial maxilla facial defects, and repair of bone fractures or defects. These voids and/or gaps may be a result of a development failure, degeneration or trauma, either natural or by surgical creation. The bone void filler composition is resorbed by the body during the healing process (over days, weeks, and months).

The invention will be further described by the following non-limiting examples.

Example 1

Intramuscular Implant Evaluations

To determine if the addition of DiCal would enhance bone growth in implanted DBM containing compositions, various test samples, as described below were implanted intramuscularly in athymic rats. Surgery on each rat was performed as follows. Prior to the surgery, the rats were anesthetized by intraperitoneal injection of ketamine/Xylazine solution; 70 mg/kg of ketamine and 5 mg/kg of xylazine. General anesthesia was noted by a lack of response to a toe pinch. Anesthesia was maintained with isoflurane, if needed.

The skin over the semitendinosus muscle was shaved (if necessary) using an electric clipper and prepared with chlorhexadine and alcohol scrub. The rat was placed in lateral recumbency. Using a scalpel or scissors, a 1 cm incision was made in the skin in line with the long bone. Two 2 mm incisions were made in the semitendinosus muscle and blunt dissection used to prepare the implant bed.

Using aseptic technique, each test sample allocated for intramuscular implantation was placed in the semitendinosus muscle. A few drops of sterile saline were used, as necessary, on the implantation site before inserting the implant to assist in placement of the test sample at the placement site. The rat was then re-positioned to the other side and the procedure repeated. Each opening was closed with appropriate suture and skin wound closure was completed using stainless steel wound clips. FIG. 1 is a representation of a rat showing positions of the intramuscular implants.

Puros® DBM was used as the carrier and the source of DMB for all systems evaluated in this example. Four different systems were evaluated: system 1(a) containing Puros® DBM (25 mg); system 1(b) containing Puros® DBM (25 mg) and BMP-2 (10 micrograms); system 1(c) containing Puros® DBM (12.5 mg) and DiCal (12.5 mg); and system 1(d) containing Puros® DBM (12.5 mg), DiCal (12.5 mg) and BMP-2 (10 micrograms). For systems containing DiCal, DiCal was employed in a 1:1 ratio (i.e., DiCal dry wt.:Puros® DBM wet wt.) and a 2500:1 ratio (i.e., DiCal dry wt.:BMP-2 dry wt.). The samples were generally prepared as follows. The components were combined (e.g., the DiCal was mixed with the wet Puros® DBM putty) by hand using a spatula so as to evenly distribute the components. The compositions were then subjected to freezing conditions at −80° C. for 30 minutes. Thereafter, the compositions were subject to lyophilization for at least 24 hours. 25 mg of each sample system was then placed into gelatin capsules and implanted intramuscularly as described above.

Figure 2:
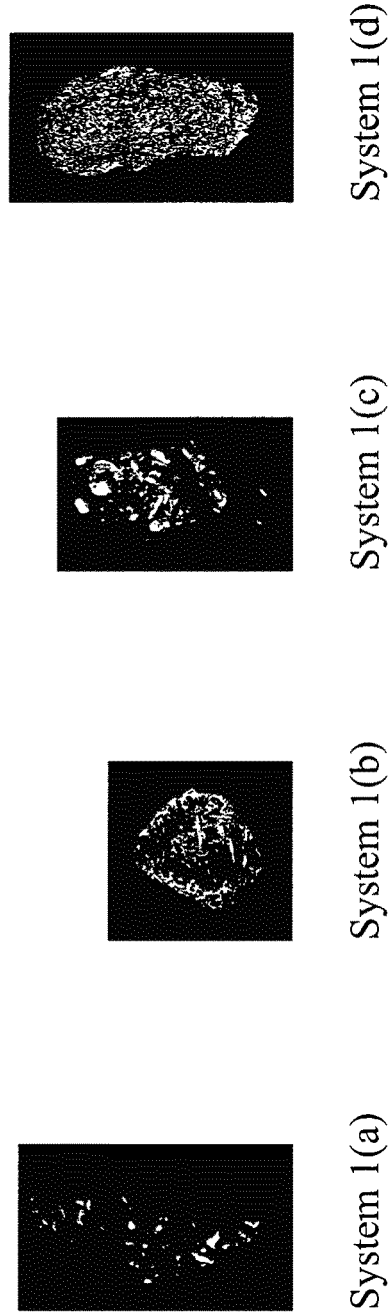
FIG. 2 depicts micro-CT scans obtained in studies evaluating bone growth from intramuscular implants in athymic rats.

After 28 days, tissue containing each implant was removed for evaluation, including micro-CT scans. For the micro-CT evaluations, these explants were fixed in formalin. The micro-CT scans are depicted in FIG. 2 and data derived therefrom in Table 1. The micro-CT scans and derived data show that the presence of DiCal markedly enhanced bone formation in systems with BMP (e.g., an approximately 83% increase in total bone mineral deposition). The data in Table 1 summarizes the bone volume, bone mineral density and bone volume/total volume for the four groups. As expected, bone volume and the ratio of bone volume (mineralized)/total volume increased when BMP-2 was added (compare 1(a) and 1(b), and 1(c) and 1(d)). The ratio of bone volume/total volume also increased when DiCal was added (about 3 fold; compare 1(a) to 1(c)), although not to the same extent as BMP-2 containing compositions. While only one concentration of DiCal was tested, the results in Table 1 indicate that DiCal provides for an increased ratio of mineralized bone volume/total volume in the absence of exogenous BMP-2.

TABLE 1

| System | Bone Volume (mm³ ± SD) | Bone Mineral Density (mg hydroxyapatite/cc ± SD) | Bone Vol/Total Vol ± SD |
|---|---|---|---|
| 1(a) | 2.65 ± 3.06 | 565 ± 124 | 0.03 ± 0.02 |
| 1(b) | 31 ± 15 | 454 ± 17 | 0.375 ± 0.08 |
| 1(c) | 2.65 ± 1.94 | 512 ± 41 | 0.10 ± 0.15 |
| 1(d) | 52 ± 33 | 496 ± 27 | 0.198 ± 0.11 |

Example 2

Subcutaneous Implant Evaluations

Various systems, as described below, were implanted subcutaneously in athymic rats to evaluate the compositions with respect to their efficacy for bone growth. Male athymic rats, about seven weeks old at the commencement of the study, were used. Surgery on each rat was performed as follows. Prior to the surgery, the rats were anesthetized by intraperitoneal injection of ketamine/Xylazine solution; 70 mg/kg of ketamine and 5 mg/kg of xylazine. General anesthesia was noted by a lack of response to a toe pinch. Anesthesia was maintained with isoflurane, if needed.

Figure 3:
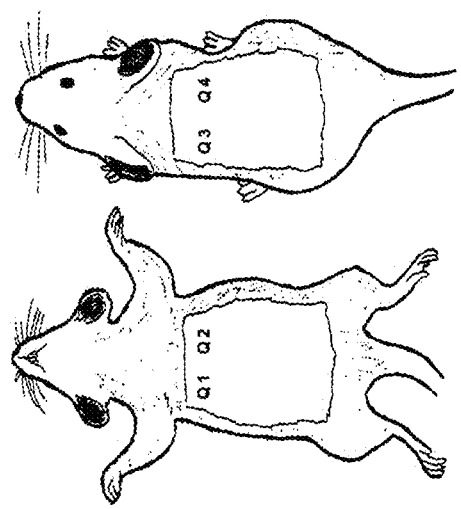
FIG. 3 is a representative image of rat ventral and dorsal views illustrating implant locations Q1-Q4 used in studies evaluating bone growth obtained from subcutaneous implants in athymic rats.
Figure 4:
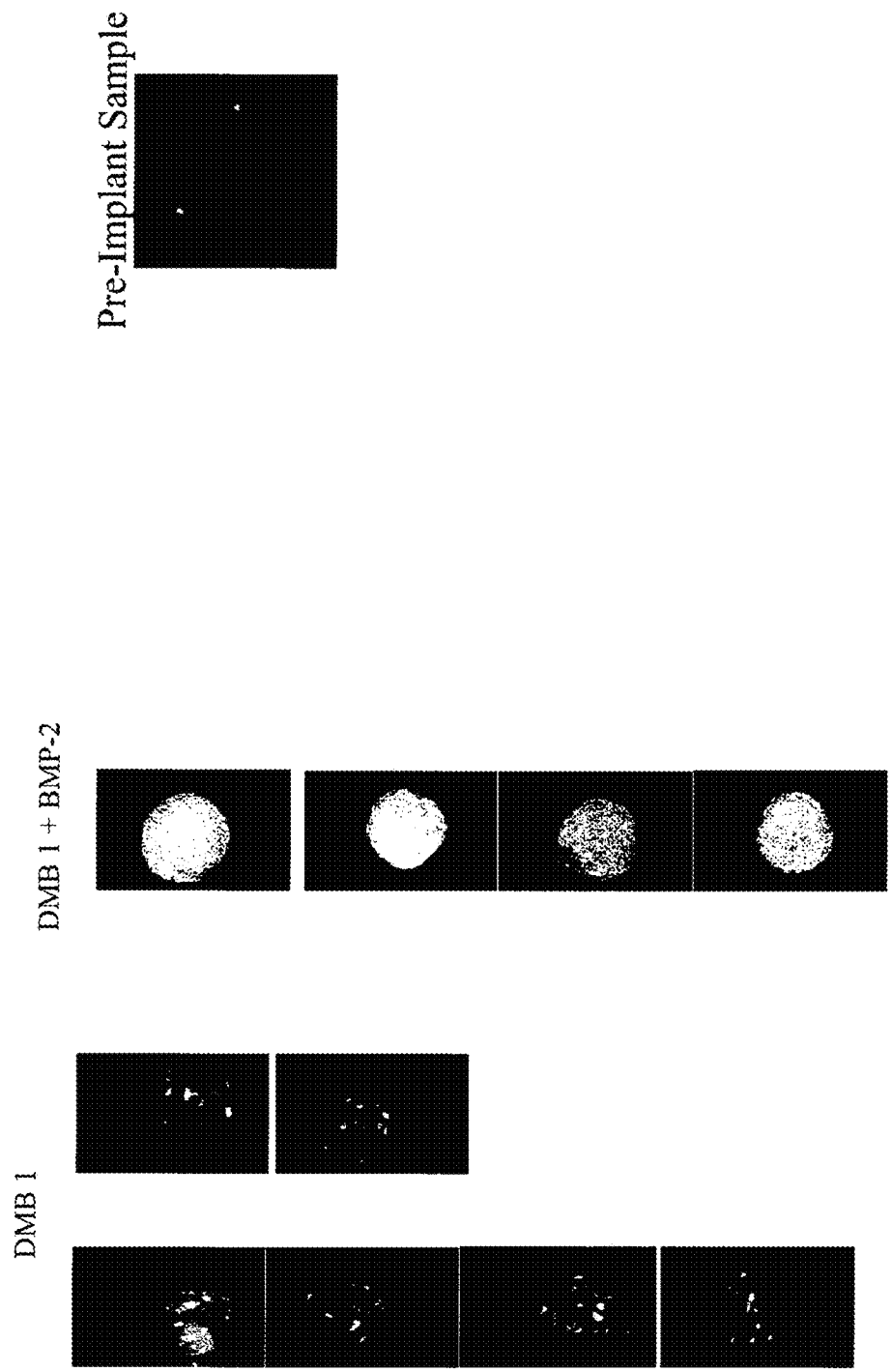
FIG. 4 depicts micro-CT scans obtained in studies evaluating bone growth from subcutaneous implants in athymic rats.
Figure 5:
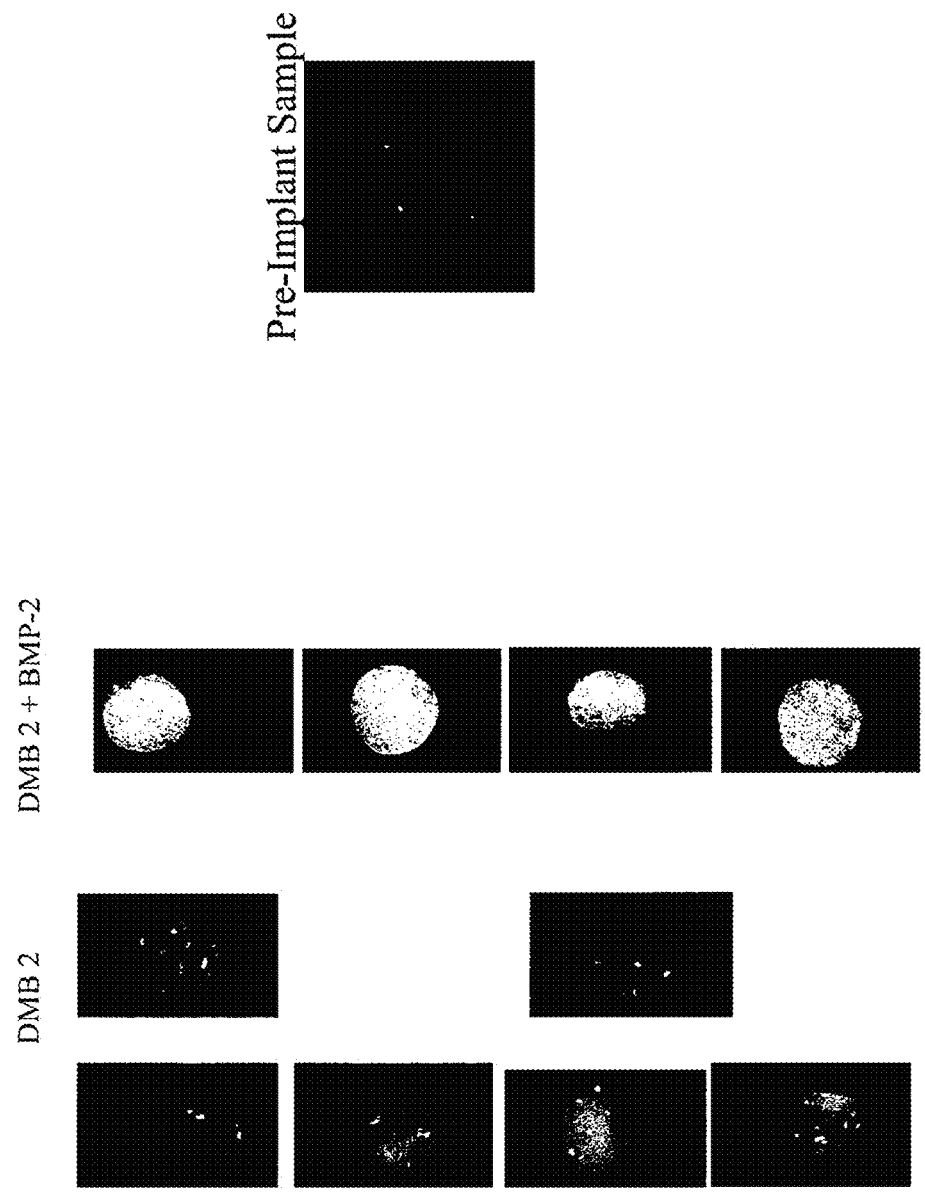
FIG. 5 depicts micro-CT scans obtained in studies evaluating bone growth from subcutaneous implants in athymic rats.
Figure 6:
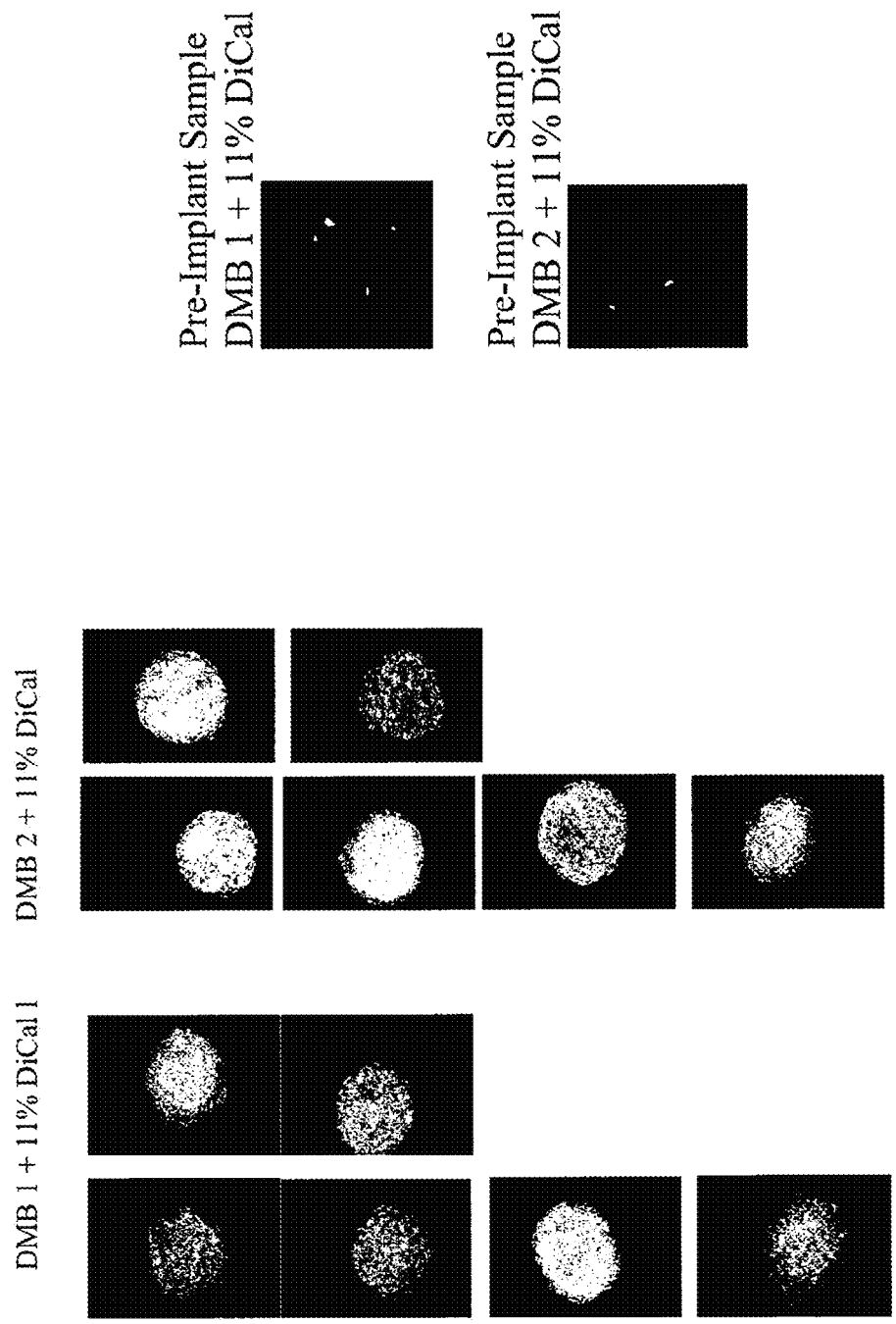
FIG. 6 depicts micro-CT scans obtained in studies evaluating bone growth from subcutaneous implants in athymic rats.
Figure 7:
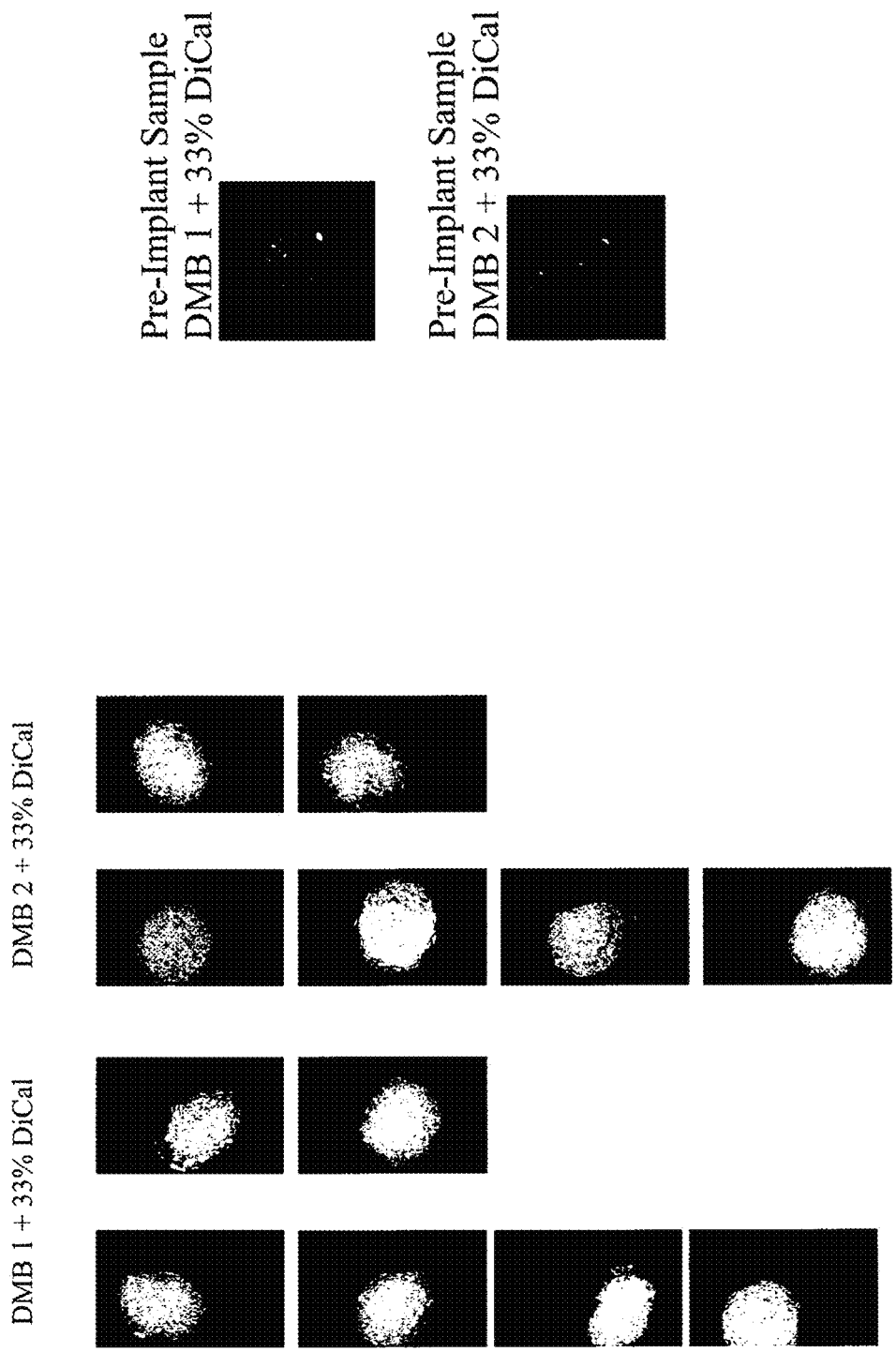
FIG. 7 depicts micro-CT scans obtained in studies evaluating bone growth from subcutaneous implants in athymic rats.
Figure 8:
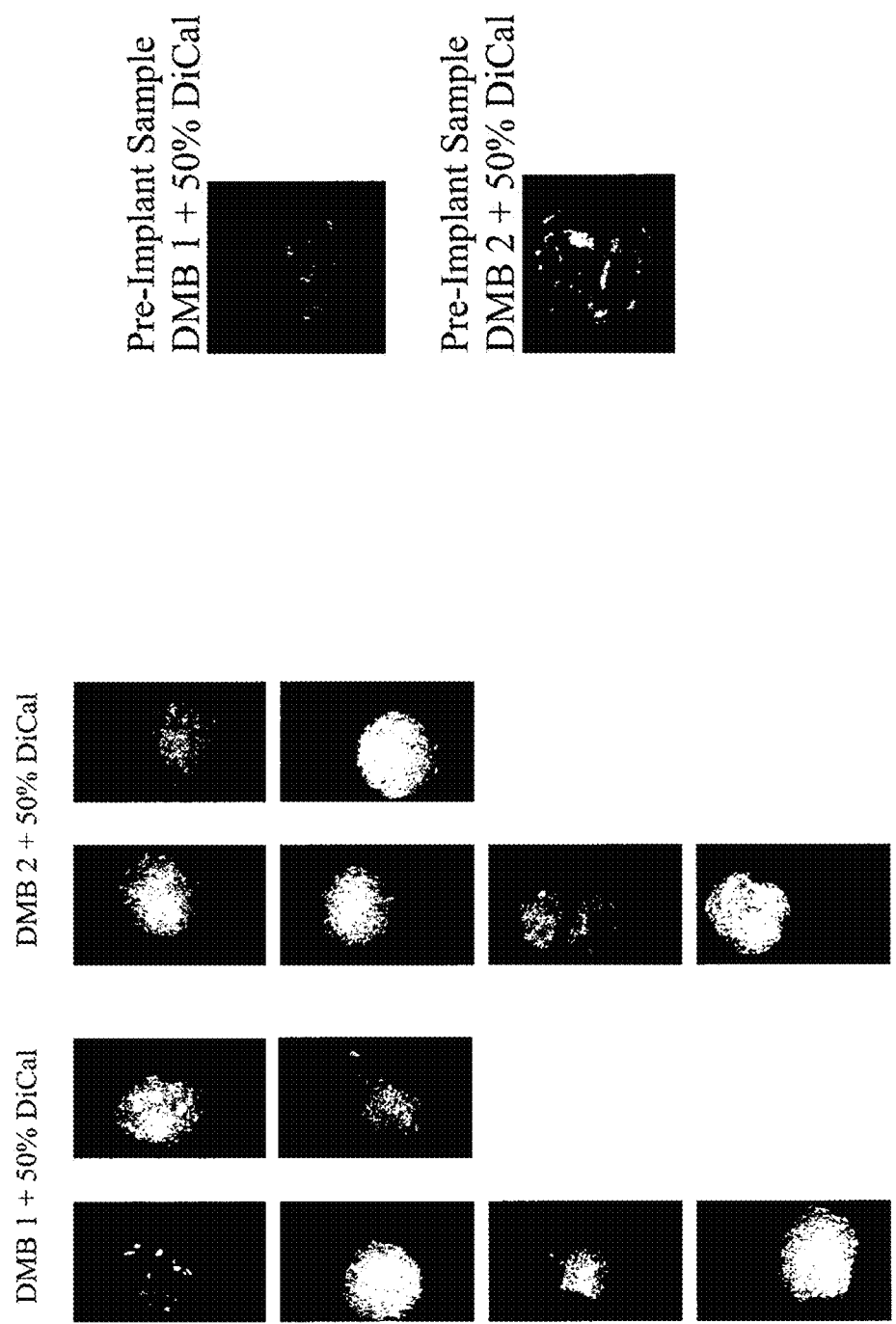
FIG. 8 depicts micro-CT scans obtained in studies evaluating bone growth from subcutaneous implants in athymic rats.
Figure 9:
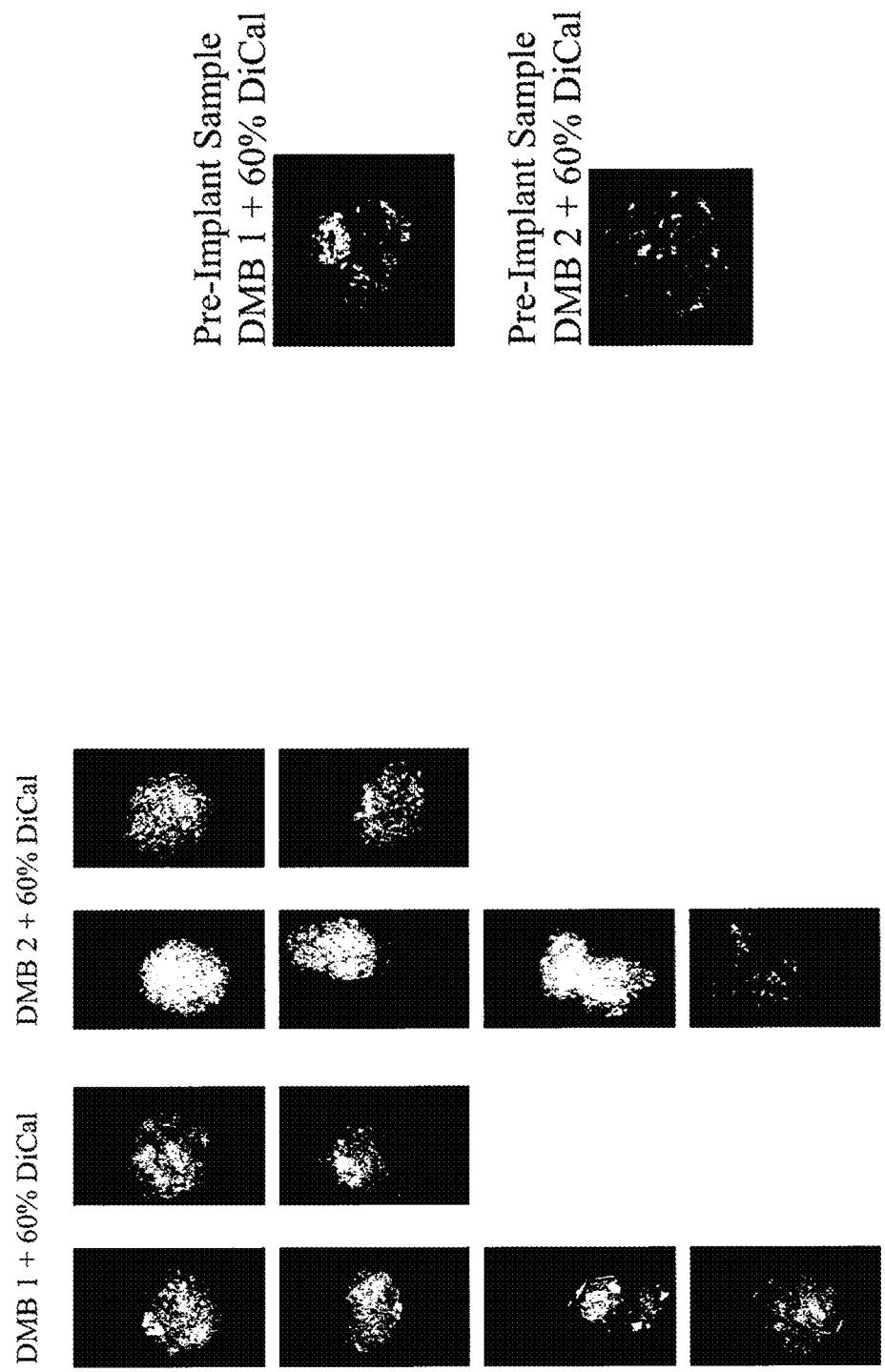
FIG. 9 depicts micro-CT scans obtained in studies evaluating bone growth from subcutaneous implants in athymic rats.

The ventral and dorsal thoracic area of each rat was swabbed with chlorhexadine and alcohol scrub. Using a scalpel or scissors, a 1 cm incision was made in the skin on the right side. This ventral incision was made at the base of the rib cage. After incision, a pocket was prepared beneath the skin and above the incision by blunt dissection towards the axilla. A large blood vessel (cranial thoracodorsal vein) was noted which was often adhered to the skin/subcutaneous tissues. The right ventral implant was placed in the pocket of the subcutaneous tissue approximately 5 mm anterior to the incisions on the chest wall directly below the cranial thoracodorsal blood vessel. When the right ventral side was implanted, the left side had the same procedure done for implantation. The rat was then re-positioned to make two more small (1 cm) incisions in the skin of the dorsal thorax. The two dorsal implants were placed toward the middle of the rib cage. All wound closure was accomplished using either stainless steel wound clips or sutures. Thus, each rat had four subcutaneous implants with bilateral placements of the test articles in each of the ventral and dorsal thoracic regions. FIG. 3 is a representative image of a rat ventral and dorsal views depicting subcutaneous implant sites Q1-Q4.

Three different types of systems were evaluated: implants containing collagen and DMB, implants containing collagen, DMB, and BMP-2, and implants containing collagen, DMB, and varying amounts of DiCal. Nominal DiCal concentrations evaluated were 11, 33, 50, and 60 weight percent relative to the combined weight of acidic mineral component and the total weight of collagen, accounting for collagen contained in the carrier as well as any collagen found in other components, including the demineralized bone, which was assumed for purposes of experimentation to be 90% by weight collagen. Two lots of the same DMB, were provided by RTI Biologics, Inc.

Implants were generally prepared as follows. Hydrochloric acid (30 mM) was added to the collagen to wet the collagen. The combination was then whipped with a lab scale mixer to obtain composition with a gel-like consistency. The appropriate amount of DMB powder was added and mixed thoroughly with a spatula to obtain a putty-like consistency. Discs of a desired shape residing on a glass plate were filled with the putty. A second glass plate was positioned over the discs and clamped into place. The glass plate assembly was frozen, generally for a minimum of one hour at −80° C. The discs were removed from the freezer and excess material was trimmed from the disc molds. The glass plate assembly was quickly returned to the freezer again for a minimum of one hour at −80° C. The assembly was then subjected to lyophilization for a minimum of 12 hours. The individual, now sponge, implants were then recovered from the molds.

For implants intended to contain DiCal, the appropriate amount of DiCal was added to the combination of hydrochloric acid and collagen prior to the whipping step. The combination of collagen, hydrochloric acid, and DiCal was first mixed with a spatula and then whipped with a mixer.

For implants intended to contain BMP-2, 20 µL of reconstituted BMP-2 was added to one side of the lyophilized sponge implant disc. The BMP-2 solution was allowed to soak into the sponge implant disc. The sponge implant disc was subjected to freezing conditions for one hour at −80° C. The assembly was then subjected to lyophilization for a minimum of 12 hours. The individual, now sponge, implants were then recovered. Then, 20 µL of reconstituted BMP-2 was added to the other side of the sponge implant disc and the procedure was repeated.

Figure 10:
FIG. 10 depicts histology results obtained in studies evaluating bone growth from subcutaneous implants in athymic rats. DM=demineralized matrix; MM=mineralized matrix from the original graft; RM=re-mineralized matrix with osteoclasts (OC), indicative of bone formation.
Figure 12:
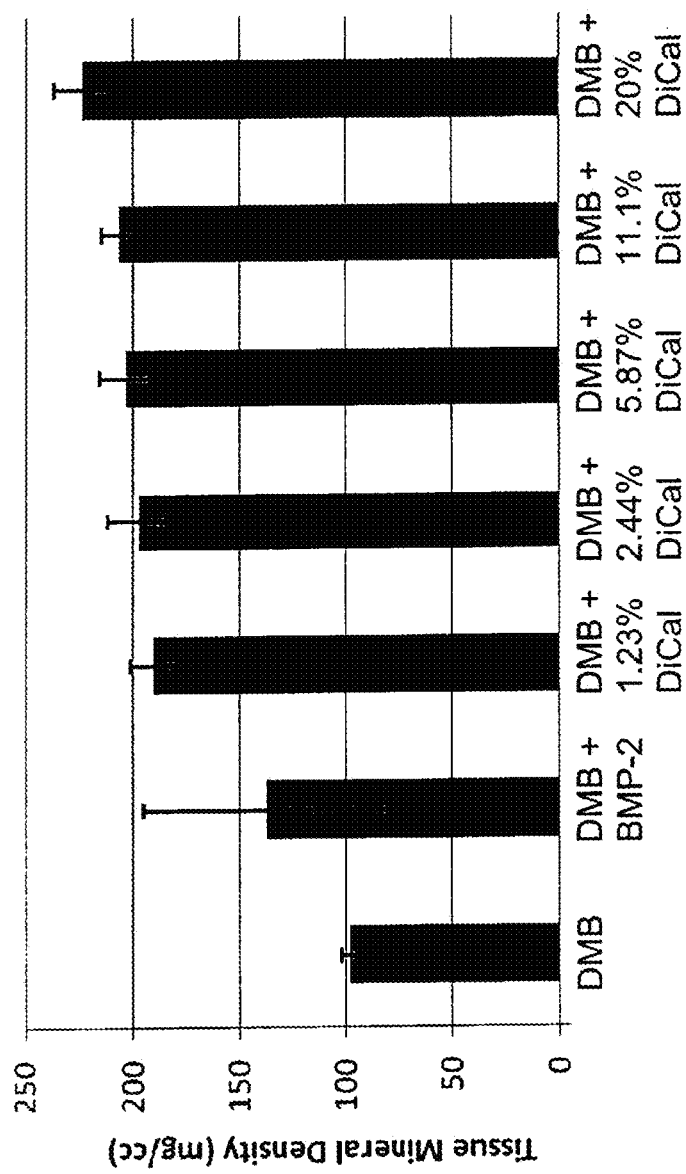
FIG. 12 depicts mineral density results obtained in studies evaluating bone growth from subcutaneous implants in athymic rats.

After 21 days, the implants were removed for evaluation, including micro-CT and histological evaluation. The explants were fixed in 10% NBF and radiographed. Following radiography, the samples were subjected to micro-CT. The micro-CT scans are depicted in FIGS. 4-9. Each group of micro-CT scans in FIGS. 4-9 depict explants taken from various locations Q1-Q4 of various test subjects. The CT-scans show that the presence of DiCal enhanced bone formation at each of the concentrations evaluated. Histological analysis showed that the presence of DiCal also resulted in increased vascularization. FIG. 10 is representative and shows that an implant containing collagen, DMB, and 11% DiCal showed increased vascularization and the activation of both osteoclasts and osteoblasts compared to an implant containing only collagen and DMB. In addition, FIG. 11 shows a marked increase in vascularization at DiCal concentrations ranging from 11%-60%. Moreover, FIG. 12 demonstrates, for similarly prepared samples, the mineral density enhancement associated with the addition of DiCal concentrations ranging from 1.23% to 20%.

Example 3

Exemplary Putty Composition Preparation

Figure 13:
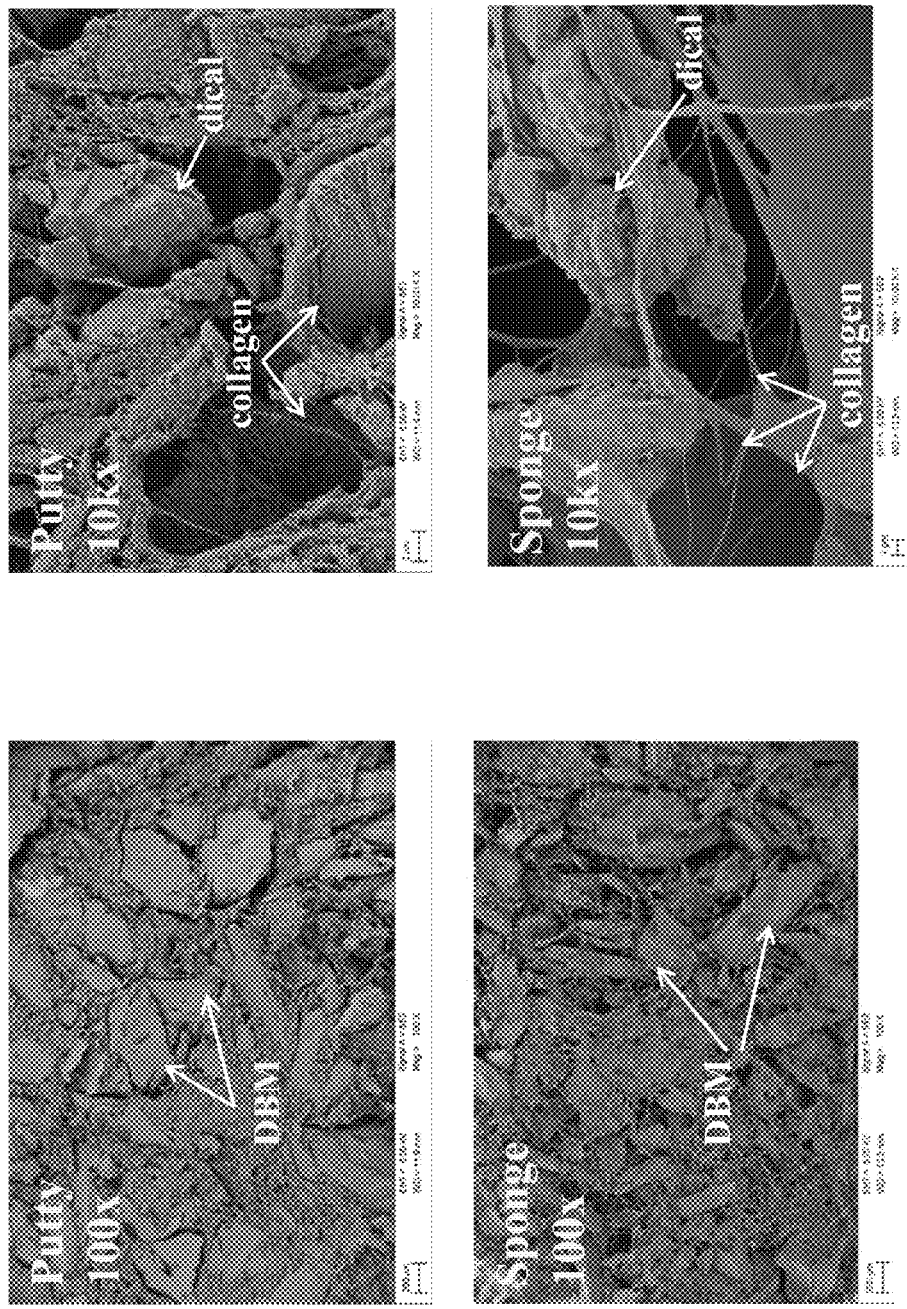
FIG. 13 shows micrographs of the structure of an exemplary putty composition of the invention (100 x and 10 kx) versus a sponge composition of the invention (100 x and 10 kx).

In this example, gelatin was combined with fibrillar collagen, a source of calcium and phosphate and DMB particles to form a putty. A demineralized bone matrix sponge was prepared by whipping 0.18 gram of collagen, 7.3 mL 30 mM hydrochloric acid, 0.21 gram calcium phosphate dibasic (Dical), and 1.6 gram demineralized bone particle into a slurry, followed by lyophilization of the slurry into a 5 cm by 2 cm by 0.5 cm sponge. A 12% w/v gelatin solution was prepared by adding 1.2 gram gelatin into 10 mL water at about 37° C. to about 50° C. The prepared sponge was then soaked with water for about 10 minutes to about 30 minutes. After absorbing the water, the sponge was compressed to remove the excess water. 1.9 mL of 12% gelatin (at about 37° to about 50° C.) was then added to the sponge, spread and blended with the sponge using a spatula. After 10 minutes, the mixture became a putty like material. This putty material is cohesive and malleable, held its shape and did not wash away (disintegrate) after soaking in water. SEM imaging (FIG. 13) showed that this putty material has fibrillar collagen and a three-dimensional porous structure.

The putty may be employed in any clinical or surgical applications where bone void filler, demineralized bone matrix and bone growth factors have been employed, particularly to repair or reconstruct muscular skeleton in a non-weight bearing site. For example, the product can be extruded from a syringe directly onto a defect site or molded into different contour or shape to fit into a surgical site.

Example 4

Exemplary Putty Composition Preparation

In this example, heat denatured collagen is combined with fibrillar collagen, a source of calcium and phosphate and DMB particles to form a putty. A DMB sponge was prepared by whipping 0.125 gram of collagen, 5.4 mL 30 mM hydrochloric acid, 0.156 gram calcium phosphate dibasic (Dical), and 1.25 gram demineralized bone particle into a slurry, followed by lyophilization of the slurry into a 1.2 cm by 0.3 cm by 15 cm sponge. 12% w/v collagen in 0.9% w/v saline or water was heated to 121° C. for 1 to 2 hours to denature the collagen and bring the collagen into solution. 1.2 cm×0.3 cm×4 cm portion of the sponge described above was then soaked with water for 10 minutes. After absorbing the water, the sponge was hand compressed to remove the excess water, and then 0.8 mL of the 12% heat denatured collagen solution (at about 37° to about 50° C.) was added to the sponge, and spread and blended with the sponge by using a spatula. After 10 minutes, the mixture became a putty like material that was cohesive and malleable, held its shape and did not wash away (disintegrate) after soaking in water.

The putty may be employed in any clinical or surgical applications where bone void filler, demineralized bone matrix and bone growth factors have been employed, particularly to repair or reconstruct muscular skeleton in a non-weight bearing site. For example, the product can be extruded from a syringe directly onto a defect site or molded into different contour or shape to fit into a surgical site.

Example 5

Exemplary Putty Composition Preparation

In this example, a gelatin carrier was included in a fibrillar collagen DMB sponge. The sponge was prepared by whipping 0.125 gram of collagen, 0.005 gram of gelatin, 5.4 mL 20 mM hydrochloric acid, 0.156 gram calcium phosphate dibasic (Dical), and 1.25 gram DMB particles into a slurry, followed by lyophilization of the slurry into a 1.2 cm by 15 cm sponge. After rehydration of the sponge with water (neutral pH, e.g., pH 7.0), the sponge became flexible and formed into a putty like material. This putty could be molded into different shapes and held its shape in water.

The putty may be employed in any clinical or surgical applications where bone void filler, demineralized bone matrix and bone growth factors have been employed, particularly to repair or reconstruct muscular skeleton in a non-weight bearing site. For example, the product can be extruded from a syringe directly onto a defect site or molded into different contour or shape to fit into a surgical site.

Example 6

Exemplary Implant Shapes

Figure 14A:
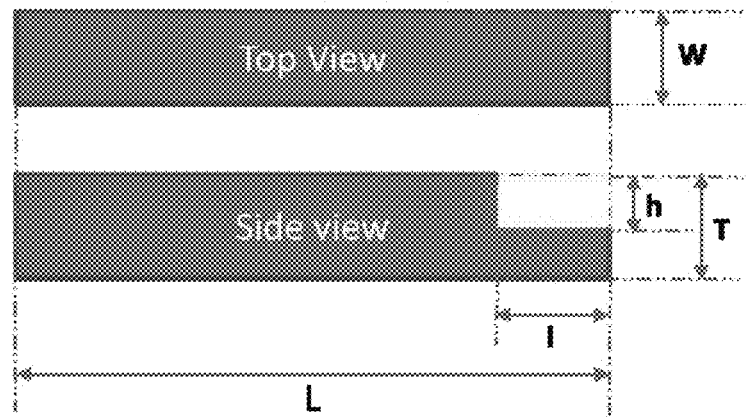
FIG. 14 illustrates exemplary shapes and dimensions of three-dimensional implants formed with bone void filler compositions of the invention. A) Implants with lips. B) Implants with concave receptacles. C) Capsule, bullet and sheet-shaped implants.
Figure 14B:
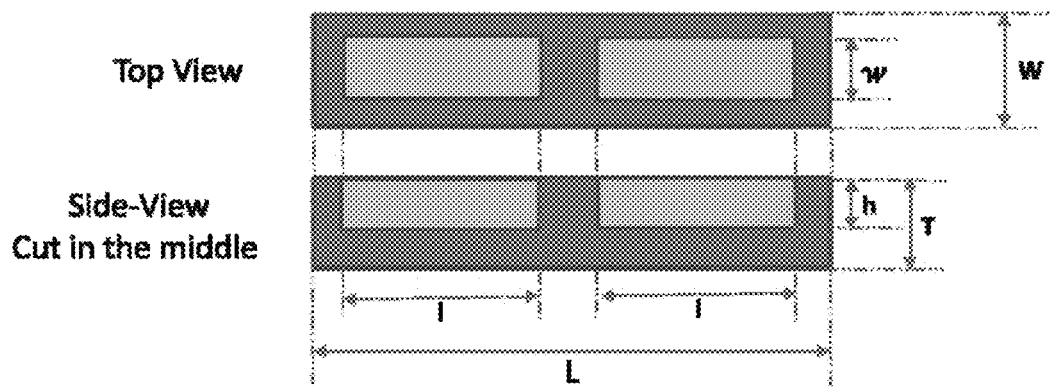
Figure 14C:
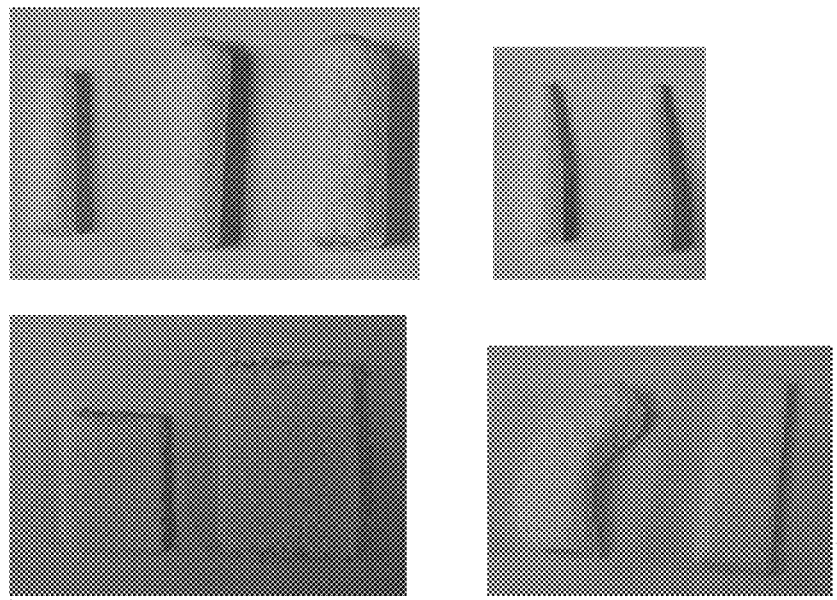

In one embodiment, a sponge may be employed for spine defects or injuries, e.g., in a bar with dimensions at about 1 mm (W)×about 2 mm (L)×about 4 to about 5 mm (T), about 10 mm (W)×about 50 mm (L)×about 4 mm to about 5 mm (T) or about 2 mm (W)×about 100 mm (L)×about 4 mm to about 5 mm (T). Other dimensions for a bar include about 10 mm (W)×about 20 mm (L)×about 5 mm (T), about 20 mm (W)×about 50 mm (L)×about 5 mm (T), or about 20 mm (W)×about 100 mm (L)×about 5 mm (T). In one embodiment, the sponge may be employed as a strip for a defect such as in scoliosis, with dimensions of about 12 mm (W)×about 10 mm (L)×about 8 mm to about 10 mm (T), and a lip of about 15 mm (l)×about 5 mm to about 6 mm (h), or about 12 mm (W)×about 20 mm (L)×about 8 mm to about 10 mm (T), with a lip of about 15 mm (l)×about 5 mm to about 6 mm (h) (FIG. 14A). Other dimensions for a strip include about 12 mm (W)×about 100 mm (L)×about 10 mm (T), and a lip of about 15 mm (l)×about 5 mm to about 6 mm (h), or about 12 mm (W)×about 200 mm (L)×about 10 mm (T), with a lip of about 15 mm×about 5 mm to about 6 mm (h). In one embodiment, the sponge may be employed as a vessel, with dimensions of about 25 mm (W)×about 50 mm (L)×about 10 mm (T), where the concavity in the vessel is about 40 mm (l)×about 15 mm (w)×about 5 mm to about 7 mm (h) or with two concavities where the vessel has dimensions of about 25 mm (W)×about 100 mm (L)×about 10 mm (T), and each concavity has dimensions of about 40 mm (l)×about 15 mm (w)×about 5 mm to about 7 mm (h) (FIG. 14B). Other dimensions for a vessel include about 25 mm (W)×about 50 mm (L)×about 10 mm (T), with a concavity of about 15 mm (w)×about 20 mm (l)×about 5 mm (h), or about 25 mm (W)×about 100 mm (L)×about 10 mm (T), with a concavity of about 15 mm (w)×about 40 mm (l)×about 5 mm (h). Exemplary dimensions for a bullet shape include about 5.5 mm (dia)×about 15 mm (h), about 7 mm (dia)×about 20 mm (h), or about 9 mm (dia)×about 23 mm (h). Exemplary dimensions for a lower ridge include about 6 mm (w)×about 32 mm (l)×about 12 mm (h) and R about 3 mm, and for an upper ridge include about 10 mm (w)×about 30 mm (h)×about 10 mm (h), and R about 0.8 mm, about 1.8 mm, or about 2.8 mm. The sizes of other shapes, e.g., those for introduction into acetabular or intermedullary regions, can be determined by one of skill in the art.

Figure 15:
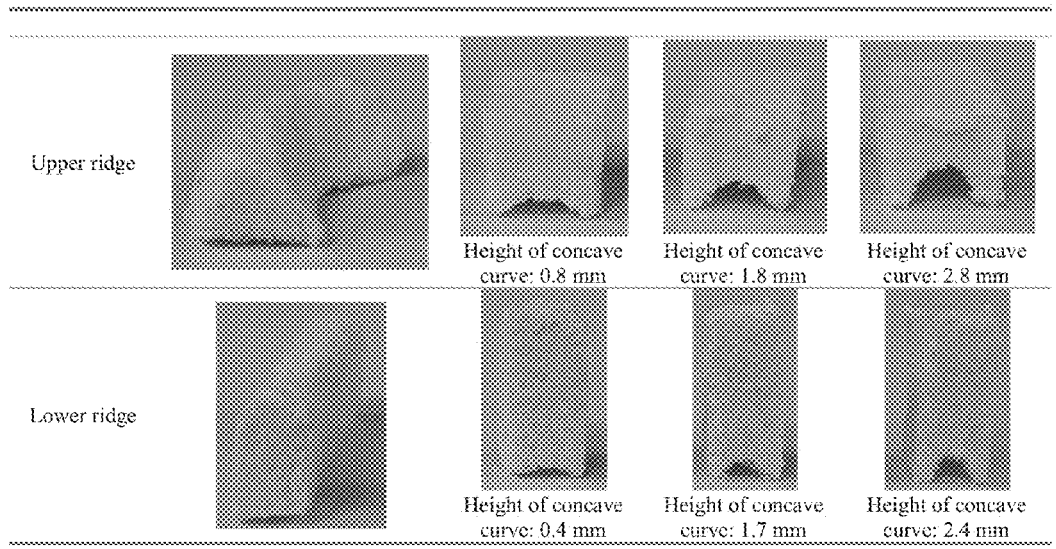
FIG. 15 illustrates shapes with concave curves (e.g., for use in upper and lower dental ridge augmentation).

In one embodiment, the sponge may be employed in dental applications. Exemplary shapes and dimensions for dental implants are provided in Tables 2-6 (see also FIG. 15).

TABLE 2

| Shape of sponge | Dimensions Diameter (mm) × Height (mm) |
| --- | --- |
| Capsule | 7 × 25 |
| Capsule | 11 × 30 |
| Capsule | 15 × 30 |

TABLE 3

| Shape of sponge | Dimensions of sponge Diameter (mm) × Height (mm) |
| --- | --- |
| Bullet | 7 × 25 |
| Bullet | 9 × 25 |

TABLE 4

| Shape of sponge | Dimensions Length (mm) × Width (mm) × Height (mm) |
| --- | --- |
| Sheet | 15 × 20 × 3-4 |
| Sheet | 20 × 30 × 3-4 |

TABLE 5

| Type of sponge | Dimensions Length (mm) × Diameter (mm) × Height (mm) |
| --- | --- |
| Upper ridge | 30 × 10 × 10 |
| Lower ridge | 32 × 6 × 12 |

TABLE 6

|  | Small | Medium | Large |
| --- | --- | --- | --- |
| Upper ridge | Height of concave curve: 0.8 mm | Height of concave curve: 1.8 mm | Height of concave curve: 2.8 mm |
| Lower ridge | Height of concave curve: 0.4 mm | Height of concave curve: 1.7 mm | Height of concave curve: 2.4 mm |

Example 7

Bone Forming Activity of Implant with Calcium Acetate as a Mineral Component Various test samples (Table 7), as described below, were implanted subcutaneously in athymic rats to evaluate the compositions with respect to their efficacy for bone growth. Male athymic rats, about seven weeks old at the commencement of the study, were used. Surgery on each rat was performed as follows. Prior to the surgery, the rats were anesthetized by intraperitoneal injection of ketamine/Xylazine solution; 70 mg/kg of ketamine and 5 mg/kg of xylazine. General anesthesia was noted by a lack of response to a toe pinch. Anesthesia was maintained with isoflurane, if needed.

The ventral and dorsal thoracic area of each rat was swabbed with chlorhexadine and alcohol scrub. Using a scalpel or scissors, a 1 cm incision was made in the skin on the right side. This ventral incision was made at the base of the rib cage. After incision, a pocket was prepared beneath the skin and above the incision by blunt dissection towards the axilla. A large blood vessel (cranial thoracodorsal vein) was noted which was often adhered to the skin/subcutaneous tissues. The right ventral implant was placed in the pocket of the subcutaneous tissue approximately 5 mm anterior to the incisions on the chest wall directly below the cranial thoracodorsal blood vessel. When the right ventral side was implanted, the left side had the same procedure done for implantation. The rat was then re-positioned to make two more small (1 cm) incisions in the skin of the dorsal thorax. The two dorsal implants were placed toward the middle of the rib cage. All wound closure was accomplished using either stainless steel wound clips or sutures. Thus, each rat had four subcutaneous implants with bilateral placements of the test articles in each of the ventral and dorsal thoracic regions. FIG. 3 is a representative image of a rat ventral and dorsal views depicting subcutaneous implant sites Q1-Q4.

Three different types of systems were evaluated: implants containing collagen and DMB, implants containing collagen, DMB, and BMP-2, and implants containing collagen, DMB, and varying amounts and combinations of salts (i.e., calcium acetate, DiCal, trisodium phosphate, or hydroxyapatite). Nominal total salt concentrations evaluated were 10 and 19 weight percent relative to the combined weight of total salt components and the total weight of collagen, accounting for collagen contained in the carrier as well as any collagen found in other components, including the demineralized bone, which was assumed for purposes of experimentation to be 90% by weight collagen. DMB particles were provided by AlloSource, Inc.

TABLE 7

| Group No | Implant Material |
| --- | --- |
| A | Collagen + DMB |
| B | Collagen + DMB + BMP-2 (1.0 µg) |
| C | Collagen + DMB + CaAc 10% |
| D | Collagen + DMB + CaAc 19% |
| E | Collagen + DMB + $Na_3PO_4$ + CaAc 10% |
| F | Collagen + DMB + DiCal + CaAc 10% |
| G | Collagen + DMB + DiCal + CaAc 19% |
| H | Collagen + DMB + HA 19% |
| I | Collagen + DMB + DiCal 10% |
| J | Collagen + DMB + DiCal 19% |

Implants with different compositions (Table 8) were generally prepared as follows. Hydrochloric acid (30 mM) was added to the collagen to wet the collagen. The combination was then whipped with a lab scale mixer to obtain a composition with a gel-like consistency. The appropriate amount of DMB powder was added and mixed thoroughly with a spatula to obtain a putty-like consistency. Discs of a desired shape residing on a glass plate were filled with the putty. A second glass plate was positioned over the discs and clamped into place. The glass plate assembly was frozen, generally for a minimum of one hour at −80° C. The discs were removed from the freezer and excess material was trimmed from the disc molds. The glass plate assembly was quickly returned to the freezer again for a minimum of one hour at −80° C. The assembly was then subjected to lyophilization for a minimum of 12 hours. The resulting sponge implants were then recovered from the molds.

For implants intended to contain various amount of salts or combinations of different salts, the appropriate amount of salt was added to the combination of hydrochloric acid and collagen prior to the whipping step. The combination of collagen, hydrochloric acid, and DiCal was first mixed with a spatula and then whipped with a mixer.

For implants intended to contain BMP-2, 20 µL of reconstituted BMP-2 (0.25 µg/µL in 4 mM HCl) was added to one side of the lyophilized sponge implant disc followed by adding another 20 µL of the reconstituted BMP-2 to the other side of the lyophilized sponge implant discs. The BMP-2 solution was allowed to soak into the sponge implant disc. The sponge implant disc was subjected to freezing conditions for one hour at −80° C. The assembly was then subjected to lyophilization for a minimum of 12 hours. The resulting sponge implants were then recovered.

After 28 days, the implants were removed for radiographic evaluation. The explants were fixed in 10% NBF and radiographed. The representative radiographs from each treatment group are depicted in FIG. 16. The radiograph showed that the presence of DiCal, calcium acetate, or calcium acetate combined with Dical or trisodium phosphate enhanced bone formation at the concentrations evaluated.

Example 8

Fusion Activity Following Defect Filling

A critical size defect (5 mm) in the left femur of a rat was filled with one of four compositions (see Table 9) in the form of a cylinder about 6 mm in length and about 3 mm in diameter; 1) a bone void filler composition of the invention; 2) a composition formed with collagen and BMP-2; 3) a composition formed with collagen and DBM; or 4) Puros® DBM. Radiographs of the filled defect were taken at 4 to 8 weeks post-filling, and micro CT scans were taken at 8 weeks post-filling.

Figure 17:
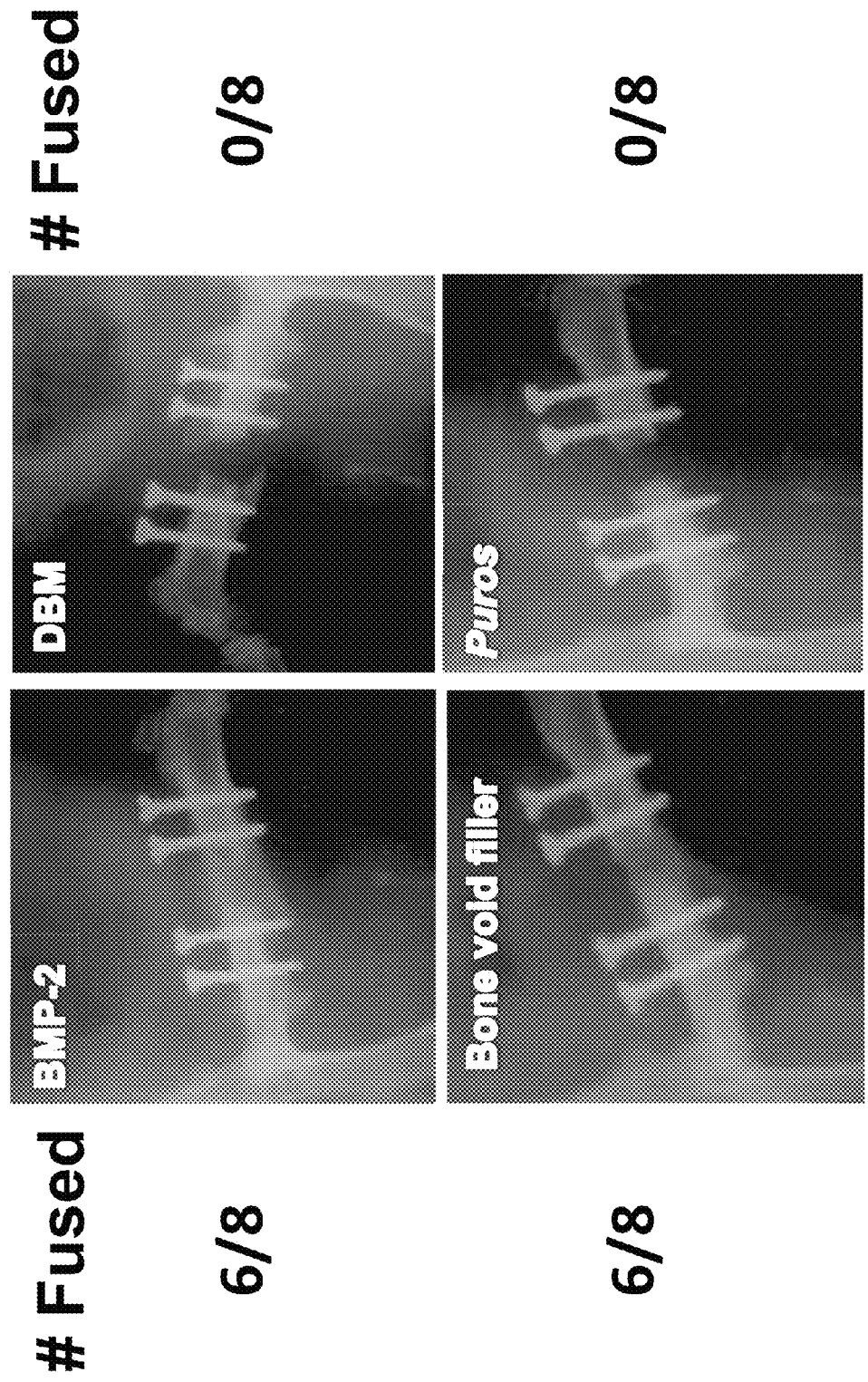
FIG. 17 shows radiographs of rat left femur defects 4 weeks after filling with various compositions.

The radiographs taken at 4 weeks are shown in FIG. 17. Collagen plus DMB and Puros® DBM did not induce fusion at any of 8 defects while a bone void filler composition of the invention and a composition formed with collagen and BMP-2 resulted in fusion of 6/8 defects. Collagen and BMP-2 may have shown better fusion than a bone void filler composition of the invention at 8 weeks.

TABLE 8

| Groups | Carrier (g) | DMB (g) | Mineral (g) | HCl (mL) | BMP-2 (µg) |
| --- | --- | --- | --- | --- | --- |
| Collagen + DMB | 0.125 | 1.25 | N/A | 5.4 | N/A |
| Collagen + DMB + BMP-2 | 0.125 | 1.25 | N/A | 5.4 | 1 |
| Collagen + DMB + CaAc 10% | 0.125 | 1.25 | CaAc 0.156 g | 5.4 | N/A |
| Collagen + DMB + CaAc 19% | 0.125 | 1.25 | CaAc 0.3125 g | 5.4 | N/A |
| Collagen + DMB + $Na_3PO_4$ + CaAc 10% | 0.125 | 1.25 | $Na_3PO_4$ 0.096 g; CaAc 0.06 g | 5.4 | N/A |
| Collagen + DMB + DiCal + CaAc 10% | 0.125 | 1.25 | CaAc 0.068 g; Dical: 0.088 g | 5.4 | N/A |
| Collagen + DMB + DiCal + CaAc 19% | 0.125 | 1.25 | CaAc 0.136 g; Dical: 0.176 g | 5.4 | N/A |
| Collagen + DMB + HA 19% | 0.125 | 1.25 | HA 0.3125 g | 5.4 | N/A |
| Collagen + DMB + DiCal 10% | 0.125 | 1.25 | Dical 0.156 g | 5.4 | N/A |
| Collagen + DMB + DiCal 19% | 0.125 | 1.25 | Dical 0.3125 g | 5.4 | N/A |

TABLE 9

| Group | Carrier (g) | DBM (g) | Mineral (g) | HCl (mL) | BMP-2 (µg) |
|---|---|---|---|---|---|
| Collagen + DBM + Mineral | 0.223 | 2.013 | 0.265 | 9.2 | N/A |
| Collagen + BMP-2 | 1.000 | N/A | N/A | 41.2 | 10 |
| Collagen + DBM | 0.250 | 2.250 | N/A | 10.3 | N/A |
| Puros ® DBM Putty | N/A | N/A | N/A | N/A | N/A |
| Empty defect | N/A | N/A | N/A | N/A | N/A |

Example 9

Biocompatible Fibers for Use in a Bone Void Filler Composition

To create or increase load bearing capabilities, and thus the structural integrity, in a material that is introduced around or into a void or fracture, which material is absorbed over time and is replaced by good quality bone, a biocompatible and biodegradable fiber is added to a bone void filler composition of the invention. The weight percentage of the fibers can vary based upon the desired properties, e.g., strength, biologic properties, handling characteristics. In one embodiment, the weight percentage of fiber may be from about 10% to about 70%. Typically, as the fiber length decreases, the percentage of fill decreases in order to achieve the desired strength.

For example, bioactive glass (a.k.a. Bioglass) fibers are incorporated into a bone void filler composition. The bioactive glass fibers act as fiber reinforcement and increase the mechanical properties of the material and/or provide for more robust handling properties. One example of a biocompatible fiber is 45S5, which is composed of calcium salts, phosphorous, sodium salts and silicates (45S5 is 46.1 $SiO_2$, 26.9 CaO, 24.4 $Na_2O$ and 2.5 $P_2O_5$ (mol %)) which are essential elements of mineralized bone. Other bioglass compositions include, but are not limited to, 58S which is 60 $SiO_2$, 36 CaO and 4 $P_2O_5$ (mol %), S70C30 which is 70 $SiO_2$ and 30 CaO (mol %), and 13-93 which is 6.0 $Na_2O$, 7.9 $K_2O$, 7.7 MgO, 22.1 CaO, 1.7 $P_2O_5$, 54.6 $SiO_2$ (mol. %). Yet other biocompatible fibers include SSSE which is 54.1 $SiO_2$, 22.3 CaO, 19.8 $Na_2O$, 1.3 $P_2O_5$ and 8.7 CaF (mol %) and SS3P4 which is 54.2 $SiO_2$, 22 CaO, 22.9$Na_2O$ and 0.9 $P_2O_5$ (mol %)

Various compositions that incorporate bioactive glass have been shown to bond with bone and promote bone regeneration while it is resorbed by the body. The breakdown of the bioactive glass provides essential mineral elements to an area but does not create an undesirable localized pH which would retard the bone formation/healing process. In another embodiment, the bioactive glass may be fabricated as a mat, e.g., one that is cut to a desired shape, then a bone void filler composition is added to the mat, e.g., pressed into it.

Example 10

Bone Forming Activity of Demineralized Bone Putty Implants

Various test samples (Table 10), as described below, were implanted subcutaneously in athymic rats to evaluate the compositions with respect to their efficacy for bone growth. Male athymic rats, about seven weeks old at the commencement of the study, were used. Surgery on each rat was performed as follows. Prior to the surgery, the rats were anesthetized by intraperitoneal injection of ketamine/Xylazine solution; 70 mg/kg of ketamine and 5 mg/kg of xylazine. General anesthesia was noted by a lack of response to a toe pinch. Anesthesia was maintained with isoflurane, if needed.

The ventral and dorsal thoracic area of each rat was swabbed with chlorhexidine and alcohol scrub. Using a scalpel or scissors, a 1 cm incision was made in the skin on the right side. This ventral incision was made at the base of the rib cage. After incision, a pocket was prepared beneath the skin and above the incision by blunt dissection towards the axilla. A large blood vessel (cranial thoracodorsal vein) was noted which was often adhered to the skin/subcutaneous tissues. The right ventral implant was placed in the pocket of the subcutaneous tissue approximately 5 mm anterior to the incisions on the chest wall directly below the cranial thoracodorsal blood vessel. When the right ventral side was implanted, the left side had the same procedure done for implantation. The rat was then re-positioned to make two more small (1 cm) incisions in the skin of the dorsal thorax. The two dorsal implants were placed toward the middle of the rib cage. All wound closure was accomplished using either stainless steel wound clips or sutures. Thus, each rat had four subcutaneous implants with bilateral placements of the test articles in each of the ventral and dorsal thoracic regions. FIG. 3 is a representative image of a rat ventral and dorsal views depicting subcutaneous implant sites Q1-Q4.

Three different types of systems were evaluated: 1) implants containing fibrillar collagen and DMB; 2) implants containing fibrillar collagen and BMP-2; 3) implants containing fibrillar collagen, gelatinized collagen, DMB, with or without calcium hydrogen phosphate (DiCal) (see Table 10). DMB particles were provided by AlloSource, Inc.

Implants were prepared as follows. To prepare sponge implants, the procedure is as follows. Hydrochloric acid (30 mM) was added to the collagen to wet the collagen. The combination was then whipped with a lab scale mixer to obtain a composition with a gel-like consistency. The appropriate amount of DMB powder was added and mixed thoroughly with a spatula to obtain a putty-like consistency. Discs of a desired shape residing on a glass plate were filled with the putty. A second glass plate was positioned over the discs and clamped into place. The glass plate assembly was frozen, generally for a minimum of one hour at −80° C. The discs were removed from the freezer and excess material was trimmed from the disc molds. The glass plate assembly was quickly returned to the freezer again for a minimum of one hour at −80° C. The assembly was then subjected to lyophilization for a minimum of 12 hours. The resulting sponge implants were then recovered from the molds. To prepare putty implants, the procedure is as follows. The prepared DMB containing sponges (as previously described) were hydrated with 20 mL deionized water and hydrated for 10 min. After hydration, the excess water was removed by squeezing the water out. Then 0.6 mL gelatinized collagen (per gram of dry weight sponge material), which were prepared by heating 12% collagen in saline solution at 121° C. for 1 hr, was added to the hydrated sponge and thoroughly mixed with the hydrated sponge. After 1-2 min mixing, the materials became a putty. About 0.1 gram of this material was weighed and implanted into rats.

For implants intended to contain various amount of salts or combinations of different salts, the appropriate amount of salt was added to the combination of hydrochloric acid and collagen prior to the whipping step. The combination of collagen, hydrochloric acid, and DiCal was first mixed with a spatula and then whipped with a mixer.

For implants intended to contain BMP-2, 20 µl of reconstituted BMP-2 (0.25 µg/µL) was added to one side of the lyophilized sponge implant disc followed by adding another 20 µL of the reconstituted BMP-2 to the other side of the lyophilized sponge implant discs. The BMP-2 solution was allowed to soak into the sponge implant disc. The sponge implant disc was subjected to freezing conditions for one hour at −80° C. The assembly was then subjected to lyophilization for a minimum of 12 hours. The resulting sponge implants were then recovered.

Figure 18:
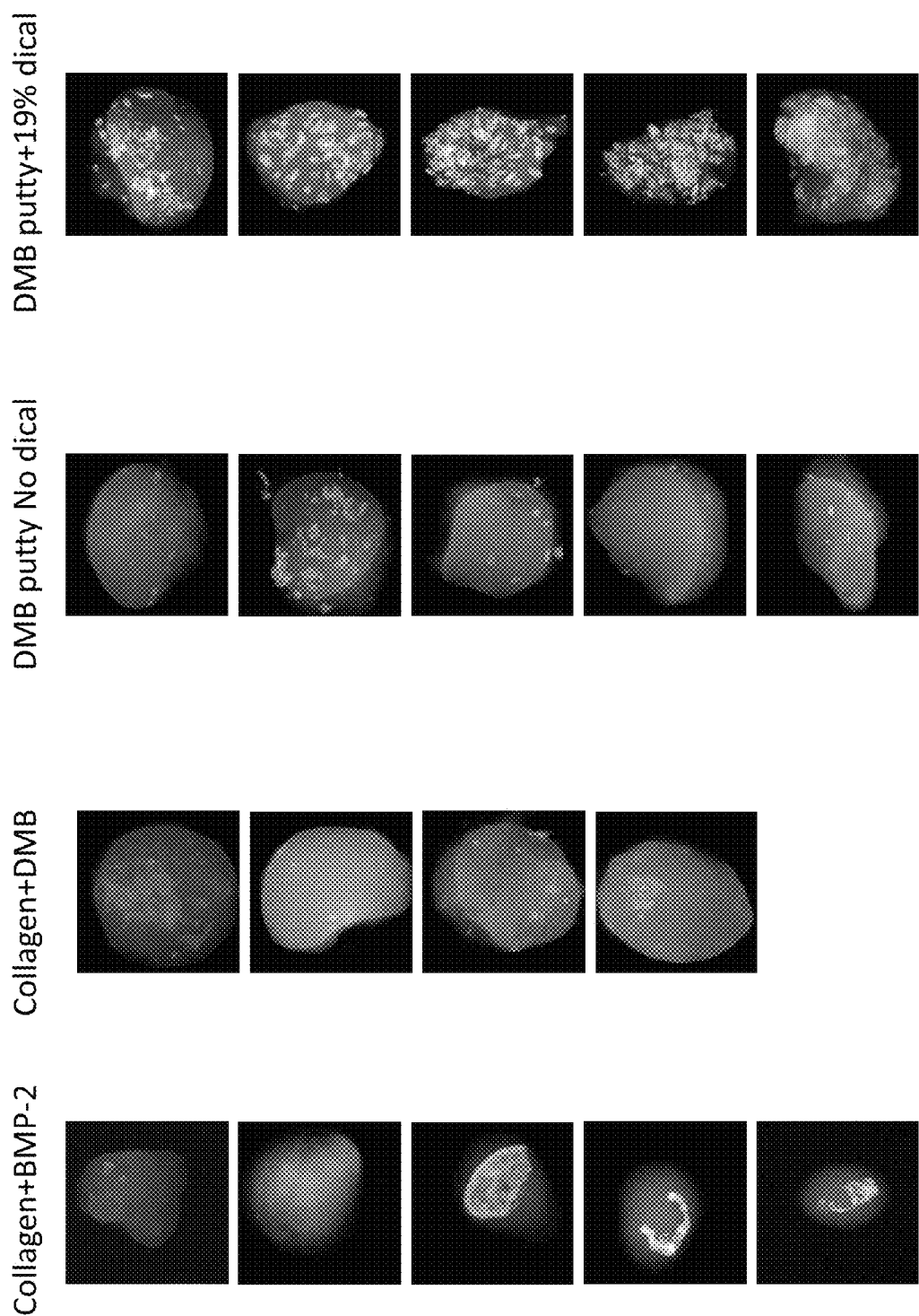
FIG. 18 shows radiographs of sponge or putty implants of varying composition obtained at 4 weeks post subcutaneous implantation in athymic rats.

After 28 days, the implants were removed for radiographic evaluation. The explants were fixed in 10% NBF and radiographed. The radiographs from each treatment group are depicted in FIG. 18. The radiograph showed DBM putty with DiCal (formulated with fibrillar collagen and gelatinized collagen) enhanced bone formation compared to DBM putty without DiCal and DMB particles with collagen only.

TABLE 10

| Groups | Fibrillar Collagen (g) | DMB (g) | Mineral (g) | HCl (mL) | BMP-2 (µg) | Gelatinized collagen (g) | 0.9% saline (mL) |
|---|---|---|---|---|---|---|---|
| Fibrillar Collagen + DMB (sponge) | 0.125 | 1.25 | N/A | 5.4 | N/A | N/A | N/A |
| Fibrillar Collagen + BMP-2 (sponge) | 0.125 | 1.25 | N/A | 5.4 | 1 | N/A | N/A |
| Fibrillar Collagen + DMB + heat gelatinized collagen (putty) | 0.125 | 1.25 | Dical 0.156 g | 5.4 | N/A | 0.101 | 0.8 |
| Fibrillar Collagen + DMB + heat gelatinized collagen + Dical 19% (putty) | 0.125 | 1.25 | Dical 0.156 g | 5.4 | N/A | 0.134 | 1.2 |

Example 11

Effect of Varying Amounts of Calcium Phosphate on Posterio-Lateral Spine Fusion

Materials and Methods

Treatment Groups.

Animals (males) were randomized into treatment groups, based on body weights collected following arrival (Table 11). The mean bodyweights for each group were reviewed to ensure that the group mean and standard deviation values satisfy the assumption of homogeneity. Group allocations were documented in the study records. Each animal received an implant from the same group on both the left side and the right side.

TABLE 11

| Group | Surgery | Treatment | Dose | # Animals |
|---|---|---|---|---|
| 1 | Bilateral lumbar implant | DBM | n.a. | 4 |
| 2 | Bilateral lumbar implant | DBM 1 + BMP-2 | 2 µg/rat | 3 |
| 3 | Bilateral lumbar implant | DBM 1 + Calcium phosphate mineral 0.5% | n.a. | 4 |
| 4** | Bilateral lumbar implant | DBM 2 (Puros ® DBM Putty) | 0.5 g/side | 4 |
| 5 | Bilateral lumbar implant | DBM 1 + Calcium phosphate mineral 2.5% | n.a. | 4 |
| 6 | Bilateral lumbar implant | DBM 1 + Calcium phosphate mineral 5.0% | n.a. | 4 |
| 7 | Bilateral lumbar implant | Collagen + BMP-2 | 5 µg/rat | 3 |
| 8 | Negative control | Decortication only on left side | n.a. | 2 |

**Animals from Group 4 were euthanized 4 weeks after surgery. Additionally, Animal 153 (Group 3) was found to be moribund and also euthanized at 4 weeks. All other animals were euthanized 8 weeks after surgery. These animals received oxytetracycline and calcein labels.

Surgery.

Anesthesia was induced and maintained according to routine methods. General anesthesia was noted by a lack of response to a toe pinch. Anesthesia was maintained with isoflurane, as necessary. After induction of anesthesia, the rat was placed in ventral recumbency with front and hind legs extended. Using standard laboratory techniques, the spinal region area was clipped or shaved, cleaned and scrubbed as per proper aseptic surgical technique.

L4-L5 posteriolateral fusions were performed, as follows. The spine was approached through a single midline skin incision and two separate muscle incisions, one to the left and one to the right side of the vertebral column, were made to approach the spine. The level was identified during surgery by referencing from the pelvis. Once exposed, the transverse processes of L4 and L5 on both sides were decorticated. Implant material was then placed in the posteriolateral gutters as described.

The fascia was closed with sutures. The skin was closed with sutures or staples. Any staples or sutures remaining 14 days post-op were removed under isoflurane anesthesia.

Implant Material Placement.

Back muscles attached to the transverse processes are lifted and the implant was placed below the muscle spanning L4 and L5 transverse processes, to secure the implant in place.

Oxytetracycline and Calcein Labels.

One dose of oxytetracycline (30 mg/kg body weight; Sigma 05875) was given to each animal 6 days prior to sacrifice and one dose of calcein (10 mg/kg) was given to each animal 2 days prior to sacrifice.

Mechanical Stability Testing.

Mechanical stability was assessed on all samples immediately following tissue collection by manual palpation. Two individuals blinded to the group assignment for treatment assessed the stability of each animal using the scoring system below, as described by Qui et al. (*J. Biomed. Mat. Res.*, 82B:239 (2007)):

Manual Palpation Score

0—empty
1—some bumps
2—some gaps
3—small gaps
4—completely bridged

Histology.

Figure 19:
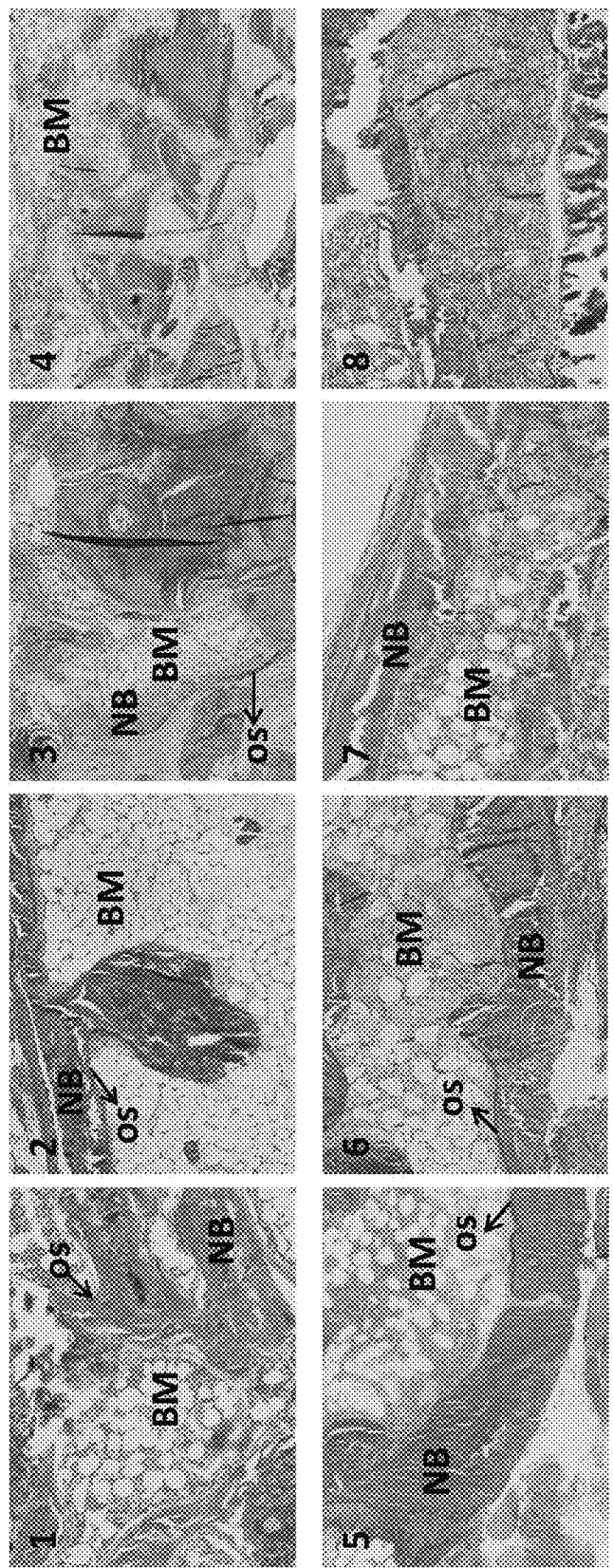
FIG. 19 shows representative histology from samples from eight different groups (group number in upper left corner) at 8 weeks post defect filling stained with Mason's trichrome. BM=bone marrow; NB=new bone; OS=osteiod (newly mineralizing zone).
Figure 20:
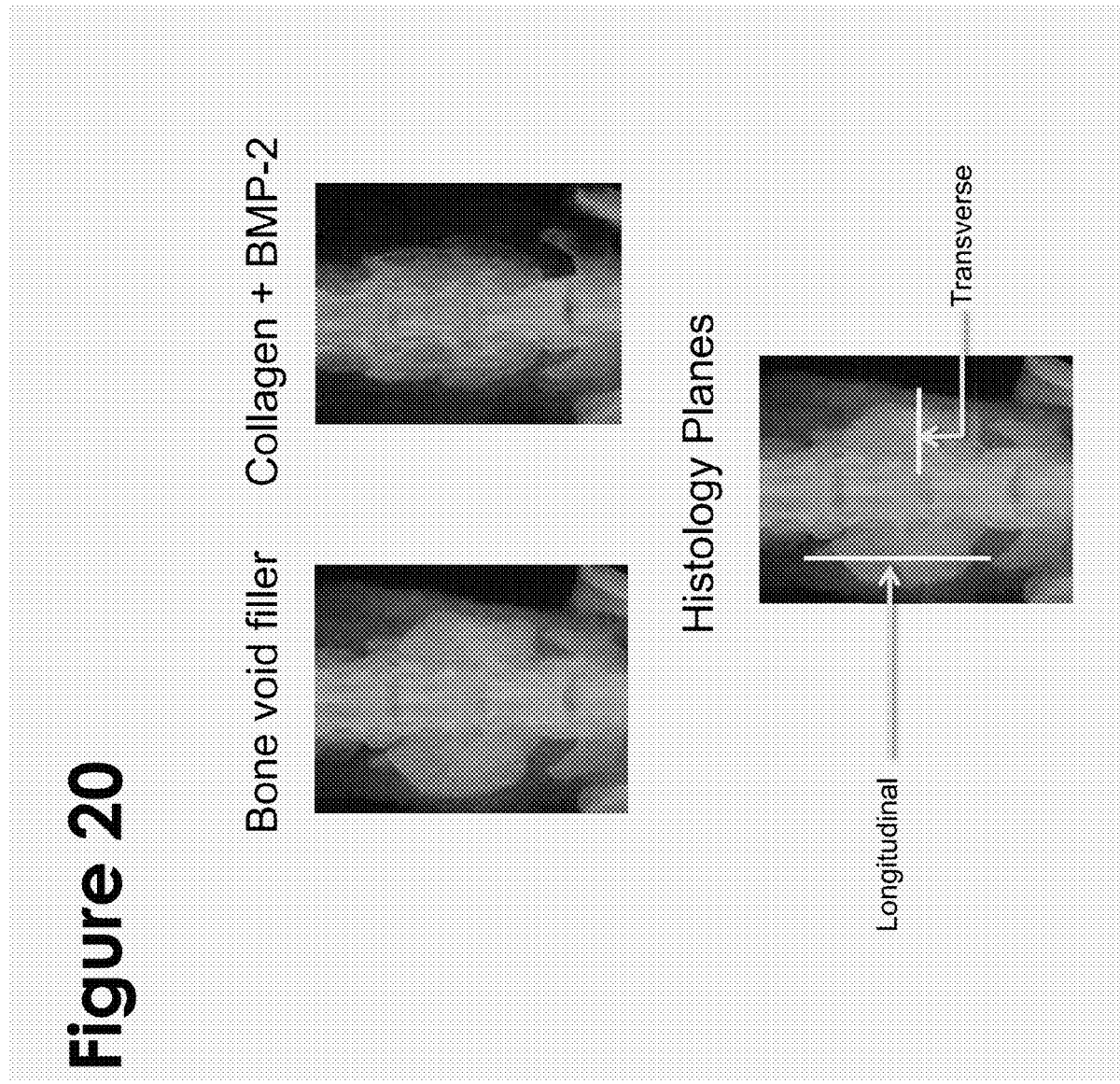
FIG. 20 illustrates radiographs from rats 8 weeks after posterior-lateral spine fusions that employed a bone void filler composition of the invention or a composition having collagen and BMP-2.
Figure 21:
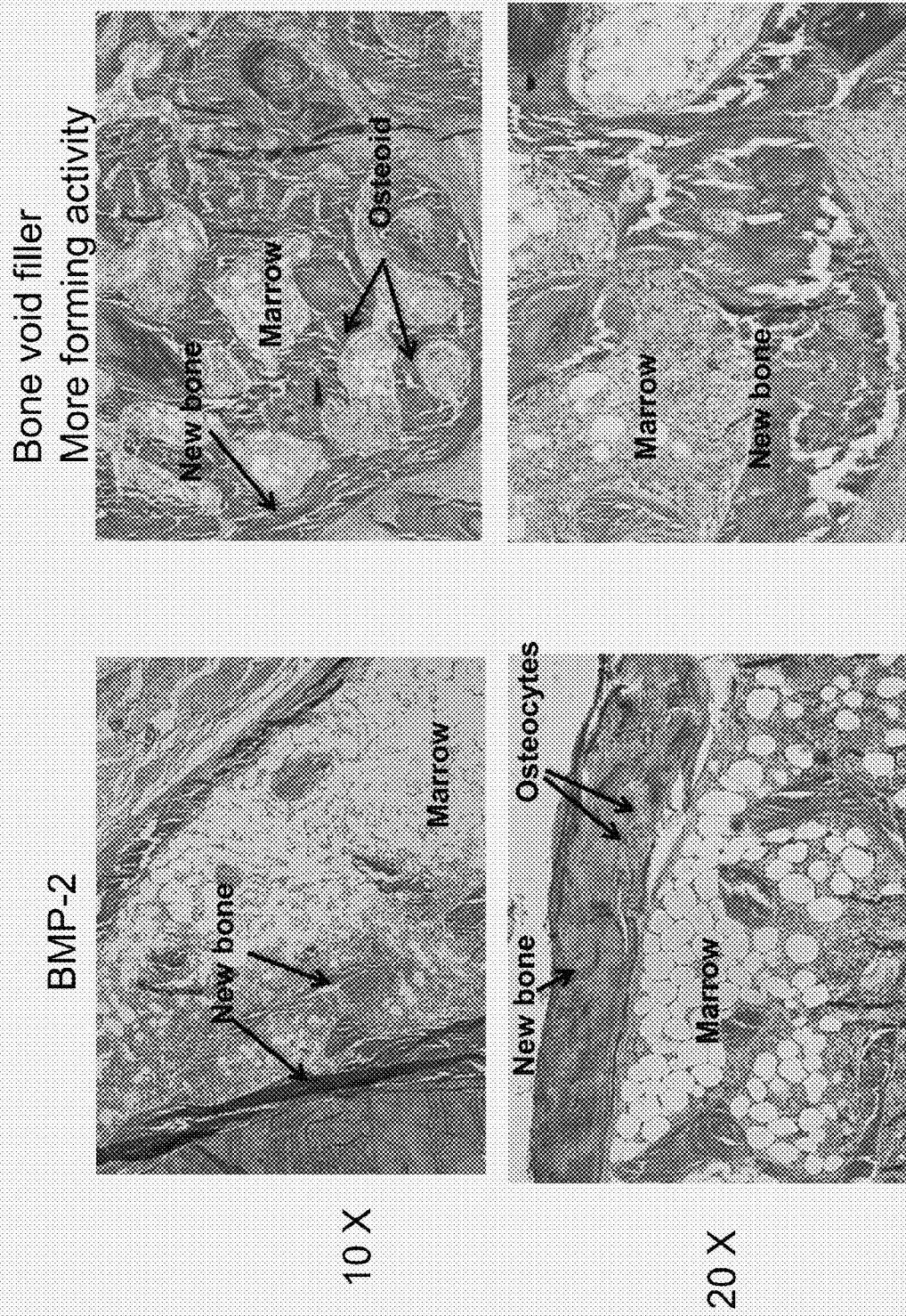
FIG. 21 illustrates sections from rats 8 weeks after posterior-lateral spine fusions that employed a bone void filler composition of the invention or a composition having collagen and BMP-2.
Figure 23:
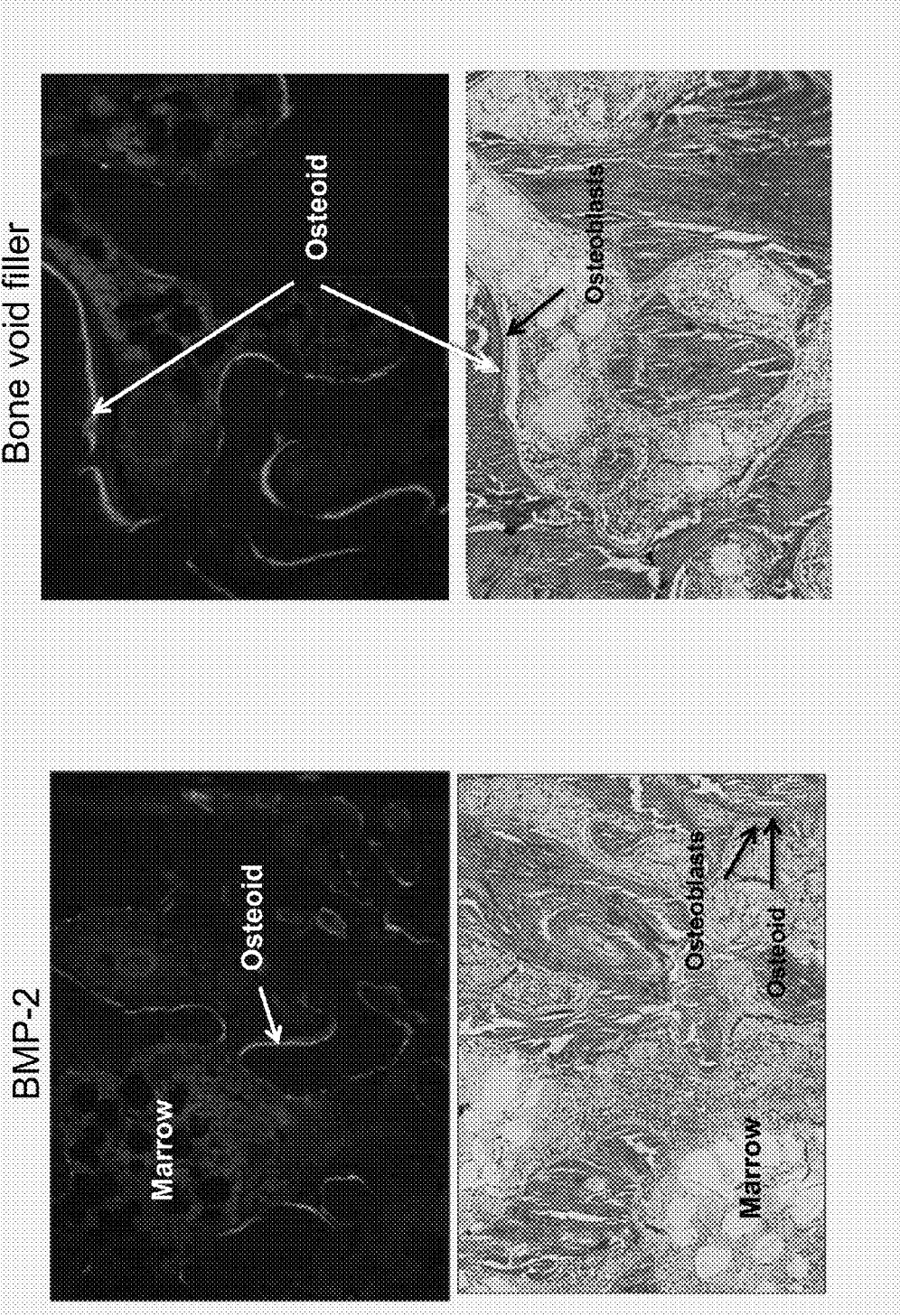
FIG. 23 illustrates serial sections from rats 8 weeks after posterior-lateral spine fusions that employed a bone void filler composition of the invention or a composition having collagen and BMP-2. Serial sections that were about 40 microns apart were stained with a fluorochrome or Trichrome.

Spine segments harvested from the study were processed for undecalcified bone histology. Two sections from each block were prepared; one from the transverse or cross-sectional plane and the other from the sagittal plane along the spine column that include the fusion mass on each side of the spinal column. The sections were stained with Masson's trichrome (see FIGS. 19, 21 and 23). Additionally, one slide from each plane was left unstained for fluorochrome microscopy (see FIGS. 22-23).

TABLE 12

Scoring criteria

| Parameter | Score | Definition |
| --- | --- | --- |
| Fibrosis | −1 to −4 | Amount of fibrotic tissue present in the marrow and/or surrounding the implanted pieces (−4 is extensive fibrosis). |
| Inflammation | −1 to −4 | Severity of inflammatory cells accumulation and infiltration in and around the implanted area (−4 is extensive inflammation). |
| New bone segments | 1 to 4 | Indicates the presence of a bony area that does not come from the Periosteal bony proliferation of the implant or existing bone |
| New bone on implant surfaces | 1 to 4 | Indicates the presence of new lamellar bone added to the cancellous bone surfaces within the implant pieces |
| New cartilage | 1 to 4 | Indicates the presence of new cartilage in and around the implant pieces, besides the remnant growth plates in some of the implant pieces |
| Fusion of implants and existing bone | 1 to 4 | Indicates the extent of surface contact by the callus formed between the implant pieces and existing bone |
| Fusion of implants | 1 to 4 | Indicates the extent of surface contact by the callus formed between the implant pieces |
| Amount of new bone labeled | 1 to 4 | Indicated the extent of surface showing fluorochrome labels in the fusion area |

Results

A total of 26 male athymic rats (Hsd:RH-Foxn1$^{rnu}$), 3 months old upon arrival, except those in the negative control group (2 animals), had bilateral surgeries implanted with a test article in the right and left posterior-lateral gutters between L4 and L5. The negative control group did not receive any implant on the decorticated side.

Following implantation, rats were observed for clinical signs of complications for 3 days. Body weights were determined at the start of the study and weekly thereafter. Four weeks post-surgery, animals from Group 4 Puros® DBM Putty were sacrificed and the lumbar segment containing the fusion masses removed. Eight weeks post-surgery, all rats, with the exception of 4 animals from Group 4, were sacrificed and the lumbar segment containing the fusion masses removed. Before each sacrifice, all animals were given one dose of oxytetracycline (30 mg/kg body weight) 6 days prior to sacrifice and one dose of calcein 2 days prior to sacrifice.

Mechanical stability was assessed by manual palpation on all samples. The spine samples (T13-S1 region) were placed in 10% neutral buffered formalin and radiographed. The radiographs were scored. Complete fusion was deemed present if bridging bone was noted completely in inter-transverse region. Preserved samples were subjected to micro-CT analysis.

The radiographic results indicated good spinal fusion with DBM 1, DBM 1+2.5% or 5% calcium phosphate mix, DBM 1+BMP-2, and collagen+BMP-2, however, the density of the fusion mass in collagen+BMP-2 was significantly less than that of DBM 1. DBM 1+0.5% calcium phosphate mineral mix and DBM 2 (Puros® DBM Putty) showed significantly less complete fusion and density when compared to DBM 1. There was no fusion mass noted in any animal in the negative control group.

Results for mechanical stability of the fusion area were compared to DBM 1 treated group (Group 1). There were significant reductions of mechanical stability score in animals treated with DBM 1+0.5% calcium phosphate mineral and collagen+BMP-2, when compared to DBM 1-treated animals (Table 13). There was a positive trend of enhanced mechanical stability with increasing calcium phosphate mineral amounts.

TABLE 13

Mechanical Stability

| Treatment Group | Data | Tester A | Tester B |
| --- | --- | --- | --- |
| Group 1 | Mean | 4.00 | 4.00 |
| DBM 1 | SD | 0.00 | 0.00 |
|  | Stat | n.a.[#] | n.a. |
| Group 2 | Mean | 4.00 | 4.00 |
| DBM 1 + BMP-2 | SD | 0.00 | 0.00 |
|  | Stat | n.s.[&] | n.s. |
| Group 3 | Mean | 1.25 | 1.50 |
| DBM 1 + Calcium | SD | 0.96 | 1.29 |
| phosphate mineral 1.0% | Stat | 0.0020 | 0.2110 |
| Group 4 | Mean | 2.00 | 2.00 |
| DBM 2 | SD | 2.31 | 2.31 |
| (Puros ® DBM Putty) | Stat | n.s. | n.s. |
| Group 5 | Mean | 3.00 | 3.50 |
| DBM 1 + Calcium | SD | 0.82 | 0.58 |
| phosphate mineral 5% | Stat | n.s. | n.s. |
| Group 6 | Mean | 3.75 | 3.75 |
| DBM 1 + Calcium | SD | 0.50 | 0.50 |
| phosphate mineral 10.0% | Stat | n.s. | n.s. |
| Group 7 | Mean | 1.67 | 1.67 |
| Collagen + BMP-2 | SD | 0.58 | 0.58 |
|  | stat | 0.0301 | 0.0301 |
| Group 8 | Mean | 1.50 | 1.50 |
| Decortication only on left side | SD | 2.12 | 2.12 |
| Negative control | Stat | n.s. | n.s. |

Stat = a non-parametric rank sum Wilcoxon test
[#]n.a. = not applicable
[&]n.s. = not significant when compared to Group 1 control group The data from the histology scores showed remarkable differences between DBM 1 and Puros® DBM putty; the former facilitated a better overall outcome for osteoinductivity or bone formation in this spinal fusion model. From the total scores, good overall fusion was evident with DBM 1 or the DBM 1 combined with BMP-2 or 10% CaP indicating that this combination may reduce the bulk amount of DBM 1 needed to fill in the space between the spinal processes of the two adjacent vertebral segments. Overall, there was more fusion mass evident with DBM 1+10% CaP compared to that with collagen+BMP-2. The proportion of added CaP may indicate the advantage to have a higher percentage in fusing the vertebral segments.

The score for each parameter was summed for all animals in a group and the averages of the scores in the sagittal and transverse planes are shown in Tables 14 and 15, respectively. Groups 4 (Puros® DBM Putty), 7 (Collagen+BMP-2) and 8 (Decortication only) showed the least fusion activities, while Groups 1 (DBM 1), 2 (DMB 1+BMP-2), and 6 (DBM 1+10% CaP) had significantly more fusion tissues formed. There was a positive trend in fusion and bone formation with increasing calcium phosphate amounts. For many of the measures of bone growth and fusion, the addition of calcium phosphate mineral provided similar or better results than the addition of exogenous BMP-2, particularly at the highest calcium phosphate mineral amount tested. Moreover, the highest calcium phosphate mineral amount employed in implants did not induce fibrosis or inflammation to any greater extent in the sagittal plane relative to implants with exogenous BMP-2. Although the fibrosis and inflammation scores for the highest calcium phosphate amount were greater in the transverse plane relative to BMP-2 implants, the amount of fibrosis and inflammation that was observed was within the acceptable range for implants.

TABLE 14

Summary of Histology Results - Sagittal Plane (Longitudinal)

| Parameter | Data | G1 | G2 | G3 | G4 | G5 | G6 | G7 | G8 |
|---|---|---|---|---|---|---|---|---|---|
| Fibrosis | Mean | 0.67 | 0.5 | 1.5 | 2 | 2 | 0.33 | 0 | 0 |
|  | StDev | 0.58 | 0.71 | 2.12 | 0 | 1 | 0.58 | 0 | N/A |
|  | Count | 3 | 2 | 2 | 2 | 3 | 3 | 3 | 1 |
| Inflammation | Mean | 1 | 0.5 | 0.5 | 1.5 | 1 | 0.33 | 0 | 0 |
|  | StDev | 0 | 0.71 | 0.71 | 0.71 | 0 | 0.58 | 0 | N/A |
|  | Count | 3 | 2 | 2 | 2 | 3 | 3 | 3 | 1 |
| New bone segments | Mean | 0 | 0 | 0 | 0 | 0.67 | 0 | 0 | 0 |
|  | StDev | 0 | 0 | 0 | 0 | 1.15 | 0 | 0 | N/A |
|  | Count | 3 | 2 | 2 | 2 | 3 | 3 | 3 | 1 |
| New bone on implant surfaces | Mean | 1 | 2 | 1 | 0.5 | 2 | 2 | 0 | 0 |
|  | StDev | 0 | 0 | 0 | 0.71 | 1 | 1 | 0 | N/A |
|  | Count | 3 | 2 | 2 | 2 | 3 | 3 | 3 | 1 |
| New cartilage | Mean | 0.33 | 0 | 0 | 0 | 0.67 | 0 | 0 | 0 |
|  | StDev | 0.58 | 0 | 0 | 0 | 1.15 | 0 | 0 | N/A |
|  | Count | 3 | 2 | 2 | 2 | 3 | 3 | 3 | 1 |
| Fusion of implants and existing bone | Mean | 4 | 3 | 2.5 | 0 | 3.67 | 4 | 0 | 0 |
|  | StDev | 0 | 1.41 | 0.71 | 0 | 0.58 | 0 | 0 | N/A |
|  | Count | 3 | 2 | 2 | 2 | 3 | 3 | 3 | 1 |
| Fusion of implants | Mean | 3.67 | 3.5 | 1.5 | 0.5 | 3.33 | 4 | 0 | 0 |
|  | StDev | 0.58 | 0.71 | 0.71 | 0.71 | 1.15 | 0 | 0 | N/A |
|  | Count | 3 | 2 | 2 | 2 | 3 | 3 | 3 | 1 |
| Amount of new bone labeled | Mean | 2.33 | 2 | 2.5 | 0.5 | 2.67 | 2.67 | 0 | 0 |
|  | StDev | 1.53 | 0 | 0.71 | 0.71 | 0.58 | 1.53 | 0 | N/A |
|  | Count | 3 | 2 | 2 | 2 | 3 | 3 | 3 | 1 |

TABLE 15

Summary of Histology Results - Transverse Plane (Cross-Sectional)

| Parameter | Data | G1 | G2 | G3 | G4 | G5 | G6 | G7 | G8 |
|---|---|---|---|---|---|---|---|---|---|
| Fibrosis | Mean | 0.33 | 0.50 | 2.00 | 2.50 | 2.33 | 1.33 | 0.00 | 0.00 |
|  | StDev | 0.58 | 0.71 | 0.00 | 0.71 | 0.58 | 0.58 | 0.00 | N/A |
|  | Count | 3 | 2 | 2 | 2 | 3 | 3 | 3 | 1 |
| Inflammation | Mean | 0.33 | 0.50 | 1.50 | 1.50 | 1.00 | 1.00 | 0.00 | 0.00 |
|  | StDev | 0.58 | 0.71 | 0.71 | 0.71 | 0.00 | 0.00 | 0.00 | N/A |
|  | Count | 3 | 2 | 2 | 2 | 3 | 3 | 3 | 1 |
| New bone segments | Mean | 0.00 | 0.00 | 0.00 | 0.00 | 0.00 | 0.00 | 0.00 | 0.00 |
|  | StDev | 0.00 | 0.00 | 0.00 | 0.00 | 0.00 | 0.00 | 0.00 | N/A |
|  | Count | 3 | 2 | 2 | 2 | 3 | 3 | 3 | 1 |
| New bone on implant surfaces | Mean | 2.00 | 1.50 | 1.00 | 0.50 | 1.00 | 2.00 | 0.33 | 0.00 |
|  | StDev | 1.00 | 0.71 | 0.00 | 0.71 | 1.00 | 1.00 | 0.58 | N/A |
|  | Count | 3 | 2 | 2 | 2 | 3 | 3 | 3 | 1 |
| New cartilage | Mean | 0.00 | 0.00 | 0.00 | 0.00 | 0.33 | 0.00 | 0.00 | 0.00 |
|  | StDev | 0.00 | 0.00 | 0.00 | 0.00 | 0.58 | 0.00 | 0.00 | N/A |
|  | Count | 3 | 2 | 2 | 2 | 3 | 3 | 3 | 1 |
| Fusion of implants and existing bone | Mean | 3.00 | 3.00 | 2.00 | 0.50 | 1.00 | 3.33 | 1.33 | 0.00 |
|  | StDev | 1.00 | 1.41 | 1.41 | 0.71 | 1.00 | 0.58 | 2.31 | N/A |
|  | Count | 3 | 2 | 2 | 2 | 3 | 3 | 3 | 1 |
| Fusion of implants | Mean | 4.00 | 4.00 | 2.50 | 0.50 | 1.00 | 4.00 | 1.33 | 0.00 |
|  | StDev | 0.00 | 0.00 | 0.71 | 0.71 | 1.73 | 0.00 | 2.31 | N/A |
|  | Count | 3 | 2 | 2 | 2 | 3 | 3 | 3 | 1 |
| Amount of new bone labeled | Mean | 2.00 | 2.00 | 2.00 | 0.50 | 1.67 | 2.33 | 1.00 | 0.00 |
|  | StDev | 1.00 | 0.00 | 0.00 | 0.71 | 1.15 | 1.53 | 1.73 | N/A |
|  | Count | 3 | 2 | 2 | 2 | 3 | 3 | 3 | 1 |

In summary, the bone void filler compositions of the invention had a fusion rate similar to compositions with BMP-2. In addition, the fusion mass for animals treated with bone void filler compositions of the invention was significantly larger than for animals treated with compositions with BMP-2. Also, a larger trabecular volume was observed in animals treated with bone void filler compositions of the invention. Treatment with the bone void filler compositions of the invention result in more new bone forming regions, consistent with increased new bone volume.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. For example, while the primary intended use of the composition of the present invention is for use as a bone void filler, it is envisioned that the composition could be used for other purposes. It is therefore evident that the particular illustrative embodiments disclosed above may be altered or modified and all such variations are considered within the scope and spirit of the present invention. The indefinite articles "a" or "an", as used in the claims, are defined herein to mean one or more than one of the element that it introduces.

Where a range of values is provided, it is understood that each intervening value, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A bone void filler composition comprising:
an acidic calcium phosphate component from about 8 wt % to about 12 wt % of the composition;
an osteoinductive demineralized bone component from about 70 wt % to about 80 wt % of the composition; and
an osteoconductive collagen carrier component from about 10 wt % to about 16 wt % of the composition;
wherein the composition is in the form of a porous three dimensional structure; and
wherein the composition has a pH from about 3 to about 5; with the proviso that the acidic calcium phosphate component is not $Ca_3(PO_4)2H_2O$.

2. The bone void filler composition of claim 1, wherein the acidic calcium phosphate component comprises monocalcium phosphate monohydrate [$Ca(H_2PO_4)2H_2O$]; calcium hydrogen phosphate dihydrate [$CaHPO_42H_2O$], anhydrous calcium hydrogen phosphate [$CaHPO_4$], partially dehydrated calcium hydrogen phosphate [$CaHPO_4xH_2O$, where x is between 0 and 2], and/or calcium pyrophosphate ($Ca_2O_7P_2$) [$2CaO_2P_2O_5$].

3. The bone void filler composition of claim 2, wherein the acidic calcium phosphate component comprises anhydrous calcium hydrogen phosphate [$CaHPO_4$], partially dehydrated calcium hydrogen phosphate [$CaHPO_4xH_2O$, where x is between 0 and 2], and/or calcium hydrogen phosphate dihydrate [$CaHPO_42H_2O$].

4. The bone void filler composition of claim 1, further comprising an additive selected from the group consisting of allograft chips, bioceramics, biocomposites, calcium salts other than the acidic calcium phosphate component, phosphate salts other than the acidic calcium phosphate component; and combinations thereof.

5. The bone void filler composition of claim 1, further comprising an additive selected from the group consisting of bioresorbable fibers, synthetic polymers, and combinations thereof.

6. The bone void filler composition of claim 1, wherein the demineralized bone is in a form selected from a powder, particle, granule, fiber, and combinations thereof.

7. The bone void filler composition of claim 6, wherein the demineralized bone is in a form selected from a particle, granule, and combinations thereof.

8. The bone void filler composition of claim 7, wherein the demineralized bone particle or granule size is from about 105 μm to about 850 μm.

9. The bone void filler composition of claim 1, wherein the demineralized bone component is derived from a human donor.

10. The bone void filler composition of claim 1, wherein the osteoconductive collagen carrier component comprises collagen from a non-human mammal.

11. The bone void filler composition of claim 10, wherein the osteoconductive collagen carrier component comprises bovine collagen.

12. The bone void filler composition of claim 10, wherein the osteoconductive collagen component comprises Type I and/or Type III collagen.

13. The bone void filler composition of claim 12, wherein the osteoconductive collagen component comprises more than about 90 wt % Type I and less than about 10 wt % Type III collagen.

14. The bone void filler composition of claim 1, further comprising a liquid carrier selected from selected from the group consisting of i) biological fluids selected from the group consisting of bone marrow aspirate, whole blood, serum, and/or plasma, ii) biocompatible liquids selected from the group consisting of water, saline and/or aqueous buffers, and iii) combinations of i) and ii).

15. The bone void filler composition of claim 14, wherein the liquid carrier comprises bone marrow aspirate and saline.

16. The bone void filler composition of claim 1, which is lyophilized.

17. The bone void filler composition of claim 1, wherein the porous three dimensional structure is in the form of a strip, disc, sheet, bullet or cylinder.

18. The bone void filler composition of claim 1, wherein the porous three dimensional structure is shaped for dental ridge augmentation.

* * * * *

UNITED STATES PATENT AND TRADEMARK OFFICE
CERTIFICATE OF CORRECTION

Page 1 of 4

PATENT NO. : 8,613,938 B2
APPLICATION NO. : 13/297005
DATED : December 24, 2013
INVENTOR(S) : Akella et al.

It is certified that error appears in the above-identified patent and that said Letters Patent is hereby corrected as shown below:

On the Title Page

On page 7, in column 2, under "Other Publications", line 1, delete "12/748,999 ," and insert --12/748,999,--, therefor On page 7, in column 2, under "Other Publications", line 21, after "Action", insert --mailed--, therefor On page 7, in column 2, under "Other Publications", line 51, delete "Matriz" and insert --Matrix--, therefor On page 7, in column 2, under "Other Publications", line 57, delete "12/849,414 ," and insert --12/849,414,--, therefor On page 7, in column 2, under "Other Publications", line 61, delete "Mailed" and insert --mailed--, therefor On page 8, in column 1, under "Other Publications", line 1, delete "T," and insert --T.,--, therefor On page 8, in column 1, under "Other Publications", line 4, delete "C," and insert --C.,--, therefor On page 8, in column 1, under "Other Publications", line 7, delete "K," and insert --K.,--, therefor On page 8, in column 1, under "Other Publications", line 12, delete "O," and insert --O.,--, therefor On page 8, in column 1, under "Other Publications", line 17, delete "W," and insert --W.,--, therefor On page 8, in column 1, under "Other Publications", line 20, delete "M," and insert --M.,--, therefor On page 8, in column 1, under "Other Publications", line 23, delete "Y," and insert --Y.,--, therefor Signed and Sealed this
Second Day of September, 2014

Michelle K. Lee
*Deputy Director of the United States Patent and Trademark Office*

CERTIFICATE OF CORRECTION (continued)
U.S. Pat. No. 8,613,938 B2

On page 8, in column 1, under "Other Publications", line 38, delete "D," and insert --D.,-- therefor On page 8, in column 1, under "Other Publications", line 43, delete "N," and insert --N.,-- therefor On page 8, in column 1, under "Other Publications", line 59, delete "12/849,414 ," and insert --12/849,414,--, therefor On page 8, in column 2, under "Other Publications", line 9, delete "D A," and insert --D. A.,--, therefor On page 8, in column 2, under "Other Publications", line 11, delete "28,," and insert --28,--, therefor On page 8, in column 2, under "Other Publications", line 16, delete "S S," and insert --S. S.,--, therefor On page 8, in column 2, under "Other Publications", line 19, delete "R Z," and insert --R. Z.,--, therefor On page 8, in column 2, under "Other Publications", line 20, delete "CaHPO4.2h2o (DCPD" and insert --$CaHPO_4.2H_2O$ (DCPD)--, therefor On page 8, in column 2, under "Other Publications", line 22, delete "R Z," and insert --R. Z.,--, therefor On page 8, in column 2, under "Other Publications", line 25, delete "Z," and insert --Z.,--, therefor On page 8, in column 2, under "Other Publications", line 29, delete "G," and insert --G.,--, therefor On page 8, in column 2, under "Other Publications", line 32, delete "G H," and insert --G. H.,--, therefor On page 8, in column 2, under "Other Publications", line 41, delete "H," and insert --H.,--, therefor On page 8, in column 2, under "Other Publications", line 44, delete "S," and insert --S.,--, therefor On page 8, in column 2, under "Other Publications", line 47, delete "W R," and insert --W. R.,--, therefor On page 8, in column 2, under "Other Publications", line 56, delete "S," and insert --S.,--, therefor On page 8, in column 2, under "Other Publications", line 59, delete "R," and insert --R.,--, therefor On page 9, in column 1, under "Other Publications", line 45, delete "Nov. 25, 2011" and insert --Nov. 25, 2002--, therefor On page 9, in column 2, under "Other Publications", line 59, delete "mailed" and insert --filed--, therefor On page 9, in column 2, under "Other Publications", line 67, delete "received" and insert --filed--, therefor On page 9, in column 2, under "Other Publications", line 69, delete "received" and insert --filed--, therefor On page 10, in column 1, under "Other Publications", line 43, after "Report", insert --mailed--, therefor On page 10, in column 1, under "Other Publications", line 45, after "Opinion", insert --mailed--, therefor On page 10, in column 1, under "Other Publications", line 57, delete "Received" and insert --mailed--, therefor On page 10, in column 2, under "Other Publications", line 22, delete "D," and insert --D.,--, therefor On page 10, in column 2, under "Other Publications", line 34, delete "G," and insert --G.,--, therefor On page 10, in column 2, under "Other Publications", line 43, delete "N," and insert --N.,--, therefor On page 10, in column 2, under "Other Publications", line 46, delete "N," and insert --N.,--, therefor On page 10, in column 2, under "Other Publications", line 49, delete "J," and insert --J.,--, therefor On page 10, in column 2, under "Other Publications", line 66, Delete "AtelocollagenlHydroxylapatite" and insert --Atelocollagen/Hydroxylapatite--, therefor On page 11, in column 1, under "Other Publications", line 6, delete "Hsiu-O," and insert --Hsiu-O.,--, therefor On page 11, in column 1, under "Other Publications", line 6, delete "collage" and insert --collagen--, therefor On page 11, in column 1, under "Other Publications", line 10, delete "ed.,," and insert --ed.,--, therefor On page 11, in column 1, under "Other Publications", line 11, delete "hydroxyapatite Ire constituted" and insert --hydroxyapatite/reconstituted--, therefor On page 11, in column 1, under "Other Publications", line 12, delete "Biornaterials" and insert --Biomaterials--, therefor On page 11, in column 1, under "Other Publications", line 35, Delete """," and insert --"The Use of Composite Bone Graft Materials in a Segmental Femoral Defect Model in the Rat",--, therefor On page 11, in column 1, under "Other Publications", line 41, delete "M," and insert --M.,-- therefor On page 11, in column 1, under "Other Publications", line 48, delete "bonelgraft" and insert --bone/graft--, therefor On page 11, in column 1, under "Other Publications", line 49, delete "hydroxylapatitelpurified" and insert --hydroxylapatite/purified--, therefor On page 11, in column 1, under "Other Publications", line 52, delete "fo" and insert --of--, therefor On page 11, in column 1, under "Other Publications", line 54, delete "J.Periodontol.,," and insert --J. Periodontol.,-- therefor On page 11, in column 2, under "Other Publications", line 1, delete "F," and insert --F.,-- therefor On page 11, in column 2, under "Other Publications", line 6, delete "M," and insert --M.,-- therefor On page 11, in column 2, under "Other Publications", line 9, delete "M," and insert --M.,-- therefor On page 11, in column 2, under "Other Publications", line 21, delete "Y," and insert --Y.,-- therefor On page 11, in column 2, under "Other Publications", line 36, delete "Biornaterials" and insert --Biomaterials--, therefor On page 11, in column 2, under "Other Publications", line 56, delete "D," and insert --D.,-- therefor On page 11, in column 2, under "Other Publications", line 60, delete "E," and insert --E.,-- therefor In the Claims In column 40, line 47, in claim 14, after "carrier", delete the first occurrence of "selected from"